United States Patent
Hanaki et al.

(10) Patent No.: US 7,219,988 B2
(45) Date of Patent: *May 22, 2007

(54) WATER-SOLUBLE PHTHALOCYANINE COMPOUND-CONTAINING INK FOR INK JETTING, INK JET RECORDING METHOD AND METHOD FOR IMPROVING OZONE GAS DISCOLORATION OF COLORED IMAGE MATERIAL

(75) Inventors: Naoyuki Hanaki, Minami-Ashigara (JP); Keiichi Tateishi, Minami-Ashigara (JP); Shigeaki Tanaka, Minami-Ashigara (JP)

(73) Assignee: Fuji Photo Film Co., Ltd., Minami-Ashigara-Shi, Kanagawa (JP)

(*) Notice: Subject to any disclaimer, the term of this patent is extended or adjusted under 35 U.S.C. 154(b) by 229 days.

This patent is subject to a terminal disclaimer.

(21) Appl. No.: 10/502,217

(22) PCT Filed: Jan. 17, 2003

(86) PCT No.: PCT/JP03/00371

§ 371 (c)(1),
(2), (4) Date: Jul. 21, 2004

(87) PCT Pub. No.: WO03/062323

PCT Pub. Date: Jul. 31, 2003

(65) Prior Publication Data

US 2005/0073563 A1     Apr. 7, 2005

(30) Foreign Application Priority Data

Jan. 22, 2002   (JP)   ............................. 2002-012864

(51) Int. Cl.
*G01D 11/00*     (2006.01)

(52) U.S. Cl. ...................... 347/100; 347/95; 106/31.27
(58) Field of Classification Search ................ 347/100, 347/101, 95, 96; 523/160; 106/31.27, 31.6, 106/31.13
See application file for complete search history.

(56) References Cited

U.S. PATENT DOCUMENTS

| | | | | |
|---|---|---|---|---|
| 5,739,319 A | * | 4/1998 | Yamasaki | .................... 106/410 |
| 7,087,107 B2 | * | 8/2006 | Tateishi et al. | ............. 347/100 |
| 2001/0011396 A1 | | 8/2001 | Carr | |

FOREIGN PATENT DOCUMENTS

| | | |
|---|---|---|
| EP | 0 763 539 | 3/1997 |
| GB | 2 341 868 | 3/2000 |
| WO | 00 64901 | 11/2000 |
| WO | 01 66647 | 9/2001 |
| WO | 01 66648 | 9/2001 |
| WO | 02 08340 | 1/2002 |
| WO | 02 088256 | 11/2002 |

* cited by examiner

*Primary Examiner*—Manish S. Shah
(74) *Attorney, Agent, or Firm*—Buchanan Ingersoll & Rooney PC

(57) ABSTRACT

An ink including a water-soluble phthalocyanine compound, wherein in the spectral absorption curve of an aqueous solution of the phthalocyanine compound, the absorbance ratio b/a of the maximum absorbance b in the absorption band of 660 to 680 nm and the maximum absorbance a in the absorption band of 600 to 640 nm is less than 0.8 and the counter ion for the ionic hydrophilic group of the phthalocyanine compound is lithium ion. The ink can provide an image having excellent (color) hue and high fastness to light and ozone gas, can be used as an ink for an ink jet and can be used in an ink jet recording method.

10 Claims, No Drawings

WATER-SOLUBLE PHTHALOCYANINE COMPOUND-CONTAINING INK FOR INK JETTING, INK JET RECORDING METHOD AND METHOD FOR IMPROVING OZONE GAS DISCOLORATION OF COLORED IMAGE MATERIAL

TECHNICAL FIELD

The present invention relates to a coloring composition containing a medium and a phthalocyanine compound, more specifically, the present invention relates to an ink, a coating material, particularly cyan color ink, an ink for ink jet recording, an ink jet recording method and a method for improving ozone gas discoloration resistance of an image recorded material obtained by ink jet recording.

BACKGROUND ART

In recent years, the image recording material is predominated particularly by a material for forming a color image. More specifically, a recording material using an ink jet system, a recording material using a heat-sensitive transfer system, a recording material using an electro-photographic system, a silver halide light-sensitive material using a transfer system, a printing ink, a recording pen and the like are popularly used. Also, a color filter for recording/reproducing a color image is used in an image pick-up element such as CCD of photographing equipment, or in LCD or PDP of display. In these color image recording materials or color filters, three primary color dyes (dyes or pigments) by a so-called additive or subtractive color mixing method are used for reproducing or recording a full color image, however, a dye having absorption properties capable of realizing a preferred color reproduction region and having fastness capable of enduring various use and environmental conditions is not found at present and improvements are keenly demanded.

The ink jet recording method has been abruptly spread and is further growing because the material cost is low, high-speed recording can be obtained, noises are less generated at the recording and color recording is easy. The ink jet recording method includes a continuous system of continuously jetting out a liquid droplet and an on-demand system of jetting out a liquid droplet according to image information signals, and the ejection system therefore includes a system of ejecting a liquid droplet by generating bubbles in ink using heat, a system of using an ultrasonic wave, and a system of ejecting a liquid droplet by suction using an electrostatic force. The ink used for ink jetting includes an aqueous ink, an oily ink and a solid (fusion-type) ink.

The dye used in the ink for ink jetting is required to have good solubility or dispersibility in a solvent, enable high-density recording, provide good (color) hue, have fastness to light, heat and active gas in environment (for example, oxidative gas such as NOx and ozone, and SOx), exhibit excellent resistance against water and chemicals, ensure good fixing property to an image-receiving material to cause less blurring, give an ink having excellent storability, have no toxicity and high purity and be available at a low cost.

In particular, the dye is strongly demanded to have good cyan color and fastness to light, humidity and heat and when printed on an image-receiving material having an ink-accepting layer containing a porous white inorganic pigment particle, be resistant against oxidative gas such as ozone in the environment.

A representative skeleton of the cyan dye used for ink is a phthalocyanine or triphenylmethane structure. Representative examples of the phthalocyanine compound which has been reported and is used over the widest range include phthalocyanine derivatives classified into the following (1) to (6):

(1) copper phthalocyanine compounds such as Direct Blue 86 and Direct blue 87 [for example, $Cu\text{-}Pc\text{-}(SO_3Na)_m$: a mixture of m=1 to 4] (hereinafter, Pc means a phthalocyanine skeleton);

(2) Direct Blue 199 and phthalocyanine dyes described in JP-A-62-190273 (the term "JP-A" as used herein means an "unexamined published Japanese patent application"), JP-A-63-28690, JP-A-63-306075, JP-A-63-306076, JP-A-2-131983, JP-A-3-122171, JP-A-3-200883, JP-A-7-138511, etc. [for example, $Cu\text{-}Pc\text{-}(SO_3Na)_m(SO_2NH_2)_n$: a mixture of m+n=1 to 4];

(3) phthalocyanine-base dyes described in JP-A-63-210175, JP-A-63-37176, JP-A-63-304071, JP-A-5-171085, WO00/08102, etc. [for example, $Cu\text{-}Pc\text{-}(CO_2H)_m(CONR_1R_2)_n$: a mixture of m+n=0 to 4];

(4) phthalocyanine-base dyes described in JP-A-59-30874, JP-A-1-126381, JP-A-1-190770, JP-A-6-16982, JP-A-7-82499, JP-A-8-34942, JP-A-8-60053, JP-A-8-113745, JP-A-8-310116, JP-A-10-140063, JP-A-10-298463, JP-A-11-29729, JP-A-11-320921, EP-A-173476, EP-A-468649, EP-A-559309, EP-A-596383, German Patent 3,411,476, U.S. Pat. No. 6,086,955, WO99/13009, British Patent Publication 2,341,868A, etc. [for example, $Cu\text{-}Pc\text{-}(SO_3H)_m(SO_2NR_1R_2)_n$: a mixture of m+n=0 to 4, and m≠0];

(5) phthalocyanine-base dyes described in JP-A-60-208365, JP-A-61-2772, JP-A-6-57653, JP-A-8-60052, JP-A-8-295819, JP-A-10-130517, JP-A-11-72614, Japanese Unexamined Published International Application Nos. 11-515047 and 11-515048, EP-A-196901, WO95/29208, WO98/49239, WO98/49240, WO99/50363, WO99/67334, etc. [for example, $Cu\text{-}Pc\text{-}(SO_3H)_l(SO_2NH_2)_m(SO_2NR_1R_2)_n$: a mixture of l+m+n=0 to 4]; and (6) phthalocyanine-base dyes described in JP-A-59-22967, JP-A-61-185576, JP-A-1-95093, JP-A-3-195783, EP-A-649881, WO00/08101, WO00/08103, etc. [for example, $Cu\text{-}Pc\text{-}(SO_2NR_1R_2)_n$: a mixture of n=1 to 5].

Phthalocyanine-base dyes widely used in general at present, represented by Direct Blue 87 and Direct Blue 199, are excellent in the light fastness as compared with generally known magenta dyes, yellow dyes and triphenylmethane-base cyanine dyes.

However, the phthalocyanine-base dyes provide a greenish (color) hue under acidic conditions and are improper for a cyan ink. In the case of using these dyes for a cyanine ink, these are most suitably used under conditions from neutral to alkaline. However, even if the ink is in the region from neutral to alkaline, when the material on which an image or the like is recorded is an acidic paper, the (color) hue of the printed matter may greatly change.

Furthermore, discoloration to a greenish (color) hue or decoloration occurs due to oxidative gases such as nitrogen oxide gas and ozone, which are often taken as a problem also from an environmental issue, and this simultaneously causes reduction in the printing density.

On the other hand, triphenylmethane-base dyes provide a good (color) hue but are very inferior in the light fastness, resistance against ozone gas and the like.

If the use field hereafter expands and the printed matter is widely used for exhibition such as advertisement, the case of being exposed to light or active gas in the environment increases and to cope with this, a dye and an ink composition having light fastness and excellent resistance against active gases (for example, oxidative gas such as NOx and ozone, and SOx) in the environment are more strongly demanded.

However, it is very difficult to find out a cyan dye (for example, phthalocyanine-base dye) and a cyan ink satisfying these requirements in a high level.

As for the ink for an ink jet recording system, an aqueous dye ink obtained by dissolving a water-soluble dye of various types in a liquid medium comprising water and a water-soluble organic solvent, an aqueous pigment ink obtained by dispersing a pigment of various types in a liquid medium comprising water and a water-soluble organic solvent, an oily dye ink obtained by dissolving an oil-soluble dye in an organic solvent, and the like are known. Among these inks, the aqueous ink obtained by dissolving an aqueous dye is excellent in the safety because the main solvent is water, enables good coloring of a color image and formation of a high-grade printed image because a dye is used, and also exhibits excellent ink storage stability. Therefore, this aqueous ink is predominating as an ink for ink jet recording.

The phthalocyanine-base dyes imparted with water solubility are heretofore disclosed, for example, in WO00/08102, JP-A-2000-303014 and JP-A-2000-313837, however, none of these dyes have succeeded in satisfying both the (color) hue and the fastness to light and oxidative gas. A cyan ink product fully satisfying the requirements on the market is not yet provided.

When a recorded image having a high optical density is formed, this is accompanied with a problem that as the image is dried, the dye crystal deposits on the surface of the recording material and the recorded image reflects light to cause a so-called bronze phenomenon of emitting metallic gloss. This phenomenon is considered to readily occur when the water solubility of dye is decreased so as to improve water resistance or an amino group of a hydrogen bond group is introduced into the dye structure, because the dye is elevated in the associating (aggregating) property. The generation of bronze phenomenon not only incurs decrease in the optical density of the recorded image but also causes great difference from the desired (color) hue of the recorded image. Therefore, it is one of important performances required of the ink for ink jetting to prevent the bronze phenomenon.

Known examples of the method for preventing the bronze phenomenon include a method of adding a specific nitrogen-containing compound (see, for example, JP-A-55-120676, JP-A-62-119280, JP-A-64-6072, JP-A-1-152176, JP-A-2-41369, JP-A-5-125311, JP-A-6-25575, JP-A-6-128515, JP-A-6-228476, JP-A-6-228483, JP-A-6-248212, JP-A-7-228810, JP-A-7-268261, JP-A-8-259865, JP-A-9-12944, JP-A-9-12946, JP-A-9-12949 and JP-A-10-36735) and a method of adding a specific titanium compound (see, JP-A-8-337745). The bronze phenomenon may be prevented from occurring by adding these compounds, however, there is a fear that the additives decrease various performances of ink and the quality of recorded image. For example, as described in JP-A-8-259865, when an alkanolamine is added to the ink, the bronze phenomenon can be prevented but by the addition only in a small amount, the pH of ink increases to 11 or more and the high pH ink not only adversely affects nozzles but also lacks in safety on erroneously contacting with a human body and moreover, decreases the printing grade or water resistance of the recorded image.

Other than these, examples of the method for improving the performance of ink for ink jetted by using an additive are described in JP-A-5-339532 and JP-A-2001-254040 where an anionic additive except for dyes, having lithium ion, quaternary ammonium ion or quaternary phosphonium ion as the counter cation is added and thereby, even when the counter ion of the dye is not such ion, an effect of preventing clogging is obtained because the solubility is improved. On the other hand, JP-A-7-26178 describes a technique where an alkali metal compound is added to ink and thereby, the production of an aggregate of dye is prevented, as a result, the viscosity of ink does not increase. However, in JP-A-1036735, it is pointed out that this improvement effect can be attained when the storage time is short, but when stored for a long period of time, the storage stability has a problem.

As such, various effects can be obtained by using additives, however, various performances can be hardly maintained if additives are used. Particularly, in the case where the solubility and aggregating property of dye must be taken account of, selection of the kind and amount of additive is difficult. In using an ionic additive, the effect thereof on the counter ion must also be taken into consideration. Accordingly, a substantial bronze phenomenon-inhibiting method not relying on additives is preferred.

Studies are being aggressively made with an attempt to improve various performances required of the ink for ink jetting by changing the counter ion for the ionic hydrophilic group of metal phthalocyanine compounds and examples thereof include JP-A-5-339532, JP-A-6-16982, JP-A-6-248212, JP-A-6-322286, JP-A-7-138511 and JP-A-10-130517.

For example, in JP-A-57-202358, JP-A-63-81179, JP-A-63-317568 and Japanese Patents 2581769 and 3163176, lithium ion is referred to as preferred counter ion for the ionic hydrophilic group of metal phthalocyanine dyes and it is stated that this ion is effective for providing an ink having high concentration, storage stability and jetting stability. On the other hand, JP-A-7-82499 states that lithium ion is not preferred as the counter cation, because the water resistance of the recorded image decreases due to high water solubility of the dye. From these, it is seen that the performances required of the ink for ink jetting cannot be easily satisfied merely by changing the counter salt.

As described above, an ink capable of satisfying all of various performances required of the water-soluble ink for ink jetting is not yet found at present.

Problems to be Solved by the Invention:

The present invention has been made to solve those problems in conventional techniques and achieve the following objects. That is, the objects of the present invention are (1) to provide a novel ink having absorption properties ensuring excellent color reproduction as a dye for three primary colors and at the same time, having sufficiently high fastness to light, heat, humidity and active gas in the environment;

(2) to provide an ink of giving a colored image or colored material excellent in the (color) hue and the fastness, for example, an ink composition for printing such as ink jetting;

(3) to provide an ink for ink jet recording and an ink jet recording method, which can form an image having good (color) hue by the use of a phthalocyanine compound derivative, having high fastness particularly against ozone gas and free of generation of a bronze phenomenon; and (4) to provide a method for forming an image having fastness by using the above-described ink jet recording method and thereby improving the ozone gas discoloration resistance of the image recorded material.

Means to Solve the Problems:

As a result of extensive investigations on phthalocyanine derivatives of providing good (color) hue, generating no bronze phenomenon and ensuring fastness to light and gas (particularly ozone gas), the present inventors have found that the above-described objects can be attained by a phthalocyanine compound where the counter cation of the ionic hydrophilic group is lithium ion, particularly a phthalocyanine compound represented by the following formula (I), having (1) a specific spectral absorption curve and (2) a specific dye structure (specific substituents are introduced into specific substitution sites in a specific number of substituents), more particularly, a phthalocyanine compound represented by formula (II) or (III).

DISCLOSURE OF THE INVENTION

The present invention has been accomplished based on this finding. More specifically, the objects of the present invention can be attained by the following means.

1. An ink comprising a water-soluble phthalocyanine compound, wherein in the spectral absorption curve of an aqueous solution of the phthalocyanine compound, the absorbance ratio b/a of the maximum absorbance b in the absorption band of 660 to 680 nm and the maximum absorbance a in the absorption band of 600 to 640 nm is less than 0.8 and the counter ion for the ionic hydrophilic group of the phthalocyanine compound is lithium ion.

2. The ink as described in 1, wherein the water-soluble phthalocyanine compound is represented by the following formula (I):

Formula (I):

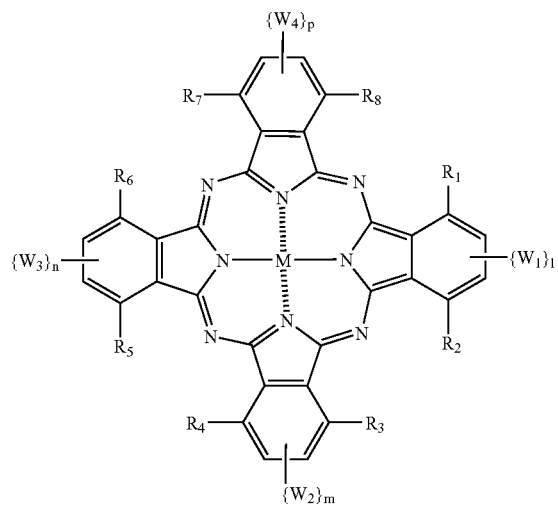

wherein $R_1$, $R_2$, $R_3$, $R_4$, $R_5$, $R_6$, $R_7$ and $R_8$ each independently represents a hydrogen atom, a halogen atom, an alkyl group, a cycloalkyl group, an alkenyl group, an aralkyl group, an aryl group, a heterocyclic group, a cyano group, a hydroxyl group, a nitro group, an amino group, an alkylamino group, an alkoxy group, an aryloxy group, an amido group, an arylamino group, a ureido group, a sulfamoylamino group, an alkylthio group, an arylthio group, an alkoxycarbonylamino group, a sulfonamido group, a carbamoyl group, a sulfamoyl group, a sulfonyl group, an alkoxycarbonyl group, a heterocyclic oxy group, an azo group, an acyloxy group, a carbamoyloxy group, a silyloxy group, an aryloxycarbonyl group, an aryloxycarbonylamino group, an imido group, a heterocyclic thio group, a sulfinyl group, a phosphoryl group or an acyl group and each may further have a substituent;

$W_1$, $W_2$, $W_3$ and $W_4$ each independently represents the group represented by $R_1$, $R_2$, $R_3$, $R_4$, $R_5$, $R_6$, $R_7$ and $R_8$, a sulfonylsulfamoyl group or an acylsulfamoyl group and each may further have a substituent, provided that at least one of $W_1$, $W_2$, $W_3$ and $W_4$ is an ionic hydrophilic group by itself or has an ionic hydrophilic group as a substituent, provided that the counter ion for the ionic hydrophilic group is lithium ion; l, m, n and p each represents an integer of 1 or 2; and M represents a hydrogen atom, a metal element, a metal oxide, a metal hydroxide or a metal halide.

3. The ink as described in 2, wherein the formula (I) is represented by the following formula (II):

Formula (II):

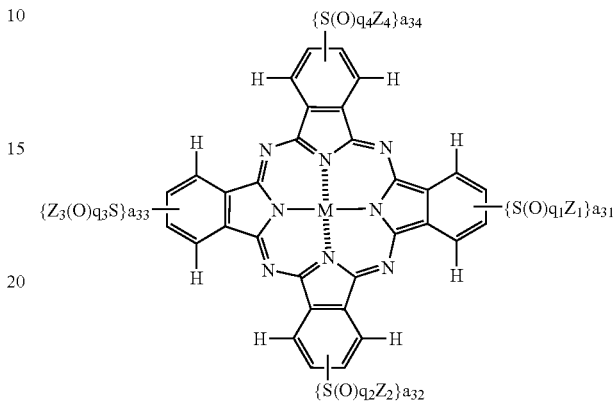

wherein $Z_1$, $Z_2$, $Z_3$ and $Z_4$ each independently represents a substituted or unsubstituted alkyl group, a substituted or unsubstituted cycloalkyl group, a substituted or unsubstituted alkenyl group, a substituted or unsubstituted aralkyl group, a substituted or unsubstituted aryl group or a substituted or unsubstituted heterocyclic group, $q_1$, $q_2$, $q_3$ and $q_4$ each independently represents an integer of 1 or 2, $a_{31}$, $a_{32}$, $a_{33}$ and $a_{34}$ each independently represents an integer of 1 or 2, M has the same meaning as M in formula (I), and at least one of $Z_1$, $Z_2$, $Z_3$ and $Z_4$ has an ionic hydrophilic group as a substituent, provided that the counter ion for the ionic hydrophilic group is lithium ion.

4. The ink as described in 2, wherein the formula (I) is represented by the following formula (III):

Formula (III):

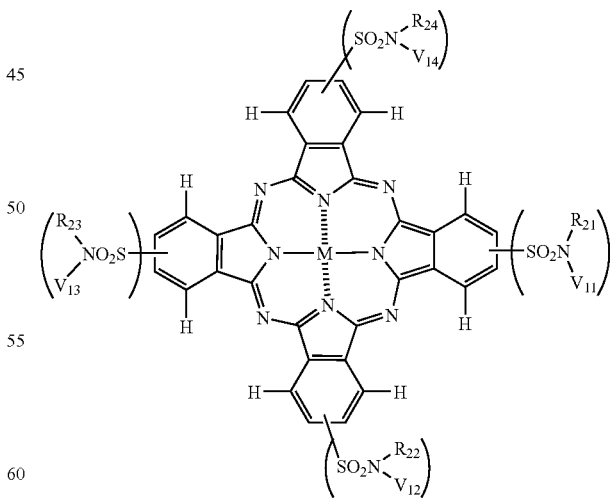

wherein $R_{21}$, $R_{22}$, $R_{23}$ and $R_{24}$ each independently represents a hydrogen atom, a substituted or unsubstituted alkyl group, a substituted or unsubstituted cycloalkyl group, a substituted or unsubstituted alkenyl group, a substituted or unsubstituted aralkyl group, a substituted or unsubstituted aryl group or a substituted or unsubstituted heterocyclic group, $V_{11}$, $V_{12}$, $V_{13}$ and $V_{14}$ each independently represents a substituted or unsubstituted alkyl group, a substituted or unsubstituted cycloalkyl group, a substituted or unsubstituted alkenyl group, a substituted or unsubstituted aralkyl group, a substituted or unsubstituted aryl group, or a substituted or unsubstituted heterocyclic group, M has the same meaning as M in formula (I), and at least one of $R_{21}$, $R_{22}$, $R_{23}$, $R_{24}$, $V_{11}$, $V_{12}$, $V_{13}$ and $V_{14}$ has an ionic hydrophilic group as a substituent, provided that the counter ion for the ionic hydrophilic group is lithium ion.

5. The ink as described in 3, wherein in formula (II), $q_1=q_2=q_3=q_4=2$.

6. An ink for ink jetting, comprising the ink described in any one of 1 to 5.

7. An ink jet recording method comprising forming an image on an image receiving material using the ink for ink jetting described in 6, the image receiving material comprising a support having thereon an ink image-receiving layer containing a white inorganic pigment particle.

8. A method for improving ozone gas discoloration of an image recorded material, comprising forming an image using the ink described in 1 to 6.

9. A water-soluble phthalocyanine compound represented by the following formula (IV):

Formula (IV):

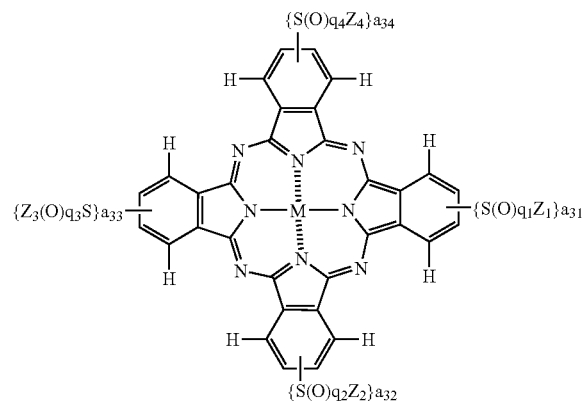

wherein $Z_1$, $Z_2$, $Z_3$ and $Z_4$ each independently represents a substituted or unsubstituted alkyl group, a substituted or unsubstituted cycloalkyl group, a substituted or unsubstituted alkenyl group, a substituted or unsubstituted aralkyl group, a substituted or unsubstituted aryl group or a substituted or unsubstituted heterocyclic group, $q_1$, $q_2$, $q_3$ and $q_4$ each independently represents an integer of 1 or 2, $a_{31}$, $a_{32}$, $a_{33}$ and $a_{34}$ each independently represents an integer of 1 or 2, M has the same meaning as M in formula (I), and at least one of $Z_1$, $Z_2$, $Z_3$ and $Z_4$ has an ionic hydrophilic group as a substituent, provided that the counter ion for the ionic hydrophilic group is lithium ion.

BEST MODE FOR CARRYING OUT THE INVENTION

The present invention is described in detail below. The ink as used in the present invention means a composition comprising a coloring material such as dye or pigment and a dispersant (e.g., solvent) therefor and is suitably used particularly for image formation.

The water-soluble phthalocyanine compound for use in the present invention is characterized by having a specific spectral absorption curve (visible absorption spectrum) and having lithium ion as the counter ion for the ionic hydrophilic group.

In order to grasp the relationship between the structure of cyanine and various performances such as (color) hue, fastness to light and ozone gas, and generation of bronze phenomenon, various phthalocyanine compounds were synthesized and evaluated on the performance. As a result, it has been found that when a phthalocyanine compound having a specific spectral absorption curve and having lithium ion as the counter cation for the ionic hydrophilic group is used, the image can be remarkably prevented from generation of a bronze phenomenon without impairing the performances such as (color) hue and fastness.

The counter cation of the phthalocyanine compound for use in the present invention is lithium ion. It is not necessary that all counter cations are lithium ion, but the counter cation present in a largest proportion must be substantially lithium ion. With such a condition of the presence proportion, alkali metal ion (e.g., sodium ion, potassium ion), alkaline earth metal ion (e.g., magnesium ion, calcium ion), quaternary ammonium ion, quaternary phosphonium ion, sulfonium ion or the like can be contained as the counter cation.

As for the kind and proportion of the counter cation in the above-described phthalocyanine compound, the analysis methods and elements are described in *Shin Jikken Kagaku Koza 9, Bunseki Kagaku* (*Lecture 9 of New Experiment Chemistry, Analysis Chemistry*, compiled by Nippon Kagaku Kai, Maruzen (1977) and *Dai 4 Han, Jikken Kagaku Koza 15, Bunseki* (*4th Edition, Lecture 15 of Experiment Chemistry, Analysis*), compiled by Nippon Kagaku Kai, Maruzen (1991). By referring to these publications, the analysis method can be selected and the analysis and determination can be made. In particular, the determination can be easily performed by an analysis method such as ion chromatography, atomic absorption method or induction coupled plasma emission analysis method (ICP).

The amount of lithium ion in the phthalocyanine compound is 50% or more, preferably 60% or more, more preferably 80% or more, still more preferably 90% or more, with a preferred upper limit of 100%, based on the entire counter ion.

The phthalocyanine compound of the present invention having lithium ion as the counter cation may be obtained by any method. Examples of the method include (1) a method of converting the counter cation into lithium ion from other cation using ion exchange resin, (2) a method of depositing lithium ion with acid or salt from a system containing lithium ion, (3) a method of forming phthalocyanine using a raw material or synthesis intermediate where the counter cation is lithium ion, (4) a method of converting the functional group of a phthalocyanine compound using a reacting agent where the counter cation is lithium ion, and thereby introducing an ionic hydrophilic group, and (5) a method of synthesizing a compound where the counter cation for the ionic hydrophilic group on a phthalocyanine compound is silver ion, reacting the compound with a lithium halide solution, and removing the precipitated silver halide, thereby changing the counter cation to lithium ion.

Examples of the ionic hydrophilic group in the phthalocyanine compound include a sulfo group ($-SO_3^-X^+$), a carboxyl group ($-CO_2^-X^+$), a quaternary ammonium group ($-N^+RR'R''X^{31}$), an acylsulfamoyl group ($-SO_2N^-X^+COR$), a sulfonylcarbamoyl group ($-CON^-X^+SO_2-R$) and a sulfonyl-sulfamoyl group ($-SO_2N^-X^+SO_2-R$). In the present invention, in order to have lithium ion as the counter cation, an anionic hydrophilic group must be present. The ionic hydrophilic group is preferably a sulfo group or a carboxyl group, more preferably a sulfo group. In the parentheses above, $X^+$ represents a counter ion and R, R' and R" each represents a substituent.

The phthalocyanine compound for use in the present invention is a compound where in the spectral absorption curve of an aqueous solution thereof, the absorbance ratio b/a of the maximum absorbance b in the absorption band of 660 to 680 nm and the maximum absorbance a in the absorption band of 600 to 640 nm is less than 0.8 and the counter ion for the ionic hydrophilic group of the phthalocyanine compound is lithium ion.

The absorbance ratio as used in the present invention indicates an absorbance ratio obtained under the following conditions. That is, the spectral absorption curve of a solution obtained by 1,000-fold diluting a 2 wt % aqueous solution of phthalocyanine compound with distilled water is determined using a spectrophotometer according to the definition of JIS Z8120-86 by selecting the measuring temperature from the range of 15 to 30° C. and setting the measurement cell length to 10 mm. The ratio b/a of the maximum absorbance b in the absorption band of 660 to 680 nm on the determined spectral absorption curve and the maximum absorbance a in the absorption band of 600 to 640 nm is used as the absorbance ratio.

The absorbance ratio b/a under the conditions specified in the present invention can be easily determined by reading the maximum absorbance a at 600 to 640 nm and the maximum absorbance b at 660 to 680 nm using the above-described spectrophotometer, measurement cell length and pH condition. Incidentally, the distilled water used for the preparation or dilution of the aqueous solution is a distilled water at a pH of 5 to 8.

The aqueous phthalocyanine compound having a specific spectral absorption property value (an absorbance ratio b/a value of less than 0.8) is very important in improving the fastness of the formed image.

More specifically, the maximum absorbance b in the absorption band from 660 to 680 nm and the maximum absorbance b in the absorption band from 600 to 640 nm on the spectral absorption curve obtained by measuring an aqueous solution of a water-soluble phthalocyanine compound using a spectrophotometer according to JIS Z8120-86 are attributable to the absorption of monomer and the absorption of aggregate, respectively. The absorbance ratio b/a value therebetween participates in the fastness of the formed image. The absorbance ratio b/a value is preferably from 0.3 to less than 0.75, more preferably from 0.4 to 0.65.

The aggregate of water-soluble phthalocyanine compound as used in the present invention means an aggregate formed by two or more phthalocyanine molecules. When the aggregate of phthalocyanine compound is used, stability against light, heat and oxidative gas (particularly ozone gas) is remarkably improved as compared with the compound in the monomolecular dispersion state. Furthermore, by the formation of an aggregate, the cyan (color) hue in the absorption spectrum (excellent .absorption property as a cyan dye for image forming materials) is greatly changed for the better.

Whether or not the dye is aggregated can be easily determined from the shift of absorption maximum (λmax) in the absorption spectrum as described, for example, in J. D. Wright (translated by Taro Eguchi), *Bunshi Kessho* (*Molecular Crystal*), Kagaku Dojin. In general, the aggregate is classified into two aggregates, namely, J-aggregate which shifts to the long wave side, and H-aggregate which shifts to the short wave side. In the present invention, an aggregate is formed by the shifting of the absorption maximum to the short wave side and this aggregate is used as the water-soluble phthalocyanine aggregate.

The phthalocyanine compound for use in the present invention may have any structure insofar as the spectral absorption curve of the aqueous solution satisfies the requirements of the present invention and the compound contains an ionic hydrophilic group having lithium ion as the counter cation, however, a compound represented by formula (I) is preferred.

Formula (I):

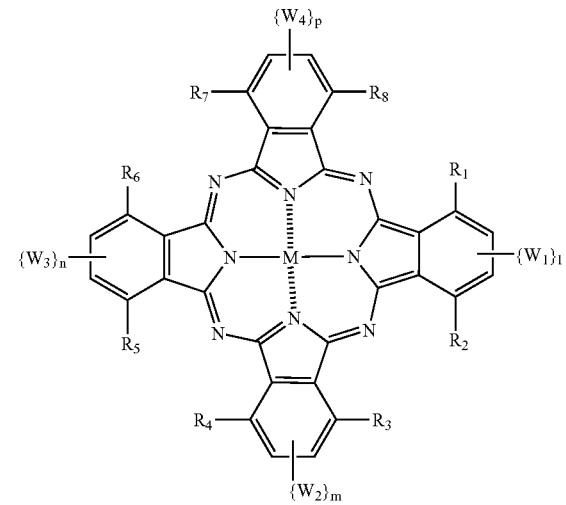

In formula (I), $R_1$, $R_2$, $R_3$, $R_4$, $R_5$, $R_6$, $R_7$ and $R_8$ each independently represents a hydrogen atom, a halogen atom, an alkyl group, a cycloalkyl group, an alkenyl group, an aralkyl group, an aryl group, a heterocyclic group, a cyano group, a hydroxyl group, a nitro group, an amino group, an alkylamino group, an alkoxy group, an aryloxy group, an amido group, an arylamino group, a ureido group, a sulfamoylamino group, an alkylthio group, an arylthio group, an alkoxycarbonylamino group, a sulfonamido group, a carbamoyl group, a sulfamoyl group, a sulfonyl group, an alkoxycarbonyl group, a heterocyclic oxy group, an azo group, an acyloxy group, a carbamoyloxy group, a silyloxy group, an aryloxycarbonyl group, an aryloxycarbonylamino group, an imido group, a heterocyclic thio group, a sulfinyl group, a phosphoryl group or an acyl group and each may further have a substituent.

$R_1$, $R_2$, $R_3$, $R_4$, $R_5$, $R_6$, $R_7$ and $R_8$ each is preferably a hydrogen atom, a halogen atom, an alkyl group, an aryl group, a cyano group, an alkoxy group, an amido group, a ureido group, a sulfonamido group, a carbamoyl group, a sulfamoyl group, a sulfonyl group, an alkoxycarbonyl group or a sulfinyl group, more preferably a hydrogen atom, a halogen atom or a cyano group, and most preferably a hydrogen atom.

$W_1$, $W_2$, $W_3$ and $W_4$ each independently represents a halogen atom, an alkyl group, a cycloalkyl group, an alkenyl group, an aralkyl group, an aryl group, a heterocyclic group, a cyano group, a hydroxyl group, a nitro group, an amino group, an alkylamino group, an alkoxy group, an aryloxy group, an amido group, an arylamino group, a ureido group, a sulfamoylamino group, an alkylthio group, an arylthio group, an alkoxycarbonylamino group, a sulfonamido group, a carbamoyl group, a sulfamoyl group, a sulfonyl group, an alkoxycarbonyl group, a heterocyclic oxy group, an azo group, an acyloxy group, a carbamoyloxy group, a silyloxy group, an aryloxycarbonyl group, an aryloxycarbonylamino group, an imido group, a heterocyclic thio group, a sulfinyl group, a phosphoryl group, an acyl group, a sulfonylsulfamoyl group or an acylsulfamoyl group and each may further have a substituent.

$W_1$, $W_2$, $W_3$ and $W_4$ is preferably an acyl group having from 2 to 12 carbon atoms, an acyloxy group having from 2 to 12 carbon atoms, a carbamoyl group having from 1 to 12 carbon atoms, an alkyloxycarbonyl group having from 2 to 12 carbon atoms, an aryloxycarbonyl group having from 7 to 18 carbon atoms, a cyano group, a nitro group, an alkylsulfinyl group having from 1 to 12 carbon atoms, an arylsulfonyl group having from 6 to 18 carbon atoms, an alkylsulfonyl group having from 1 to 12 carbon atoms, an arylsulfonyl group having from 6 to 18 carbon atoms, a sulfamoyl group having from 0 to 12 carbon atoms, an halogenated alkyl group having from 1 to 12 carbon atoms, a halogenated alkyloxy group having from 1 to 12 carbon atoms, a halogenated alkylthio group having from 1 to 12 carbon atoms, a halogenated aryloxy group having from 7 to 18 carbon atoms, an aryl group having from 7 to 18 carbon atoms, or a 5-, 6-, 7- or 8-membered heterocyclic group having from 1 to 18 carbon atoms and containing a nitrogen atom, an oxygen atom or a sulfur atom.

$W_1$, $W_2$, $W_3$ and $W_4$ is more preferably an alkylsulfonyl group having from 1 to 12 carbon atoms, an arylsulfonyl group having from 6 to 18 carbon atoms or a sulfamoyl group having from 0 to 12 carbon atoms.

$W_1$, $W_2$, $W_3$ and $W_4$ is still more preferably an alkylsulfonyl group having from 1 to 12 carbon atoms or a sulfamoyl group having from 0 to 12 carbon atoms, and most preferably an alkylsulfonyl group having from 1 to 12 carbon atoms.

At least one of the groups represented by $W_1$, $W_2$, $W_3$ and $W_4$ is an ionic hydrophilic group by itself or has an ionic hydrophilic group as a substituent.

Examples of the ionic hydrophilic group as a substituent include a sulfo group, a carboxyl group, a quaternary ammonium group, an acylsulfamoyl group, a sulfonylcarbamoyl group and a sulfonylsulfamoyl group. Among these, preferred are a carboxyl group, a sulfo group and a sulfonylsulfamoyl group, more preferred is a sulfo group. The counter cation for the ionic hydrophilic group is lithium ion.

l, m, n and p each independently represents an integer of 1 or 2 preferably satisfying $4 \leq l+m+n+p \leq 8$, more preferably $4 \leq l+m+n+p \leq 6$, and most preferably each is 1 ($l=m=n=p=1$).

M represents a hydrogen atom, a metal element, a metal oxide, a metal hydroxide or a metal halide.

M is preferably a hydrogen atom, a metal atom such as Li, Na, K. Mg, Ti, Zr, V, Nb, Ta, Cr, Mo, W, Mn, Fe, Co, Ni, Ru, Rh, Pd, Os, Ir, Pt, Cu, Ag, Au, Zn, Cd, Hg, Al, Ga, In, Si, Ge, Sn, Pb, Sb and Bi, a metal oxide such as VO and GeO, a metal hydroxide such as $Si(OH)_2$, $Cr(OH)_2$ and $Sn(OH)_2$, or a metal halide such as AlCl, $SiCl_2$, VCl, $VCl_2$, VOCl, FeCl, GaCl and ZrCl, more preferably Cu, Ni, An or Al, and most preferably Cu.

In the phthalocyanine compound represented by formula (I), the phthalocyanine ring(Pc) may form a dimer (for example, Pc-M-L-M-Pc) or a trimer through a divalent linking group (L) and the plurality of M's may be the same or different.

The divalent linking group represented by L is preferably an oxy group —O—, a thio group —S—, a carbonyl group —CO—, a sulfonyl group —$SO_2$—, an imino group —NH—, a methylene group —$CH_2$— or a group formed by combining two or more of these groups.

Those substituents $R_1$, $R_2$, $R_3$, $R_4$, $R_5$, $R_6$, $R_7$, $R_8$, $W_1$, $W_2$, $W_3$ and $W_4$ each may further have the following substituent if it is a group which can further have a substituent.

Examples of the substituent which is further substituted include a halogen atom (e.g., chlorine, bromine), a linear or branched alkyl group having from 1 to 12 carbon atoms, an aralkyl group having from 7 to 18 carbon atoms, an alkenyl group having from 2 to 12 carbon atoms, a linear or branched alkynyl group having from 2 to 12 carbon atoms, a cycloalkyl group having from 3 to 12 carbon atoms, which may have a side chain, and a cycloalkenyl group having from 3 to 12 carbon atoms, which may have a side chain, more specifically an alkyl group (e.g., methyl, ethyl, propyl, isopropyl, tert-butyl, 2-methanesulfonylethyl, 3-phenoxypropyl, trifluoromethyl, cyclopentyl), an aryl group (e.g., phenyl, 4-tert-butylphenyl, 2,4-di-tert-amylphenyl), a heterocyclic group (e.g., imidazolyl, pyrazolyl, triazolyl, 2-furyl, 2-thienyl, 2-pyrimidinyl, 2-benzothiazolyl), a cyano group, a hydroxyl group, a nitro group, a carboxy group, an amino group, an alkyloxy group (e.g., methoxy, ethoxy, 2-methoxyethoxy, 2-methanesulfonylethoxy), an aryloxy group (e.g., phenoxy, 2-methylphenoxy, 4-tert-butylphenoxy, 3-nitrophenoxy, 3-tert-butyloxycarbamoylphenoxy, 3-methoxycarbamoyl), an acylamino group (e.g., acetamido, benzamido, 4-(3-tert-butyl-4-hydroxyphenoxy)butanamido), an alkylamino group (e.g., methylamino, butylamino, diethylamino, methylbutyl-amino), an anilino group (e.g., phenylamino, 2-chloro-anilino), a ureido group (e.g., phenylureido, methylureido, N,N-dibutylureido), a sulfamoylamino group (e.g., N,N-dipropylsulfamoylamino), an alkylthio group (e.g., methylthio, octylthio, 2-phenoxyethylthio), an arylthio group (e.g., phenylthio, 2-butoxy-5-tert-octylphenylthio, 2-carboxyphenylthio), an alkyloxycarbonylamino group (e.g., methoxycarbonylamino), a sulfonamido group (e.g., methane-sulfonamido, benzenesulfonamido, p-toluenesulfonamido), a carbamoyl group (e.g., N-ethylcarbamoyl, N,N-dibutyl-carbamoyl), a sulfamoyl group (e.g., N-ethylsulfamoyl, N,N-dipropylsulfamoyl, N,N-diethylsulfamoyl), a sulfonyl group (e.g., methanesulfonyl, octanesulfonyl, benzenesulfonyl, toluenesulfonyl), an alkyloxycarbonyl group (e.g., methoxycarbonyl, butyloxycarbonyl), a heterocyclic oxy group (e.g., 1-phenyltetrazol-5-oxy, 2-tetrahydropyranyloxy), an azo group (e.g., phenylazo, 4-methoxyphenylazo, 4-pivaloylaminophenylazo, 2-hydroxy-4-propanoylphenylazo), an acyloxy group (e.g., acetoxy), a carbamoyloxy group (e.g., N-methylcarbamoyloxy, N-phenylcarbamoyloxy), a silyloxy group (e.g., trimethyl-silyloxy, dibutylmethylsilyloxy), an aryloxycarbonylamino group (e.g., phenoxycarbonylamino), an imido group (e.g., N-succinimido, N-phthalimido), a heterocyclic thio group (e.g., 2-benzothiazolylthio, 2,4-di-phenoxy-1,3,5-triazole-6-thio, 2-pyridylthio), a sulfinyl group (e.g., 3-phenoxy-propylsulfonyl), a phosphonyl group (e.g., phenoxyphosphonyl, octyloxyphosphonyl, phenylphosphonyl), an aryloxycarbonyl group (e.g., phenoxycarbonyl), an acyl group (e.g., acetyl, 3-phenylpropanoyl, benzoyl), an ionic hydrophilic group (e.g., carboxyl, sulfo, quaternary ammonium, sulfonylsulfamoyl, acylsulfamoyl), a cyano group, a hydroxyl group, a nitro group, a carboxyl group and an amino group.

Examples of the halogen atom represented by $R_1$, $R_2$, $R_3$, $R_4$, $R_5$, $R_6$, $R_7$, $R_8$, $W_1$, $W_2$, $W_3$ and $W_4$ include a fluorine atom, a chlorine atom and a bromine atom.

The alkyl group represented by $R_1$, $R_2$, $R_3$, $R_4$, $R_5$, $R_6$, $R_7$, $R_8$, $W_1$, $W_2$, $W_3$ and $W_4$ includes an alkyl group having a substituent and an unsubstituted alkyl group. The alkyl group is preferably an alkyl group having from 1 to 12 carbon atoms excluding the substituent. Examples of the substituent include a hydroxyl group, an alkoxy group, a cyano group, a halogen atom and an ionic hydrophilic group. Examples of the alkyl group include a methyl group, an ethyl group, a butyl group, an isopropyl group, a tert-butyl group, a hydroxyethyl group, a methoxyethyl group, a cyanoethyl group, a trifluoromethyl group, a 3-sulfopropyl group and a 4-sulfobutyl group.

The cycloalkyl group represented by $R_1$, $R_2$, $R_3$, $R_4$, $R_5$, $R_6$, $R_7$, $R_8$, $W_1$, $W_2$, $W_3$ and $W_4$ includes a cycloalkyl group having a substituent and an unsubstituted cycloalkyl group. The cycloalkyl group is preferably a cycloalkyl group having from 5 to 12 carbon atoms excluding the substituent. Examples of the substituent include an ionic hydrophilic group. Examples of the cycloalkyl group include a cyclohexyl group.

The alkenyl group represented by $R_1$, $R_2$, $R_3$, $R_4$, $R_5$, $R_6$, $R_7$, $R_8$, $W_1$, $W_2$, $W_3$ and $W_4$ includes an alkenyl group having a substituent and an unsubstituted alkenyl group. The alkenyl group is preferably an alkenyl group having from 2 to 12 carbon atoms excluding the substituent. Examples of the substituent include an ionic hydrophilic group. Examples of the alkenyl group include a vinyl group and an alkyl group.

The aralkyl group represented by $R_1$, $R_2$, $R_3$, $R_4$, $R_5$, $R_6$, $R_7$, $R_8$, $W_1$, $W_2$, $W_3$ and $W_4$ include an aralkyl group having a substituent and an unsubstituted aralkyl group. The aralkyl group is preferably an aralkyl group having from 7 to 12 carbon atoms excluding the substituent. Examples of the substituent include an ionic hydrophilic group. Examples of the aralkyl group include a benzyl group and a 2-phenethyl group.

The aryl group represented by $R_1$, $R_2$, $R_3$, $R_4$, $R_5$, $R_6$, $R_7$, $R_8$, $W_1$, $W_2$, $W_3$ and $W_4$ includes an aryl group having a substituent and an unsubstituted aryl group. The aryl group is preferably an aryl group having from 6 to 12 carbon atoms excluding the substituent. Examples of the substituent include an alkyl group, an alkoxy group, a halogen atom, an alkylamino group and an ionic hydrophilic group. Examples of the aryl group include a phenyl group, a p-tolyl group, a p-methoxyphenyl group, an o-chlorophenyl group and an m-(3-sulfopropylamino)phenyl group.

The heterocyclic group represented by $R_1$, $R_2$, $R_3$, $R_4$, $R_5$, $R_6$, $R_7$, $R_8$, $W_1$, $W_2$, $W_3$ and $W_4$ includes a heterocyclic group having a substituent and an unsubstituted heterocyclic group. The heterocyclic group may be each independently a saturated heterocyclic ring or an unsaturated heterocyclic ring. Furthermore, the heterocyclic group may each independently form a condensed ring with other ring. The heterocyclic group is preferably a 5- or 6-membered heterocyclic group.

Examples of the heterocyclic group represented by $R_1$, $R_2$, $R_3$, $R_4$, $R_5$, $R_6$, $R_7$, $R_8$, $W_1$, $W_2$, $W_3$ and $W_4$ are shown below in the form of a heterocyclic ring by omitting the substitution site. The substitution site is not limited and for example, pyridine may be substituted at the 2-position, 3-position or 4-position. Examples of the heterocyclic group include pyridine, pyrazine, pyrimidine, pyridazine, triazine, quinoline, isoquinoline, quinazoline, cinnoline, phthalazine, quinoxaline, pyrrole, benzopyrrole, indole, furan, benzofuran, thiophene, benzothiophene, pyrazole, benzopyrazole, imidazole, benzimidazole, triazole, oxazole, benzoxazole, thiazole, benzothiazole, isothiazole, benzisothiazole, thiadiazole, isoxazole, benzisoxazole, pyrrolidine, piperidine, piperazine, imidazolidine and thiazoline. In particular, aromatic heterocyclic groups are preferred. Preferred examples thereof, shown in the same manner as above, include pyridine, pyrazine, pyrimidine, pyridazine, triazine, pyrazole, imidazole, benzimidazole, triazole, thiazole, benzothiazole, isothiazole, benzisothiazole and thiadiazole.

In the case where the heterocyclic group represented by $R_1$, $R_2$, $R_3$, $R_4$, $R_5$, $R_6$, $R_7$, $R_8$, $W_1$, $W_2$, $W_3$ and $W_4$ furthe has a substituent, examples of the substituent include an alkyl group (R—), an alkoxy group (RO—), an alkylamino group (RNH—, RR'N—), a carbamoyl group (—CONHR), a sulfamoyl group (—SO$_2$NHR), a sulfonylamino group (—NHSO$_2$R), a halogen atom and an ionic hydrophilic group (R and R' each represents an alkyl group or a phenyl group and may further have an ionic hydrophilic group).

The alkylamino group represented by $R_1$, $R_2$, $R_3$, $R_4$, $R_5$, $R_6$, $R_7$, $R_8$, $W_1$, $W_2$, $W_3$ and $W_4$ include an alkylamino group having a substituent and an unsubstituted alkylamino group. The alkylamino group is preferably an alkylamino group having from 1 to 6 carbon atoms excluding the substituent. Examples of the substituent include an ionic hydrophilic group. Examples of the alkylamino group include a methylamino group and a diethylamino group.

The alkoxy group represented by $R_1$, $R_2$, $R_3$, $R_4$, $R_5$, $R_6$, $R_7$, $R_8$, $W_1$, $W_2$, $W_3$ and $W_4$ includes an alkoxy group having a substituent and an unsubstituted alkoxy group. The alkoxy group is preferably an alkoxy group having from 1 to 12 carbon atoms excluding the substituent. Examples of the substituent include an alkoxy group, a hydroxyl group and an ionic hydrophilic group. Examples of the alkoxy group include a methoxy group, an ethoxy group, an isopropoxy group, a methoxyethoxy group, a hydroxyethoxy group and a 3-carboxypropoxy group.

The aryloxy group represented by $R_1$, $R_2$, $R_3$, $R_4$, $R_5$, $R_6$, $R_7$, $R_8$, $W_1$, $W_2$, $W_3$ and $W_4$ includes an aryloxy group having a substituent and an unsubstituted aryloxy group. The aryloxy group is preferably an aryloxy group having from 6 to 12 carbon atoms excluding the substituent. Examples of the substituent include an alkoxy group and an ionic hydrophilic group. Examples of the aryloxy group include a phenoxy group, a p-methoxyphenoxy group and an o-methoxyphenoxy group.

The amido group represented by $R_1$, $R_2$, $R_3$, $R_4$, $R_5$, $R_6$, $R_7$, $R_8$, $W_1$, $W_2$, $W_3$ and $W_4$ includes an amido group having a substituent and an unsubstituted amido group. The amido group is preferably an amido group having from 2 to 12 carbon atoms excluding the substituent. Examples of the substituent include an ionic hydrophilic group. Examples of the amido group include an acetamido group, a propionamido group, a benzamido group and a 3,5-disulfobenzamido group.

The arylamino group represented by $R_1$, $R_2$, $R_3$, $R_4$, $R_5$, $R_6$, $R_7$, $R_8$, $W_1$, $W_2$, $W_3$ and $W_4$ includes an arylamino group having a substituent and an unsubstituted arylamino group. The arylamino group is preferably an arylamino group having from 6 to 12 carbon atoms excluding the substituent. Examples of the substituent include a halogen atom and an ionic hydrophilic group. Examples of the arylamino group include an anilino group and a 2-chloroanilino group.

The ureido group represented by $R_1$, $R_2$, $R_3$, $R_4$, $R_5$, $R_6$, $R_7$, $R_8$, $W_1$, $W_2$, $W_3$ and $W_4$ includes a ureido group having a substituent and an unsubstituted ureido group. The ureido group is preferably a ureido group having from 1 to 12 carbon atoms excluding the substituent. Examples of the substituent include an alkyl group and an aryl group. Examples of the ureido group include a 3-methylureido group, a 3,3-dimethylureido group and a 3-phenylureido group.

The sulfamoylamino group represented by $R_1$, $R_2$, $R_3$, $R_4$, $R_5$, $R_6$, $R_7$, $R_8$, $W_1$, $W_2$, $W_3$ and $W_4$ includes a sulfamoylamino group having a substituent and an unsubstituted sulfamoyl-amino group. Examples of the substituent include an alkyl group. Examples of the sulfamoylamino group include an N,N-dipropylsulfamoylamino group.

The alkylthio group represented by $R_1$, $R_2$, $R_3$, $R_4$, $R_5$, $R_6$, $R_7$, $R_8$, $W_1$, $W_2$, $W_3$ and $W_4$ includes an alkylthio group having a substituent and an unsubstituted alkylthio group. The alkylthio group is preferably an alkylthio group having from 1 to 12 carbon atoms excluding the substituent. Examples of the substituent include an ionic hydrophilic group. Examples of the alkylthio group include a methylthio group and an ethylthio group.

The arylthio group represented by $R_1$, $R_2$, $R_3$, $R_4$, $R_5$, $R_6$, $R_7$, $R_8$, $W_1$, $W_2$, $W_3$ and $W_4$ includes an arylthio group having a substituent and an unsubstituted arylthio group. The arylthio group is preferably an arylthio group having from 6 to 12 carbon atoms excluding the substituent. Examples of the substituent include an alkyl group and an ionic hydrophilic group. Examples of the arylthio group include a phenylthio group and a p-tolylthio group.

The alkoxycarbonylamino group represented by $R_1$, $R_2$, $R_3$, $R_4$, $R_5$, $R_6$, $R_7$, $R_8$, $W_1$, $W_2$, $W_3$ and $W_4$ includes an alkoxycarbonylamino group having a substituent and an unsubstituted alkoxycarbonylamino group. The alkoxy-carbonylamino group is preferably an alkoxycarbonylamino group having from 2 to 12 carbon atoms excluding the substituent. Examples of the substituent include an ionic hydrophilic group. Examples of the alkoxycarbonylamino group include an ethoxycarbonylamino group.

The sulfonamido group represented by $R_1$, $R_2$, $R_3$, $R_4$, $R_5$, $R_6$, $R_7$, $R_8$, $W_1$, $W_2$, $W_3$ and $W_4$ includes a sulfonamido group having a substituent and an unsubstituted sulfonamido group. The sulfonamido group is preferably an sulfonamido group having from 1 to 12 carbon atoms excluding the substituent. Examples of the substituent include an ionic hydrophilic group. Examples of the sulfonamido group include methanesulfonamido, benzenesulfonamido and 3-carboxybenzenesulfonamido.

The carbamoyl group represented by $R_1$, $R_2$, $R_3$, $R_4$, $R_5$, $R_6$, $R_7$, $R_8$, $W_1$, $W_2$, $W_3$ and $W_4$ includes a carbamoyl group having a substituent and an unsubstituted carbamoyl group. Examples of the substituent include an alkyl group. Examples of the carbamoyl group include a methylcarbamoyl group and a dimethylcarbamoyl group.

The sulfamoyl group represented by $R_1$, $R_2$, $R_3$, $R_4$, $R_5$, $R_6$, $R_7$, $R_8$, $W_1$, $W_2$, $W_3$ and $W_4$ includes a sulfamoyl group having a substituent and an unsubstituted sulfamoyl group. Examples of the substituent include an alkyl group and an aryl group. Examples of the sulfamoyl group include a dimethylsulfamoyl group, a di-(2-hydroxyethyl) sulfamoyl group and a phenylsulfamoyl group.

The sulfonyl group represented by $R_1$, $R_2$, $R_3$, $R_4$, $R_5$, $R_6$, $R_7$, $R_8$, $W_1$, $W_2$, $W_3$ and $W_4$ includes a sulfonyl group having a substituent and an unsubstituted sulfonyl group. Examples of the substituent include an alkyl group and an aryl group. Examples of the sulfonyl group include a methanesulfonyl group and a phenylsulfonyl group.

The alkoxycarbonyl group represented by $R_1$, $R_2$, $R_3$, $R_4$, $R_5$, $R_6$, $R_7$, $R_8$, $W_1$, $W_2$, $W_3$ and $W_4$ includes an alkoxycarbonyl group having a substituent and an unsubstituted alkoxycarbonyl group. The alkoxycarbonyl group is preferably an alkoxycarbonyl group having from 2 to 12 carbon atoms excluding the substituent. Examples of the substituent include an ionic hydrophilic group. Examples of the alkoxycarbonyl group include a methoxycarbonyl group and an ethoxycarbonyl group.

The heterocyclic oxy group represented by $R_1$, $R_2$, $R_3$, $R_4$, $R_5$, $R_6$, $R_7$, $R_8$, $W_1$, $W_2$, $W_3$ and $W_4$ includes a heterocyclic oxy group having a substituent and an unsubstituted heterocyclic oxy group. The heterocyclic oxy group is preferably a heterocyclic oxy group having a 5- or 6-membered heterocyclic ring. Examples of the substituent include a hydroxyl group and an ionic hydrophilic group. Examples of the heterocyclic oxy group include a 2-tetrahydropyranyloxy group.

The azo group represented by $R_1$, $R_2$, $R_3$, $R_4$, $R_5$, $R_6$, $R_7$, $R_8$, $W_1$, $W_2$, $W_3$ and $W_4$ includes an azo group having a substituent and an unsubstituted azo group. Examples of the azo group include a p-nitrophenylazo group.

The acyloxy group represented by $R_1$, $R_2$, $R_3$, $R_4$, $R_5$, $R_6$, $R_7$, $R_8$, $W_1$, $W_2$, $W_3$ and $W_4$ includes an acyloxy group having a substituent and an unsubstituted acyloxy group. The acyloxy group is preferably an acyloxy group having from 1 to 12 carbon atoms excluding the substituent. Examples of the substituent include an ionic hydrophilic group. Examples of the acyloxy group include an acetoxy group and a benzoyloxy group.

The carbamoyloxy group represented by $R_1$, $R_2$, $R_3$, $R_4$, $R_5$, $R_6$, $R_7$, $R_8$, $W_1$, $W_2$, $W_3$ and $W_4$ includes a carbamoyloxy group having a substituent and an unsubstituted carbamoyloxy group. Examples of the substituent include an alkyl group. Examples of the carbamoyloxy group include an N-methylcarbamoyloxy group.

The silyloxy group represented by $R_1$, $R_2$, $R_3$, $R_4$, $R_5$, $R_6$, $R_7$, $R_8$, $W_1$, $W_2$, $W_3$ and $W_4$ includes a silyloxy group having a substituent and an unsubstituted silyloxy group. Examples of the substituent include an alkyl group. Examples of the silyloxy group include a trimethylsilyloxy group.

The aryloxycarbonyl group represented by $R_1$, $R_2$, $R_3$, $R_4$, $R_5$, $R_6$, $R_7$, $R_8$, $W_1$, $W_2$, $W_3$ and $W_4$ includes an aryloxycarbonyl group having a substituent and an unsubstituted aryloxycarbonyl group. The aryloxycarbonyl group is preferably an aryloxycarbonyl group having from 7 to 12 carbon atoms excluding the substituent. Examples of the substituent include an ionic hydrophilic group. Examples of the aryloxycarbonyl group include a phenoxycarbonyl group.

The aryloxycarbonylamino group represented by $R_1$, $R_2$, $R_3$, $R_4$, $R_5$, $R_6$, $R_7$, $R_8$, $W_1$, $W_2$, $W_3$ and $W_4$ includes an aryloxycarbonylamino group having a substituent and an unsubstituted aryloxycarbonylamino group. The aryloxycarbonylamino group is preferably an aryloxycarbonylamino group having from 7 to 12 carbon atoms excluding the substituent. Examples of the substituent include an ionic hydrophilic group. Examples of the aryloxycarbonylamino group include a phenoxycarbonylamino group.

The imido group represented by $R_1$, $R_2$, $R_3$, $R_4$, $R_5$, $R_6$, $R_7$, $R_8$, $W_1$, $W_2$, $W_3$ and $W_4$ includes an imido group having a substituent and an unsubstituted imido group. Examples of the imido group include an N-phthalimido group and an N-succinimido group.

The heterocyclic thio group represented by $R_1$, $R_2$, $R_3$, $R_4$, $R_5$, $R_6$, $R_7$, $R_8$, $W_1$, $W_2$, $W_3$ and $W_4$ includes a heterocyclic thio group having a substituent and an unsubstituted heterocyclic thio group. The heterocyclic thio group preferably has a 5- or 6-membered heterocyclic ring. Examples of the substituent include an ionic hydrophilic group. Examples of the heterocyclic thio group include a 2-pyridylthio group.

The sulfinyl group represented by $R_1$, $R_2$, $R_3$, $R_4$, $R_5$, $R_6$, $R_7$, $R_8$, $W_1$, $W_2$, $W_3$ and $W_4$ includes a sulfinyl group having a substituent and an unsubstituted sulfinyl group. Examples of the substituent include an alkyl group and an aryl group. Examples of the sulfinyl group include a phenylsulfinyl group.

The phosphoryl group represented by $R_1$, $R_2$, $R_3$, $R_4$, $R_5$, $R_6$, $R_7$, $R_8$, $W_1$, $W_2$, $W_3$ and $W_4$ includes a phosphoryl group having a substituent and an unsubstituted phosphoryl group. Examples of the phosphoryl group include a phenoxyphosphoryl group and a phenylphosphoryl group.

The acyl group represented by $R_1$, $R_2$, $R_3$, $R_4$, $R_5$, $R_6$, $R_7$, $R_8$, $W_1$, $W_2$, $W_3$ and $W_4$ includes an acyl group having a substituent and an unsubstituted acyl group. The acyl group is preferably an acyl group having from 1 to 12 carbon atoms. Examples of the substituent include an ionic hydrophilic group. Examples of the acyl group include an acetyl group and a benzoyl group.

The sulfonylsulfamoyl group represented by $W_1$, $W_2$, $W_3$ and $W_4$ includes a sulfonylsulfamoyl group having a substituent and an unsubstituted sulfonylsulfamoyl group. The sulfonylsulfamoyl group is preferably a sulfonyl-sulfamoyl group having from 1 to 12 carbon atoms excluding the substituent. Examples of the substituent include an ionic hydrophilic group. Examples of the sulfonylsulfamoyl group include a methanesulfonylsulfamoyl group and a benzenesulfonylsulfamoyl group.

The acylsulfamoyl group represented by $W_1$, $W_2$, $W_3$ and $W_4$ includes an acylsulfamoyl group having a substituent and an unsubstituted acylsulfamoyl group. The acylsulfamoyl group is preferably an acylsulfamoyl group having from 1 to 12 carbon atoms excluding the substituent. Examples of the substituent include an ionic hydrophilic group. Examples of the acylsulfamoyl group include an acetylsulfamoyl group and a benzoylsulfamoyl group.

In the phthalocyanine compound represented by formula (I), the following combination is particularly preferred.

(i) $R_1$, $R_2$, $R_3$, $R_4$, $R_5$, $R_6$, $R_7$ and $R_8$ each is independently a hydrogen atom, a halogen atom or a cyano group, more preferably a hydrogen atom or a halogen atom, and most preferably a hydrogen atom.

(ii) $W_1$, W2, $W_3$ and $W_4$ each is a sulfamoyl, sulfonyl, sulfinyl, sulfonylsulfamoyl or acylsulfamoyl group having a substituent, and most preferably a sulfamoyl group or a sulfonyl group. Furthermore, at least one of $W_1$, $W_2$, $W_3$ and $W_4$ has an ionic hydrophilic group as the substituent. In particular, most preferred is the case where $W_1$, $W_2$, $W_3$ and $W_4$ each independently has an ionic hydrophilic group as the substituent. The ionic hydrophilic group as the substituent is a sulfo group, a carboxyl group, a quaternary ammonium group, a sulfonylsulfamoyl group or an acylsulfamoyl group, more preferably a sulfo group, a sulfonylsulfamoyl group or an acylsulfamoyl group, still more preferably a sulfo group. The counter cation of the ionic hydrophilic group is lithium ion.

(iii) l, m, n and p each is independently an integer of 1 or 2, more preferably 1.

(iv) M is a hydrogen atom, a metal element, a metal oxide, a metal hydroxide or a metal halide, more preferably Cut Ni, Zn or Al, and most preferably Cu.

The phthalocyanine compound represented by formula (I) has at least one or more ionic hydrophilic group within the molecule and therefore, exhibits good solubility or dispersibility in an aqueous medium.

From this viewpoint, the phthalocyanine compound represented by formula (I) preferably has at least four or more ionic hydrophilic groups within one molecule and at least one of the plurality of ionic hydrophilic groups is preferably a sulfo group. In particular, a phthalocyanine compound having at least four or more sulfo groups within one molecule is most preferred.

As for the combination of preferred substituents in the compound represented by formula (I), a compound where at least one of various substituents is the preferred group is preferred, and a compound where all substituents are the preferred groups is most preferred.

Among the phthalocyanine compounds represented by formula (I), a phthalocyanine compound having a structure represented by the following formula (II) or (III) is preferred. The phthalocyanine compound represented by formula (II) or (III) of the present invention is described in detail below.

Formula (II):

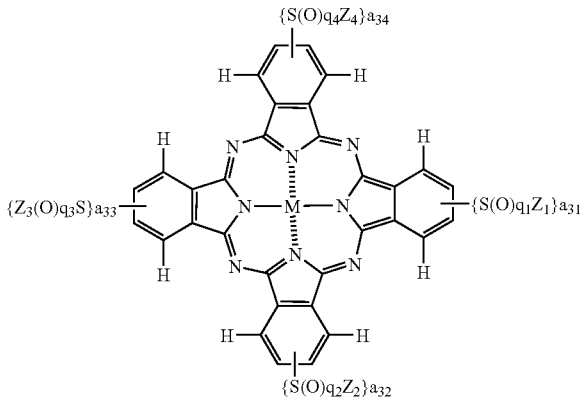

Formula (III):

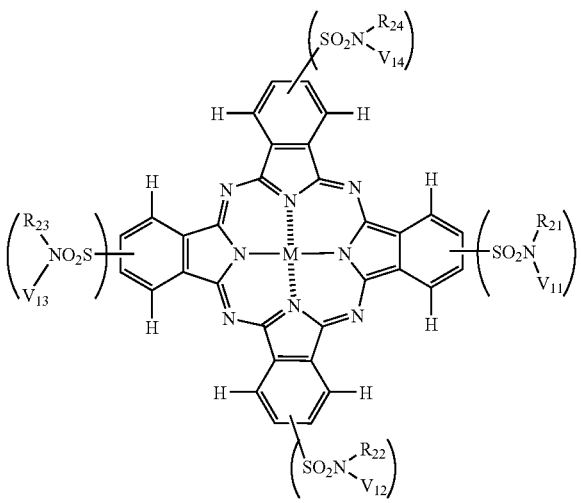

Formula (II) is described below. $Z_1$, $Z_2$, $Z_3$ and $Z_4$ each independently represents a substituted or unsubstituted alkyl group, a substituted or unsubstituted cyclo-alkyl group, a substituted or unsubstituted alkenyl group, a substituted or unsubstituted aralkyl group, a substituted or unsubstituted aryl group or a substituted or unsubstituted heterocyclic group, preferably a substituted alkyl group, a substituted aryl group or a substituted heterocyclic group, most preferably a substituted alkyl group.

The alkyl group represented by $Z_1$, $Z_2$, $Z_3$ and $Z_4$ has the same meaning as the alkyl group represented by $R_1$ to $R_8$ and $W_1$ to $W_4$ of formula (I).

The cycloalkyl group represented by $Z_1$, $Z_2$, $Z_3$ and $Z_4$ has the same meaning as the cycloalkyl group represented by $R_1$ to $R_8$ and $W_1$ to $W_4$ of formula (I).

The alkenyl group represented by $Z_1$, $Z_2$, $Z_3$ and $Z_4$ has the same meaning as the alkenyl group represented by $R_1$ to $R_8$ and $W_1$ to $W_4$ of formula (I).

The aralkyl group represented by $Z_1$, $Z_2$, $Z_3$ and $Z_4$ has the same meaning as the aralkyl group represented by $R_1$ to $R_8$ and $W_1$ to $W_4$ of formula (I).

The aryl group represented by $Z_1$, $Z_2$, $Z_3$ and $Z_4$ has the same meaning as the aryl group represented by $R_1$ to $R_8$ and $W_1$ to $W_4$ of formula (I).

The heterocyclic group represented by $Z_1$, $Z_2$, $Z_3$ and $Z_4$ has the same meaning as the heterocyclic group represented by $R_1$ to $R_8$ and $W_1$ to $W_4$ of formula (I).

$q_1$, $q_2$, $q_3$ and $q_4$ each independently represents an integer of 1 or 2, preferably 2, most preferably $q_1=q_2=q_3=q_4=2$.

$a_{31}$, $a_{32}$, $a_{33}$ and $a_{34}$ each independently represents an integer of 1 or 2, preferably 1, most preferably $a_{31}=a_{32}=a_{33}=a_{34}=1$.

M has the same meaning as M in formula (I).

At least one of $Z_1$, $Z_2$, $Z_3$ and $Z_4$ has an ionic hydrophilic group as a substituent.

Examples of the ionic hydrophilic group are the same as examples of the ionic hydrophilic group in formula (I), and preferred examples are also the same.

The molecular weight of the phthalocyanine compound of the present invention is preferably from 750 to 2,500, more preferably from 995 to 2,500, still more preferably from 995 to 2,000, particularly preferably from 995 to 1,800.

Formula (III) is described below. $R_{21}$, $R_{22}$, $R_{23}$ and $R_{24}$ each independently represents a hydrogen atom, a substituted or unsubstituted alkyl group, a substituted or unsubstituted cycloalkyl group, a substituted or unsubstituted alkenyl group, a substituted or unsubstituted aralkyl group, a substituted or unsubstituted aryl group or a substituted or unsubstituted heterocyclic group, preferably a hydrogen atom, a substituted alkyl group, a substituted aryl group or a substituted heterocyclic group, more preferably a hydrogen atom or a substituted alkyl group, and most preferably a hydrogen atom.

$V_{11}$, $V_{12}$, $V_{13}$ and $V_{14}$ each independently represents a substituted or unsubstituted alkyl group, a substituted or unsubstituted cycloalkyl group, a substituted or unsubstituted alkenyl group, a substituted or unsubstituted aralkyl group, a substituted or unsubstituted aryl group, or a substituted or unsubstituted heterocyclic group, preferably a substituted alkyl group, a substituted aryl group or a substituted heterocyclic group, most preferably a substituted alkyl group.

The alkyl group represented by $R_{21}$, $R_{22}$, $R_{23}$, $R_{24}$, $V_{11}$, $V_{12}$, $V_{13}$ and $V_{14}$ has the same meaning as the alkyl group represented by $R_1$ to $R_8$ and $W_1$ to $W_4$ of formula (I).

The cycloalkyl group represented by $R_{21}$, $R_{22}$, $R_{23}$, $R_{24}$, $V_{11}$, $V_{12}$, $V_{13}$ and $V_{14}$ has the same meaning as the cycloalkyl group represented by $R_1$ to $R_8$ and $W_1$ to $W_4$ of formula (I).

The alkenyl group represented by $R_{21}$, $R_{22}$, $R_{23}$, $R_{24}$, $V_{11}$, $V_{12}$, $V_{13}$ and $V_{14}$ has the same meaning as the alkenyl group represented by $R_1$ to $R_8$ and $W_1$ to $W_4$ of formula (I).

The aralkyl group represented by $R_{21}$, $R_{22}$, $R_{23}$, $R_{24}$, $V_{11}$, $V_{12}$, $V_{13}$ and $V_{14}$ has the same meaning as the aralkyl group represented by $R_1$ to $R_8$ and $W_1$ to $W_4$ of formula (I).

The aryl group represented by $R_{21}$, $R_{22}$, $R_{23}$, $R_{24}$, $V_{11}$, $V_{12}$, $V_{13}$ and $V_{14}$ has the same meaning as the aryl group represented by $R_1$ to $R_8$ and $W_1$ to $W_4$ of formula (I).

The heterocyclic group represented by $R_{21}$, $R_{22}$, $R_{23}$, $R_{24}$, $V_{11}$, $V_{12}$, $V_{13}$ and $V_4$ has the same meaning as the heterocyclic group represented by $R_1$ to $R_8$ and $W_1$ to $W_4$ of formula (I).

The heterocyclic ring or a condensed ring thereof represented by $R_{21}$, $R_{22}$, $R_{23}$, $R_{24}$, $V_{11}$, $V_{12}$, $V_{13}$ and $V_{14}$ is preferably a 5- or 6-membered nitrogen-containing heterocyclic ring (which may further form a condensed ring with other ring), provided that when $R_{21}$, $R_{22}$, $R_{23}$, $R_{24}$, $V_{11}$, $V_{12}$, $V_{13}$ and $V_{14}$ each independently forms a 6-membered nitrogen-containing heterocyclic ring (which may further form a condensed ring with other ring), the number of nitrogen atom constituting the 6-membered nitrogen-containing heterocyclic ring is 1 or 2 (the case where the number of nitrogen atoms constituting the 6-membered nitrogen-containing heterocyclic ring is 3 or more, for example, a triazine ring, is excluded).

Examples of the heterocyclic group represented by $R_{21}$, $R_{22}$, $R_{23}$, $R_{24}$, $V_{11}$, $V_{12}$, $V_{13}$ and $V_{14}$ are the same as examples of the heterocyclic group in formula (I), and preferred examples are also the same.

In the case where the heterocyclic group represented by $R_{21}$, $R_{22}$, $R_{23}$, $R_{24}$, $V_{11}$, $V_{12}$, $V_{13}$ and $V_{14}$ further has a substituent, examples of the substituent are the same as examples of the substituent in formula (I), and preferred examples are also the same.

M has the same meaning as M in formula (I), and preferred examples are also the same.

At least one of $R_{21}$, $R_{22}$, $R_{23}$, $R_{24}$, $V_{11}$, $V_{12}$, $V_{13}$ and $V_{14}$ has an ionic hydrophilic group as the substituent.

Examples of the ionic hydrophilic group and the molecular weight of the phthalocyanine compound are the same as those described above for formula (II).

The phthalocyanine compounds represented by formulae (II) and (III) each has at least one ionic hydrophilic group within one molecule or have at least one ionic hydrophilic group as the substituent and therefore, exhibits good solubility or dispersibility in an aqueous medium. From this viewpoint, the phthalocyanine compounds represented by formulae (II) and (III) each preferably has at least two or more ionic hydrophilic groups within one molecule and at least one of the plurality of ionic hydrophilic groups is preferably a sulfo group. In particular, a phthalocyanine compound having at least two or more sulfo groups within one molecule is most preferred.

The phthalocyanine compound represented by formula (II) is preferably a compound having a combination of the following (i) to (vi).

(i) $Z_1$ to $Z_4$ each independently represents a substituted or unsubstituted alkyl group, a substituted or unsubstituted cycloalkyl group, a substituted or unsubstituted alkenyl group, a substituted or unsubstituted aralkyl group, a substituted or unsubstituted aryl group, or a substituted or unsubstituted heterocyclic group, more preferably a substituted alkyl group, a substituted aryl group or a substituted heterocyclic group, still more preferably a substituted alkyl group, and most preferably an alkyl group having an ionic hydrophilic group as the substituent.

(ii) $q_1$, $q_2$, $q_3$ and $q_4$ each independently represents an integer of 1 or 2, more preferably 2, most preferably $q_1=q_2=q_3=q_4=2$.

(iii) $a_{31}$, $a_{32}$, $a_{33}$ and $a_{34}$ each independently represents an integer of 1 or 2, more preferably 1, most preferably $a_{31}=a_{32}=a_{33}=a_{34}=1$.

(iv) M is preferably Cu, Ni, Zn or Al, most preferably Cu.

(v) The molecular weight of the phthalocyanine compound is preferably from 750 to 2,500, more preferably from 995 to 2,500, still more preferably from 995 to 2,000, and most preferably from 995 to 1,800.

(vi) The phthalocyanine compound represented by formula (II) has at least one or more ionic hydrophilic group within the molecule and therefore, exhibits good solubility or dispersibility in an aqueous medium. From this viewpoint, the phthalocyanine compound represented by formula (II) preferably has at least two or more ionic hydrophilic groups within one molecule and at least one of the plurality of ionic hydrophilic groups is preferably a sulfo group. In particular, a phthalocyanine compound having at least two or more sulfo groups within one molecule is most preferred.

As for the combination of preferred substituents in the compound represented by formula (II), a compound where at least one of various substituents is the preferred group is preferred, a compound where a larger number of various substituents are the preferred groups is more preferred, and a compound where all substituents are the preferred groups is most preferred.

The phthalocyanine compound represented by formula (III) is preferably a compound having a combination of the following (i) to (v).

(i) $R_{21}$, $R_{22}$, $R_{23}$ and $R_{24}$ each independently represents a hydrogen atom, a substituted or unsubstituted alkyl group, a substituted or unsubstituted cycloalkyl group, a substituted or unsubstituted alkenyl group, a substituted or unsubstituted aralkyl group, a substituted or unsubstituted aryl group, or a substituted or unsubstituted heterocyclic group, more preferably a hydrogen atom, a substituted alkyl group, a substituted aryl group or a substituted heterocyclic group, and most preferably a hydrogen atom.

(ii) $V_{11}$, $V_{12}$, $V_{13}$ and $V_{14}$ each independently represents a substituted or unsubstituted alkyl group, a substituted or unsubstituted cycloalkyl group, a substituted or unsubstituted alkenyl group, a substituted or unsubstituted aralkyl group, a substituted or unsubstituted aryl group, or a substituted or unsubstituted heterocyclic group, more preferably a substituted alkyl group, a substituted aryl group or a substituted heterocyclic group, and most preferably an alkyl group having an ionic hydrophilic group as the substituent.

(iii) M is preferably Cu, Ni, Zn or Al, most preferably Cu.

(iii) The molecular weight of the phthalocyanine compound is preferably from 750 to 2,500, more preferably from 995 to 2,500, still more preferably from 995 to 2,000, and most preferably from 995 to 1,800.

(v) The phthalocyanine compound represented by formula (III) has at least one or more ionic hydrophilic group within the molecule and therefore, exhibits good solubility or dispersibility in an aqueous medium. From this viewpoint, the phthalocyanine compound represented by formula (III) preferably has at least two or more ionic hydrophilic groups within one molecule and at least one of the plurality of ionic hydrophilic groups is preferably a sulfo group. In particular, a phthalocyanine compound having at least two or more sulfo groups within one molecule is most preferred.

As for the combination of preferred substituents in the compound represented by formula (III), a compound where at least one of various substituents is the preferred group is preferred, a compound where a larger number of various substituents are the preferred groups is more preferred, and a compound where all substituents are the preferred groups is most preferred.

The phthalocyanine compound of the present invention is particularly preferably the compound represented by formula (II) where $q_1=q_2=q_3=q_4=2$, namely, the substituent is a sulfonyl group.

The phthalocyanine compound represented by formula (IV) of the present invention is described in detail below.

Phthalocyanine derivatives conventionally used are a mixture of isomers different in the site to which a specific substituent is introduced (depending on the case, the number of sites to which introduced). The compound (the compound represented by formula (IV); a phthalocyanine derivative having a specific structure where specific substituents each in a specific number are selectively introduced into specific sites) of the present invention is a novel compound having a specific structure which has heretofore not been isolated and recognized. By virtue of the performance brought out from the specific structure, this compound is very useful as a water-soluble dye for ink jetting, imparted with high functionality or as an intermediate for the synthesis of the water-soluble dye (a system comprising a mixture of isomers each having a substituent introduced into a specific site, namely, conventional phthalocyanine derivatives, cannot exert the objective performance of high level), and can be a useful intermediate for chemical, medical or agricultural organic compounds.

Formula (IV):

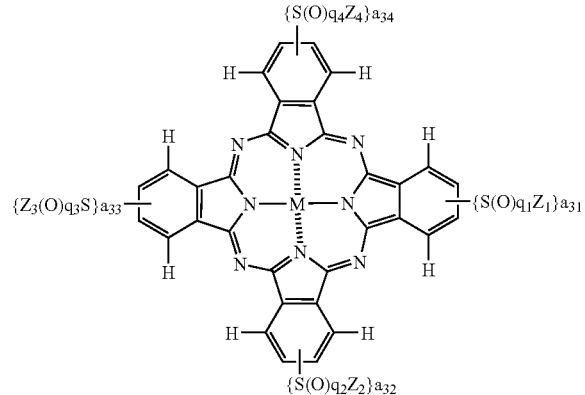

Formula (IV) is described below.

$Z_1$, $Z_2$, $Z_3$ and $Z_4$ have the same meanings as $Z_1$, $Z_2$, $Z_3$ and $Z_4$ in formula (II), and preferred examples thereof are also the same.

$q_1$, $q_2$, $q_3$ and $q_4$ each independently represents an integer of 1 or 2, preferably 2, and most preferably $q_1=q_2=q_3=q_4=2$.

$a_{31}$, $a_{32}$, $a_{33}$ and $a_{34}$ each independently represents an integer of 1 or 2, preferably 2, and most preferably $a_{31}=a_{32}=a_{33}=a_{34}=1$.

M has the same meaning as M in formula (II), and preferred examples thereof are also the same.

At least one of $Z_1$, $Z_2$, $Z_3$ and $Z_4$ has an ionic hydrophilic group as a substituent.

Examples of the ionic hydrophilic group are the same as examples of the ionic hydrophilic group in formula (II), and preferred examples thereof are also the same.

The molecular weight of the phthalocyanine compound represented by formula (IV) is preferably from 750 to 2,500, more preferably from 995 to 2,500, still more preferably from 995 to 2,000, particularly preferably from 995 to 1,800.

In general, it is known to use various phthalocyanine derivatives as an ink composition for ink jetting. The phthalocyanine derivative represented by the following formula (V) sometimes contains an isomer with respect to the substitution site of the substituent $R_n$ (n=1 to 16, R simply means a substituent and it is not intended that $R_n$ all are the same substituent) (here, $R_1$ to $R_{16}$ are defined as substituents at the 1-position to the 16-position, respectively), which inevitably occurs at the time of synthesis, however, these substitution site isomers are not distinguished from each other but regarded as the same derivative in many cases. Also, in the case where the substituent R contains an isomer, these are not distinguished but regarded as the same phthalocyanine derivative in many cases.

Formula (V):

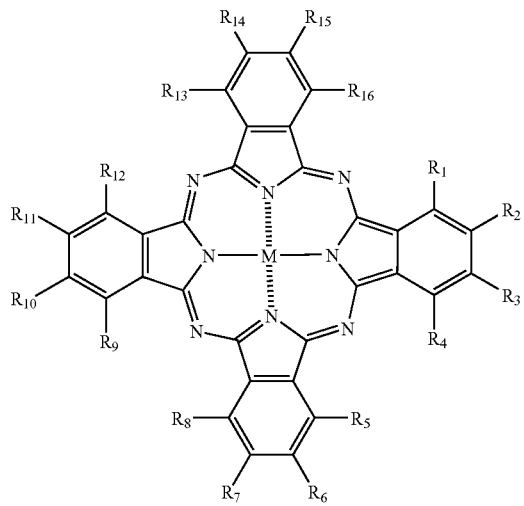

The meaning that in the phthalocyanine compound of the present invention, the structure is different is described by referring to formula (V). With respect to the substituent $R_n$ (n=1 to 16), when the constituent atom species is different, this means that the number of substituents is different or that the substitution site is different.

In the present invention, derivatives where the structure of the phthalocyanine compound represented by formula (I) is different (particularly, in the substitution site) are defined by classifying these into the following three types.

(1) β-Position Substitution Type:
(a phthalocyanine compound having specific substituents at the 2- and/or 3-position, the 6- and/or 7-position, the 10- and/or 11-position, and the 14- and/or 15-position)

(2) α-Position Substitution Type:
(a phthalocyanine compound having specific substituents at the 1- and/or 4-position, the 5- and/or 8-position, the 9- and/or 12-position, and the 13- and/or 16-position)

(3) α,β-Position Mixed Substitution Type:
(a phthalocyanine compound having specific substitutions at the 1- to 16-position without any regularity)

In the present invention, phthalocyanine compound derivatives different in the structure (particularly, in the substitution site) are described by using these β-position substitution type, α-position substitution type and α,β-position mixed substitution type.

The phthalocyanine derivative for use in the present invention can be synthesized by combining the methods described or cited, for example, in Shirai and Kobayashi, *Phthalocyanine—Kagaku to Kino—(Phthalocyanine—Chemistry and Function—)*, pp. 1–62, IBC, and C. C. Leznoff and A. B. P. Lever, *Phthalocyanines—Properties and Applications*, pp. 1–54, VCH, or methods analogous thereto.

Phthalocyanine compounds heretofore reported can be synthesized, for example, through sulfonation, sulfonyl chloridation or amidation of an unsubstituted phthalocyanine compound as described in International Patents 00/17275, 00/08103, 00/08101 and 98/41853 and JP-A-10-36471.

In this case, (1) sulfonation takes place at any site of the phthalocyanine nucleus and (2) the number of sites sulfonated is difficult to control.

Accordingly, when a sulfo group is introduced under such reaction conditions, the site and number of sulfo groups introduced into the product cannot be specified and a mixture of those different in the number of substituents or in the substitution site inevitably results.

If a phthalocyanine compound is synthesized starting from such a product, the compound is obtained as a mixture containing several kinds of compounds different in the number of substituents or in the substitution site because the number of sulfamoyl groups substituted or their substitution sites cannot be specified.

On the other hand, out of the phthalocyanine compounds represented by formulae (I) to (IV) of the present invention, for example, the phthalocyanine compound represented by formula (X) can be synthesized by reacting a phthalonitrile derivative represented by the following formula (VI) and/or a diiminoisoindoline derivative represented by the following formula (VII) with a metal derivative represented by the following formula (VIII).

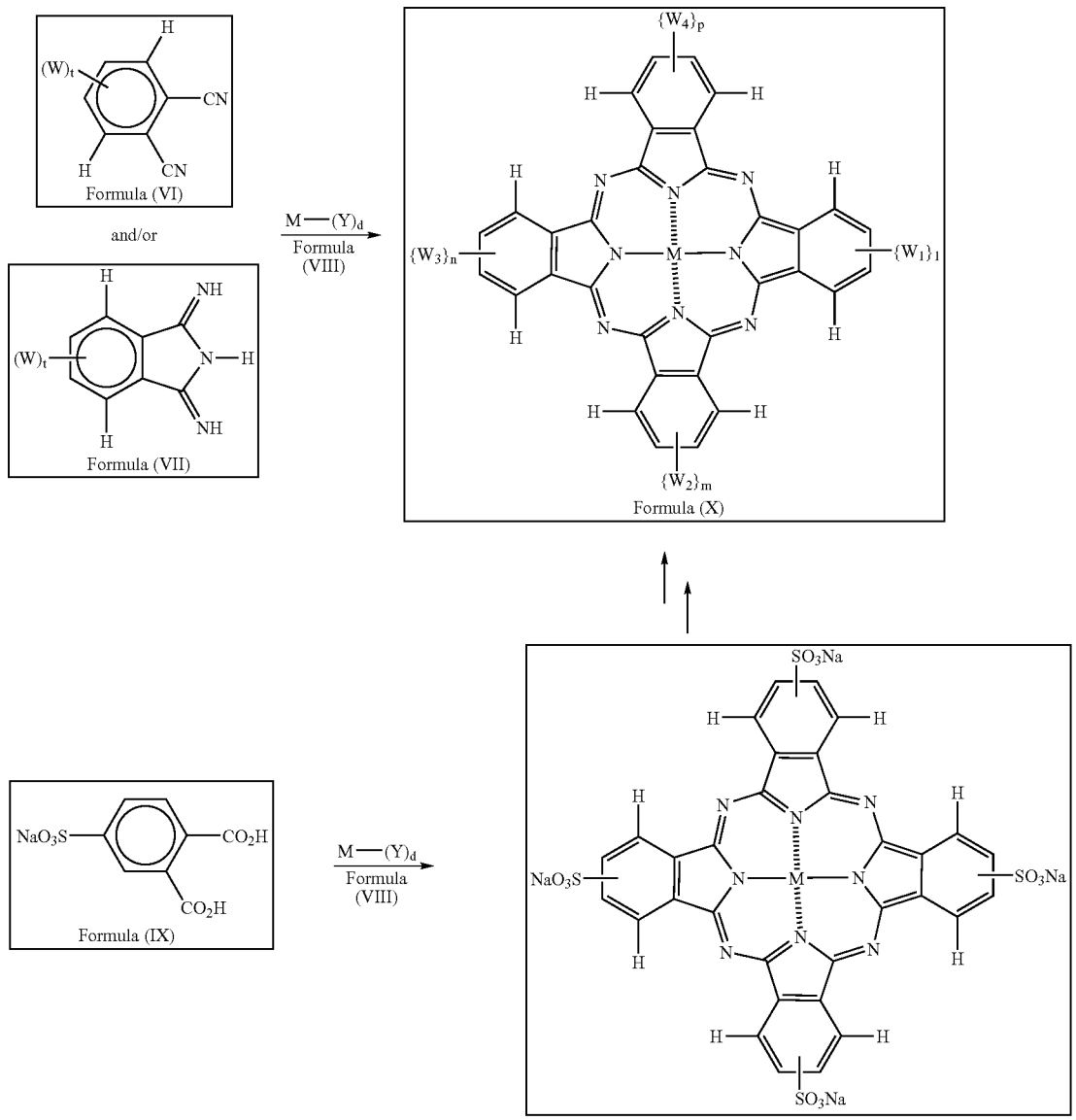

Also, the phthalocyanine compound represented by formula (III) of the present invention can be synthesized by reacting a sodium 4-sulfophthalate represented by formula (IX) and a metal derivative represented by formula (VIII) to obtain phthalocyanine copper(II)-tetrasodium tetrasulfonate, deriving a corresponding sulfonyl chloride therefrom and reacting it with an objective amine or aniline derivative (for example, when $W_1$, $W_2$, $W_3$ and $W_4$ are $W_1$: {—$SO_2$N ($R_{21}$) ($V_{11}$)}, $W_2$: {—$SO_2$N ($R_{22}$) ($V_{12}$)}, $W_3$: {—$SO_2$N ($R_{23}$) ($V_{13}$)} and $W_4$: {—$SO_2$N($R_{24}$) ($V_{14}$)}).

In formula (VI) and/or formula (VII), t has the same meaning as l, m, n and p in formula (I). In formula (X), $W_1$, $W_2$, $W_3$ and $W_4$ each independently represents $W_1$: {—S(O)$q_1$-$Z_1$}, $W_2$: {—S(O)$q_2$-$Z_2$}, $W_3$: {—S(O)$q_3$-$Z_3$} and $W_4$: {—S(O)$q_4$-$Z_4$} in formula (II), and/or $W_1$: {—$SO_2$N ($R_{21}$) ($V_{11}$)}, $W_2$: {—$SO_2$N($R_{22}$) ($V_{12}$)}, $W_3$: {—$SO_2$N ($R_{23}$) ($V_{13}$)} and $W_4$: {—$SO_2$N($R_{24}$) ($V_{14}$)} in formula (III).

Formula (VIII):

$$M\text{-}(Y)_d$$

wherein M has the same meaning as M in formulae (I) to (IV), Y represents a monovalent or divalent ligand such as halogen atom, acetate anion, acetyl acetonate and oxygen, and d represents an integer of 1 to 4.

Examples of the metal derivative represented by formula (VIII) include a halide, a carboxylic acid derivative, a sulfate, a nitrate, a carbonyl compound, an oxide and a complex of Al, Si, Ti, V, Mn, Fe, Co, Ni, Cu, Zn, Ge, Ru, Rh, Pd, In, Sn, Pt and Pb. Specific examples thereof include copper chloride, copper bromide, copper iodide, nickel chloride, nickel bromide, nickel acetate, cobalt chloride, cobalt bromide, cobalt acetate, iron chloride, zinc chloride, zinc bromide, zinc iodide, zinc acetate, vanadium chloride, vanadium oxytrichloride, palladium chloride, palladium acetate, aluminum chloride, manganese chloride, manganese acetate, acetylacetone manganese, lead chloride, lead acetate, indium chloride, titanium chloride and tin chloride.

The amounts of the metal derivative and the phthalonitrile compound represented by formula (VI) used are preferably, in terms of the molar ratio, from 1:3 to 1:6.

The amounts of the metal derivative and the diiminoisoindoline derivative represented by formula (VII) are preferably, in terms of the molar ratio, from 1:3 to 1:6.

The reaction is usually performed in the presence of a solvent. For the solvent, an organic solvent having a boiling point of 80° C. or more, preferably 130° C. or more is used. Examples thereof include n-amyl alcohol, n-hexanol, cyclohexanol, 2-methyl-1-pentanol, 1-heptanol, 2-heptanol, 1-octanol, 2-ethylhexanol, benzyl alcohol, ethylene glycol, propylene glycol, ethoxyethanol, propoxyethanol, butoxyethanol, dimethylaminoethanol, diethylaminoethanol, trichlorobenzene, chloronaphthalene, sulfolane, nitrobenzene, quinoline and urea. The amount of the solvent used is from 1 to 100 times in mass (i.e., in weight), preferably from 5 to 20 times in mass, the phthalonitrile compound.

In the reaction, 1,8-diazabicyclo[5.4.0]-7-undecene (DBU) or ammonium molybdate may be added as the catalyst. The amount thereof added is from 0.1 to 10 molar times, preferably from 0.5 to 2 molar times per 1 mol of the phthalonitrile compound and/or diiminoisoindoline derivative.

The reaction temperature is from 80 to 300° C., preferably from 100 to 250° C., more preferably from 130 to 230° C. If the reaction temperature is less than 80° C., the reaction rate is extremely low, whereas if it exceeds 300° C., decomposition of the phthalocyanine compound may occur.

The reaction time is from 2 to 20 hours, preferably from 5 to 15 hours, more preferably from 5 to 10 hours. If the reaction time is less than 2 hours, unreacted raw materials remain in a large amount, whereas if it exceeds 20 hours, decomposition of the phthalocyanine compound may occur.

The product obtained by this reaction is treated according to the normal after-treating method in the organic synthesis reaction and then through or not though purification, used as a commercial product.

The after-treatment must be a treatment of giving lithium ion as the counter cation of the ionic hydrophilic group.

More specifically, for example, the product isolated from the reaction system can be provided as a commercial product without purifying it or after performing operations of recrystallization and purification individually or in combination, for example, by column chromatography (for example, gel permeation chromatography (SEPHADEX™ LH-20, produced by Pharmacia)).

Also, after the completion of reaction, the reaction solvent is removed or not removed by distillation, the product is charged in water or ice and then neutralized or not neutralized, and the product isolated can be provided as a commercial product without purifying it or after performing operations of recrystallization and purification individually or in combination, for example, by column chromatography.

Furthermore, after the completion of reaction, the reaction solvent is removed or not removed by distillation, the product is charged in water or ice, neutralized or not neutralized, and then extracted with an organic solvent/an aqueous solution, and the product extracted can be provided as a commercial product without purifying it or after performing operations of recrystallization and purification individually or in combination by column chromatography.

The thus-obtained phthalocyanine compound represented by formulae (I), (II), (III) and (IV) usually includes the compounds represented by the following formulae (a)-1 to (a)-4. These four compounds are isomers different in the substitution sites of $G_1$ to $G_4$.

Formula (a)-1:

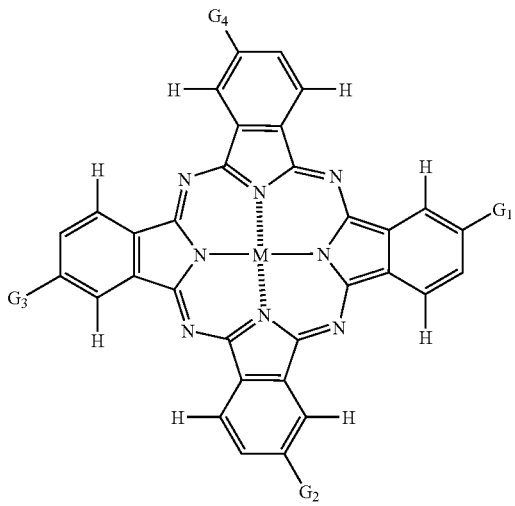

Formula (a)-2:

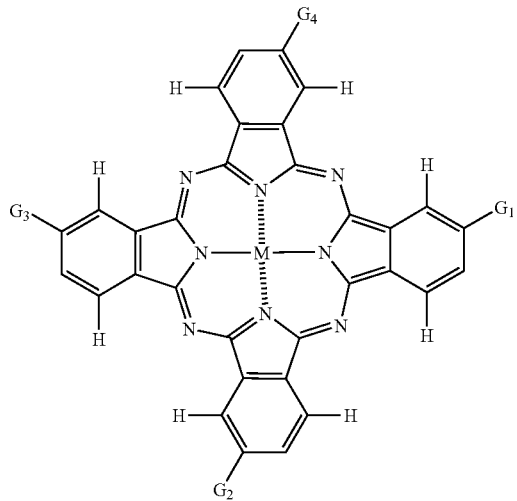

Formula (a)-3:

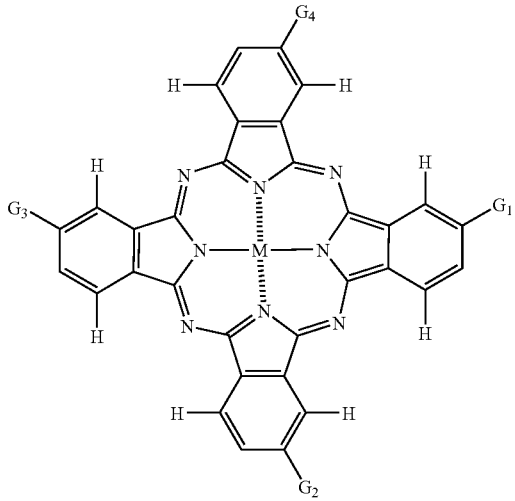

Formula (a)-4:

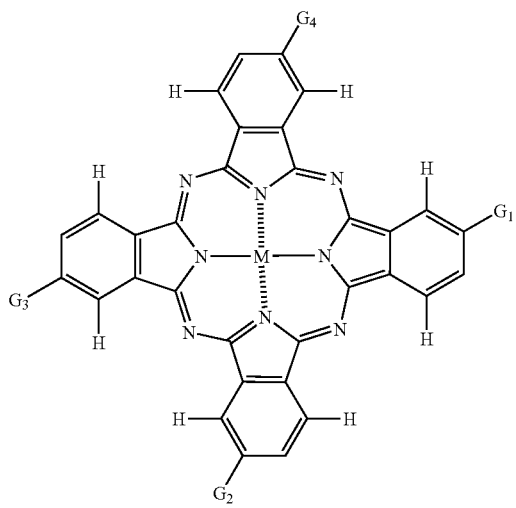

The compounds represented by formulae (a)-1 to (a)-4 are a β-position substitution type compound (a phthalocyanine compound having specific substituents at the 2- and/or 3-position, the 6- and/or 7-position, the 10- and/or 11-position, and the 14- and/or 15-position) and utterly different in the structure (substitution site) from the α-position substitution type and the α,β-position mixed substitution type. This structural feature is very important for the improvement of fastness.

In any substitution type, the specific substituents represented by, for example, $W_1$, $W_2$, $W_3$ and $W_4$ in formula (I) are very important for the improvement of fastness.

Furthermore, the structural feature very important for the improvement of fastness is a compound where specific substituents ($W_1$, $W_2$, $W_3$, $W_4$) in a specific number are introduced into specific sites (β-position substitution type) of a phthalocyanine mother nucleus {for example, in the case of a phthalocyanine mother nucleus, at least one or more of those specific substituents are contained in each pair of (2-position and/or 3-position), (6-position and/or 7-position), (10-position and/or 11-position) and (14-position and/or 15-position)}.

As for the structural feature of a water-soluble phthalocyanine compound having a specific spectral absorption property (absorbance ratio b/a<0.8; promotion of aggregated state), it has been found that a compound where specific substituents ($W_1$, $W_2$, $W_3$ and $W_4$, particularly, these are an electron-withdrawing group, preferably a sulfamoyl group or a sulfonyl group) in a specific number are introduced into specific sites (β-position substitution type) of a phthalocyanine mother nucleus is a most preferred structure in view of fastness and (color) hue of the image because the aggregated state is promoted.

In the present invention, it has been found that when the counter cation of the ionic hydrophilic group is lithium ion, the solubility in water and a water-miscible organic solvent is remarkably improved as compared with other cation species. Also in the phthalocyanine compound satisfying the spectral absorption property of the present invention and promoted in the formation of aggregated state, when the counter cation is lithium ion, the bronze phenomenon can be prevented from occurring on the recording material surface without changing the spectral absorption property and without impairing fastness and (color) hue of the image.

The ozone gas resistance referred to in the present invention is represented by a resistance against ozone gas and includes resistance (fastness) against oxidative atmospheres other than ozone gas. That is, the phthalocyanine compound represented by formula (I) according to the present invention is characterized by the strong resistance against oxidative gases present in the general environment, such as nitrogen oxide mostly contained in exhaust gas of automobiles, sulfur oxide mostly contained in exhaust from thermal power stations or factories, ozone gas generated by a radical chain reaction of these gases photochemically caused with solar light, photochemical smog abundant in oxygen-nitrogen or oxygen-hydrogen radical, and hydrogen peroxide radical generated from sites using special chemicals, for example, hair saloon. Accordingly, in the case where the image life is limited by the oxidative deterioration of image, such as outdoor advertisement and guide in railroad facility, ozone gas resistance can be improved by using the phthalocyanine compound of the present invention as the image-forming material.

Specific examples of the phthalocyanine compound represented by formula (I) of the present invention are set forth in the following tables (Compounds 101 to 215), however, the phthalocyanine compound of the present invention is not limited thereto.

In Tables, specific examples of each pair of ($R_1R_4$), ($R_2R_3$), ($R_5R_8$), ($R_6R_7$), ($R_9R_{12}$), ($R_{10}R_{11}$), ($R_{13}R_{16}$) and ($R_{14}R_{15}$) are independently shown in an irregular order.

TABLE 1

| Compound | M | $R_1R_4$ | $R_2R_3$ | $R_5R_8$ | $R_6R_7$ |
|---|---|---|---|---|---|
| 101 | Cu | H, H | H, —SO—(CH$_2$)$_3$SO$_3$Li | H, H | H, —SO—(CH$_2$)$_3$SO$_3$Li |
| 102 | Cu | H, H | H, —SO$_2$—(CH$_2$)$_3$SO$_3$Li | H, H | H, —SO$_2$—(CH$_2$)$_3$SO$_3$Li |
| 103 | Cu | H, H | H, —SO—⟨C$_6$H$_4$⟩—O(CH$_2$)$_4$SO$_3$Li | H, H | —SO—⟨C$_6$H$_4$⟩—O(CH$_2$)$_4$SO$_3$Li |
| 104 | Cu | H, | H, | H, | H, |

TABLE 1-continued

| | | | | | |
|---|---|---|---|---|---|
| | | H,<br>—SO$_2$—⟨C$_6$H$_4$⟩—O(CH$_2$)$_4$SO$_3$Li | | H | —SO$_2$—⟨C$_6$H$_4$⟩—O(CH$_2$)$_4$SO$_3$Li |
| 105 | Cu | H,<br>H | —SO—(CH$_2$)$_3$SO$_3$Li,<br>—SO—(CH$_2$)$_3$SO$_3$Li | H, | —SO—(CH$_2$)$_3$SO$_3$Li,<br>—SO—(CH$_2$)$_3$SO$_3$Li |

| Compound | R$_9$R$_{12}$ | R$_{10}$R$_{11}$ | R$_{13}$R$_{16}$ | R$_{14}$R$_{15}$ |
|---|---|---|---|---|
| 101 | H,<br>H | H,<br>—SO—(CH$_2$)$_3$SO$_3$Li | H,<br>H | H,<br>—SO—(CH$_2$)$_3$SO$_3$Li |
| 102 | H,<br>H | H,<br>—SO$_2$—(CH$_2$)$_3$SO$_3$Li | H,<br>H | H,<br>—SO$_2$—(CH$_2$)$_3$SO$_3$Li |
| 103 | H,<br>H | H,<br>—SO—⟨C$_6$H$_4$⟩—O(CH$_2$)$_4$SO$_3$Li | H,<br>H | —SO—⟨C$_6$H$_4$⟩—O(CH$_2$)$_4$SO$_3$Li |
| 104 | H,<br>H | H,<br>—SO$_2$—⟨C$_6$H$_4$⟩—O(CH$_2$)$_4$SO$_3$Li | H,<br>H | —SO$_2$—⟨C$_6$H$_4$⟩—O(CH$_2$)$_4$SO$_3$Li |
| 105 | H,<br>H | —SO—(CH$_2$)$_3$SO$_3$Li,<br>—SO—(CH$_2$)$_3$SO$_3$Li | H,<br>H | —SO—(CH$_2$)$_3$SO$_3$Li,<br>—SO—(CH$_2$)$_3$SO$_3$Li |

TABLE 2

| Compound | M | R$_1$R$_4$ | R$_2$R$_3$ | R$_5$R$_8$ | R$_6$R$_7$ |
|---|---|---|---|---|---|
| 106 | Cu | H,<br>H | —SO$_2$—(CH$_2$)$_3$SO$_3$Li<br>—SO$_2$—(CH$_2$)$_3$SO$_3$Li | H<br>H | —SO$_2$—(CH$_2$)$_3$SO$_3$Li<br>—SO$_2$—(CH$_2$)$_3$SO$_3$Li |
| 107 | Cu | H,<br>H | H,<br>—SO—⟨C$_6$H$_4$⟩—NHSO$_2$—⟨C$_6$H$_4$⟩—SO$_3$Li | H,<br>H | H,<br>—SO—⟨C$_6$H$_4$⟩—NHSO$_2$—⟨C$_6$H$_4$⟩—SO$_3$Li |
| 108 | Cu | H,<br>H | H,<br>—SO$_2$—⟨C$_6$H$_4$⟩—NHSO$_2$—⟨C$_6$H$_4$⟩—SO$_3$Li | H,<br>H | H,<br>—SO$_2$—⟨C$_6$H$_4$⟩—NHSO$_2$—⟨C$_6$H$_4$⟩—SO$_3$Li |
| 109 | Cu | H,<br>H | H,<br>—SO—⟨C$_6$H$_4$(SO$_3$Li)⟩—SO$_2$NH—⟨C$_6$H$_4$(SO$_3$Li)⟩ | H,<br>H | H,<br>—SO—⟨C$_6$H$_4$(SO$_3$Li)⟩—SO$_2$NH—⟨C$_6$H$_4$(SO$_3$Li)⟩ |
| 110 | Cu | H,<br>H | H,<br>—SO$_2$—⟨C$_6$H$_4$(SO$_3$Li)⟩—SO$_2$NH—⟨C$_6$H$_4$(SO$_3$Li)⟩ | H,<br>H | H,<br>—SO$_2$—⟨C$_6$H$_4$(SO$_3$Li)⟩—SO$_2$NH—⟨C$_6$H$_4$(SO$_3$Li)⟩ |

| Compound | R$_9$R$_{12}$ | R$_{10}$R$_{11}$ | R$_{13}$R$_{16}$ | R$_{14}$R$_{15}$ |
|---|---|---|---|---|
| 106 | H,<br>H | —SO$_2$—(CH$_2$)$_3$SO$_3$Li<br>—SO$_2$—(CH$_2$)$_3$SO$_3$Li | H,<br>H | —SO$_2$—(CH$_2$)$_3$SO$_3$Li<br>—SO$_2$—(CH$_2$)$_3$SO$_3$Li |
| 107 | H, | H, | H, | H, |

TABLE 2-continued

| | | | | | |
|---|---|---|---|---|---|
| | H H | —SO—⟨C6H4⟩—NHSO2—⟨C6H3⟩(SO3Li) | | | H H | —SO—⟨C6H4⟩—NHSO2—⟨C6H3⟩(SO3Li) |
| 108 | H, H | H, —SO2—⟨C6H4⟩—NHSO2—⟨C6H3⟩(SO3Li) | | H, H | H, —SO2—⟨C6H4⟩—NHSO2—⟨C6H3⟩(SO3Li) |
| 109 | H, H | H, —SO—⟨C6H3⟩(SO3Li)—SO2NH—⟨C6H4⟩(SO3Li) | | H, H | H, —SO—⟨C6H3⟩(SO3Li)—SO2NH—⟨C6H4⟩(SO3Li) |
| 110 | H, H | H, —SO2—⟨C6H3⟩(SO3Li)—SO2NH—⟨C6H4⟩(SO3Li) | | H, H | H, —SO2—⟨C6H3⟩(SO3Li)—SO2NH—⟨C6H4⟩(SO3Li) |

TABLE 3

| Compound | M | $R_1R_4$ | $R_2R_3$ | $R_5R_8$ | $R_6R_7$ |
|---|---|---|---|---|---|
| 111 | Cu | H, H | H, —SO—⟨C6H4⟩—CONH—⟨C6H3⟩(SO3Li)(SO3Li) | H, H | H, —SO—⟨C6H4⟩—CONH—⟨C6H3⟩(SO3Li)(SO3Li) |
| 112 | Cu | H, H | H, —SO2—⟨C6H4⟩—CONH—⟨C6H3⟩(SO3Li)(SO3Li) | H, H | H, —SO2—⟨C6H4⟩—CONH—⟨C6H3⟩(SO3Li)(SO3Li) |
| 113 | Cu | H, H | H, —SO—⟨C6H4⟩—CO2Li | H, H | H, —SO—⟨C6H4⟩—CO2Li |
| 114 | Cu | H, H | | H, | H, |

TABLE 3-continued

| Compound | | | | | | |
|---|---|---|---|---|---|---|
| | | H | —SO$_2$—C$_6$H$_4$—CO$_2$Li (para) | | H | —SO$_2$—C$_6$H$_4$—CO$_2$Li (para) |
| 115 | Cu | H, H | H, —SO—C$_6$H$_4$(CO$_2$Li) (ortho) | | H, H | H, —SO—C$_6$H$_4$(CO$_2$Li) (ortho) |

| Compound | R$_9$R$_{12}$ | R$_{10}$R$_{11}$ | R$_{13}$R$_{16}$ | R$_{14}$R$_{15}$ |
|---|---|---|---|---|
| 111 | H, H | H, —SO—(3-C$_6$H$_4$)—CONH—(3,5-(SO$_3$Li)$_2$-C$_6$H$_3$) | H, H | H, —SO—(3-C$_6$H$_4$)—CONH—(3,5-(SO$_3$Li)$_2$-C$_6$H$_3$) |
| 112 | H, H | H, —SO$_2$—(3-C$_6$H$_4$)—CONH—(3,5-(SO$_3$Li)$_2$-C$_6$H$_3$) | H, H | H, —SO$_2$—(3-C$_6$H$_4$)—CONH—(3,5-(SO$_3$Li)$_2$-C$_6$H$_3$) |
| 113 | H, H | H, —SO—C$_6$H$_4$—CO$_2$Li (para) | H, H | H, —SO—C$_6$H$_4$—CO$_2$Li (para) |
| 114 | H, H | H, —SO$_2$—C$_6$H$_4$—CO$_2$Li (para) | H, H | H, —SO$_2$—C$_6$H$_4$—CO$_2$Li (para) |
| 115 | H, H | H, —SO—C$_6$H$_4$(CO$_2$Li) (ortho) | H, H | H, —SO—C$_6$H$_4$(CO$_2$Li) (ortho) |

TABLE 4

| Compound | M | R$_1$R$_4$ | R$_2$R$_3$ | R$_5$R$_8$ | R$_6$R$_7$ |
|---|---|---|---|---|---|
| 116 | Cu | H, H | H, —SO$_2$—C$_6$H$_4$(CO$_2$Li) (ortho) | H, H | H, —SO$_2$—C$_6$H$_4$(CO$_2$Li) (ortho) |

TABLE 4-continued

| Compound | | $R_1R_4$ | $R_2R_3$ | | $R_5R_8$ | $R_6R_7$ |
|---|---|---|---|---|---|---|
| 117 | Cu | H, H | H, —SO—(2-imidazolyl)-N-(CH$_2$)$_4$SO$_3$Li | | H, H | H, —SO—(2-imidazolyl)-N-(CH$_2$)$_4$SO$_3$Li |
| 118 | Cu | H, H | H, —SO$_2$—(2-imidazolyl)-N-(CH$_2$)$_4$SO$_3$Li | | H, H | H, —SO$_2$—(2-imidazolyl)-N-(CH$_2$)$_4$SO$_3$Li |
| 119 | Cu | H, H | H, —SO—(2-benzimidazolyl)-N-(CH$_2$)$_3$SO$_3$Li | | H, H | H, —SO—(2-benzimidazolyl)-N-(CH$_2$)$_3$SO$_3$Li |
| 120 | Cu | H, H | H, —SO$_2$—(2-benzimidazolyl)-N-(CH$_2$)$_3$SO$_3$Li | | H, H | H, —SO$_2$—(2-benzimidazolyl)-N-(CH$_2$)$_3$SO$_3$Li |

| Compound | $R_9R_{12}$ | $R_{10}R_{11}$ | $R_{13}R_{16}$ | $R_{14}R_{15}$ |
|---|---|---|---|---|
| 116 | H, H | H, —SO$_2$—(2-CO$_2$Li-phenyl) | H, H | H, —SO$_2$—(2-CO$_2$Li-phenyl) |
| 117 | H, H | H, —SO—(2-imidazolyl)-N-(CH$_2$)$_4$SO$_3$Li | H, H | H, —SO—(2-imidazolyl)-N-(CH$_2$)$_4$SO$_3$Li |
| 118 | H, H | H, —SO$_2$—(2-imidazolyl)-N-(CH$_2$)$_4$SO$_3$Li | H, H | H, —SO$_2$—(2-imidazolyl)-N-(CH$_2$)$_4$SO$_3$Li |
| 119 | H, H | | H, H | |

TABLE 4-continued

| | | | | | |
|---|---|---|---|---|---|
| | | H ![benzimidazole with SO and (CH2)3SO3Li] | | H ![benzimidazole with SO and (CH2)3SO3Li] | |
| 120 | H, | H, | | H, | H, |
| | | H ![benzimidazole with SO2 and (CH2)3SO3Li] | | H ![benzimidazole with SO2 and (CH2)3SO3Li] | |

TABLE 5

| Compound | M | $R_1R_4$ | $R_2R_3$ | $R_5R_8$ | $R_6R_7$ |
|---|---|---|---|---|---|
| 121 | Cu | H, H | H, ![triazole with SO and (CH2)3SO3Li] | H, H | H, ![triazole with SO and (CH2)3SO3Li] |
| 122 | Cu | H, H | H, ![triazole with SO2 and (CH2)3SO3Li] | H, H | H, ![triazole with SO2 and (CH2)3SO3Li] |
| 123 | Cu | H, H | H, ![thiazole with SO, CH3 and CH2CO2Li] | H, H | H, ![thiazole with SO, CH3 and CH2CO2Li] |
| 124 | Cu | H, H | H, ![thiazole with SO2, CH3 and CH2CO2Li] | H, H | H, ![thiazole with SO2, CH3 and CH2CO2Li] |
| 125 | Cu | H, H | H, ![thiadiazole-SO-NHSO2-phenyl-SO3Li] | H, H | H, ![thiadiazole-SO-NHSO2-phenyl-SO3Li] |

| Compound | $R_9R_{12}$ | $R_{10}R_{11}$ | $R_{13}R_{16}$ | $R_{14}R_{15}$ |
|---|---|---|---|---|
| 121 | H, | H, | H, | H, |

TABLE 5-continued

| | | $R_1R_4$ / $R_2R_3$ | | $R_5R_8$ / $R_6R_7$ |
|---|---|---|---|---|
| | H | —SO-(1,2,4-triazol-3-yl with N4-(CH$_2$)$_3$SO$_3$Li) | H | —SO-(1,2,4-triazol-3-yl with N4-(CH$_2$)$_3$SO$_3$Li) |
| 122 | H, H | —SO$_2$-(1,2,4-triazol-3-yl with N4-(CH$_2$)$_3$SO$_3$Li) | H, H | —SO$_2$-(1,2,4-triazol-3-yl with N4-(CH$_2$)$_3$SO$_3$Li) |
| 123 | H, H | —SO-(4-methylthiazol-2-yl, 5-CH$_2$CO$_2$Li) | H, H | —SO-(4-methylthiazol-2-yl, 5-CH$_2$CO$_2$Li) |
| 124 | H, H | —SO$_2$-(4-methylthiazol-2-yl, 5-CH$_2$CO$_2$Li) | H, H | —SO$_2$-(4-methylthiazol-2-yl, 5-CH$_2$CO$_2$Li) |
| 125 | H, H | —SO-(1,3,4-thiadiazol-2-yl)-NHSO$_2$-(3-SO$_3$Li-phenyl) | H, H | —SO-(1,3,4-thiadiazol-2-yl)-NHSO$_2$-(3-SO$_3$Li-phenyl) |

TABLE 6

| Compound | M | $R_1R_4$ | $R_2R_3$ | $R_5R_8$ | $R_6R_7$ |
|---|---|---|---|---|---|
| 126 | Cu | H, H | —SO$_2$-(1,3,4-thiadiazol-2-yl)-NHSO$_2$-(3-SO$_3$Li-phenyl) | H, H | —SO$_2$-(1,3,4-thiadiazol-2-yl)-NHSO$_2$-(3-SO$_3$Li-phenyl) |
| 127 | Cu | H, H | —SO$_2$-(1,3,4-thiadiazol-2-yl)-SO$_2$(CH$_2$)$_4$SO$_3$Li | H, H | —SO$_2$-(1,3,4-thiadiazol-2-yl)-SO$_2$(CH$_2$)$_4$SO$_3$Li |
| 128 | Cu | H, H | —SO$_2$-(benzothiazol-2-yl)-6-NHCO-(3,5-bis-SO$_3$Li-phenyl) | H, H | —SO$_2$-(benzothiazol-2-yl)-6-NHCO-(3,5-bis-SO$_3$Li-phenyl) |
| 129 | Cu | H, H | | H, H | |

TABLE 6-continued

| Compound | M | R₁R₄ | R₂R₃ | R₅R₈ | R₆R₇ |
|---|---|---|---|---|---|
| | | H | —SO₂—[1,3,4-oxadiazole]—C₆H₄—NHCOC₂H₄CO₂Li | H | —SO₂—[1,3,4-oxadiazole]—C₆H₄—NHCOC₂H₄CO₂Li |
| 130 | Cu | H, H | —SO₂—[pyridine]—N—(CH₂)₄SO₃Li | H, H | —SO₂—[pyridine]—N—(CH₂)₄SO₃Li |

| Compound | R₁R₄ | R₂R₃ | R₅R₈ | R₆R₇ |
|---|---|---|---|---|
| 126 | H, H | —SO₂—[1,3,4-thiadiazole]—NHSO₂—C₆H₄—SO₃Li | H, H | —SO₂—[1,3,4-thiadiazole]—NHSO₂—C₆H₄—SO₃Li |
| 127 | H, H | —SO₂—[1,3,4-thiadiazole]—SO₂(CH₂)₄SO₃Li | H, H | —SO₂—[1,3,4-thiadiazole]—SO₂(CH₂)₄SO₃Li |
| 128 | H, H | —SO₂—[benzothiazole]—NHCO—C₆H₃(SO₃Li)₂ | H, H | —SO₂—[benzothiazole]—NHCO—C₆H₃(SO₃Li)₂ |
| 129 | H, H | —SO₂—[1,3,4-oxadiazole]—C₆H₄—NHCOC₂H₄CO₂Li | H, H | —SO₂—[1,3,4-oxadiazole]—C₆H₄—NHCOC₂H₄CO₂Li |
| 130 | H, H | —SO₂—[pyridine]—N—(CH₂)₄SO₃Li | H, H | —SO₂—[pyridine]—N—(CH₂)₄SO₃Li |

TABLE 7

| Compound | M | R₁ R₄ | R₂ R₃ | R₅ R₈ | R₆ R₇ | R₉ R₁₂ | R₁₀ R₁₁ | R₁₃ R₁₆ | R₁₄ R₁₅ |
|---|---|---|---|---|---|---|---|---|---|
| 131 | Cu | H, H | —Cl, —SO₂—(CH₂)₃SO₃Li, | H, H | —Cl, —SO₂—(CH₂)₃SO₃Li | H, H | —Cl, —SO₂—(CH₂)₃SO₃Li | H, H | —Cl, —SO₂—(CH₂)₃SO₃Li |
| 132 | Cu | H, H | —OCH₃, —SO—(CH₂)₃SO₃Li | H, H | —OCH₃, —SO—(CH₂)₃SO₃Li | H, H | —OCH₃, —SO—(CH₂)₃SO₃Li | H, H | —OCH₃, —SO—(CH₂)₃SO₃Li |
| 133 | Cu | H, H | —CN, —SO₂—(CH₂)₄SO₃Li | H, H | —CN, —SO₂—(CH₂)₄SO₃Li | H, H | —CN, —SO₂—(CH₂)₄SO₃Li | H, H | —CN, —SO₂—(CH₂)₄SO₃Li |
| 134 | Ni | H, H | —SO₂—(CH₂)₃SO₃Li, —SO₂—(CH₂)₃SO₃Li | H, H | —SO₂—(CH₂)₃SO₃Li, —SO₂—(CH₂)₃SO₃Li | H, H | —SO₂—(CH₂)₃SO₃Li, —SO₂—(CH₂)₃SO₃Li | H, H | —SO₂—(CH₂)₃SO₃Li, —SO₂—(CH₂)₃SO₃Li |

TABLE 7-continued
| Compound | M | R₁ R₄ R₂ R₃ | R₅ R₈ R₆ R₇ | R₉ R₁₂ R₁₀ R₁₁ | R₁₃ R₁₆ R₁₄ R₁₅ |
|---|---|---|---|---|---|
| 135 | Zn | H, H  H,<br>—SO₂—(CH₂)₃SO₃Li | H, H  H,<br>—SO₂—(CH₂)₃SO₃Li | H, H  H,<br>—SO₂—(CH₂)₃SO₃Li | H, H  H,<br>—SO₂—(CH₂)₃SO₃Li |
TABLE 8
| Compound | M | R₁R₄ | R₂R₃ | R₅R₈ | R₆R₇ |
|---|---|---|---|---|---|
| 136 | Cu | H, H | 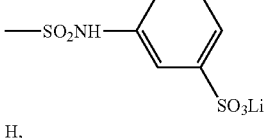 | H, H | 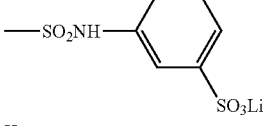 |
| 137 | Cu | H, H | 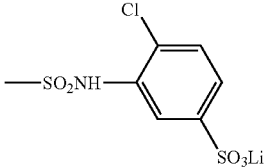 | H, H | 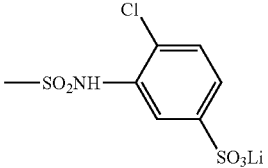 |
| 138 | Cu | H, H | 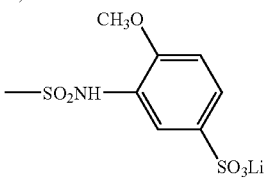 | H, H | 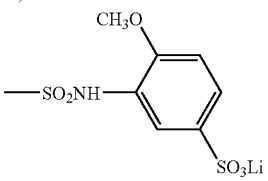 |
| 139 | Cu | H, H | 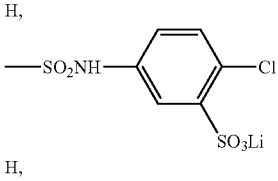 | H, H | 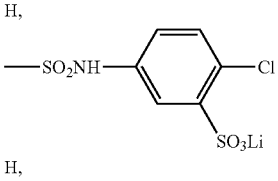 |
| 140 | Cu | H, H | 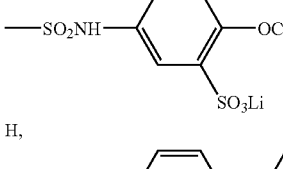 | H, H | 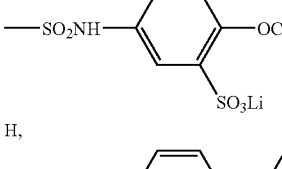 |
| 141 | Cu | H, H | 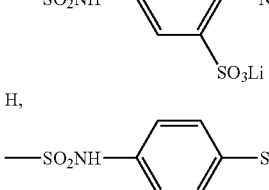 | H, H | 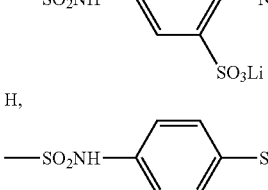 |
| 142 | Cu | H, H |  | H, H |  |
| 143 | Cu | H, H | 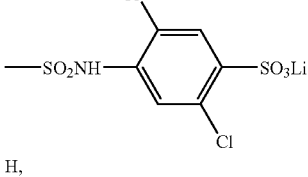 | H, H | 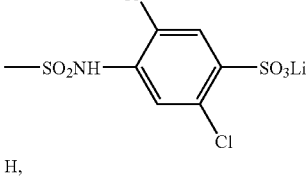 |
| 144 | Cu | H, | H, | H, | H, |

TABLE 8-continued

| Compound | | | | | |
|---|---|---|---|---|---|
| | | —SO$_2$NH—⟨2,6-diCl, 4-SO$_3$Li-phenyl⟩ H | | —SO$_2$NH—⟨2,6-diCl, 4-SO$_3$Li-phenyl⟩ H | |
| 145 | Cu | H, H | —SO$_2$NH—⟨3-(NHCO-3-SO$_3$Li-phenyl)-phenyl⟩ | H, H | —SO$_2$NH—⟨3-(NHCO-3-SO$_3$Li-phenyl)-phenyl⟩ |

| Compound | R$_9$R$_{12}$ | R$_{10}$R$_{11}$ | R$_{13}$R$_{16}$ | R$_{14}$R$_{15}$ |
|---|---|---|---|---|
| 136 | H, H | —SO$_2$NH—⟨3-SO$_3$Li-phenyl⟩ | H, H | —SO$_2$NH—⟨3-SO$_3$Li-phenyl⟩ |
| 137 | H, H | —SO$_2$NH—⟨2-Cl, 5-SO$_3$Li-phenyl⟩ | H, H | —SO$_2$NH—⟨2-Cl, 5-SO$_3$Li-phenyl⟩ |
| 138 | H, H | —SO$_2$NH—⟨2-OCH$_3$, 5-SO$_3$Li-phenyl⟩ | H, H | —SO$_2$NH—⟨2-OCH$_3$, 5-SO$_3$Li-phenyl⟩ |
| 139 | H, H | —SO$_2$NH—⟨4-Cl, 3-SO$_3$Li-phenyl⟩ | H, H | —SO$_2$NH—⟨4-Cl, 3-SO$_3$Li-phenyl⟩ |
| 140 | H, H | —SO$_2$NH—⟨4-OC$_2$H$_4$OCH$_3$, 3-SO$_3$Li-phenyl⟩ | H, H | —SO$_2$NH—⟨4-OC$_2$H$_4$OCH$_3$, 3-SO$_3$Li-phenyl⟩ |
| 141 | H, H | —SO$_2$NH—⟨4-morpholino, 3-SO$_3$Li-phenyl⟩ | H, H | —SO$_2$NH—⟨4-morpholino, 3-SO$_3$Li-phenyl⟩ |
| 142 | H, H | —SO$_2$NH—⟨4-SO$_3$Li-phenyl⟩ | H, H | —SO$_2$NH—⟨4-SO$_3$Li-phenyl⟩ |
| 143 | H, | | H, | |

TABLE 8-continued

| | | | | |
|---|---|---|---|---|
| | H | 2,5-Cl₂-4-SO₃Li-C₆H₂-NHSO₂- | | H | 2,5-Cl₂-4-SO₃Li-C₆H₂-NHSO₂- |
| 144 | H, H | H, 2,6-Cl₂-4-SO₃Li-C₆H₂-NHSO₂- | | H, H | H, 2,6-Cl₂-4-SO₃Li-C₆H₂-NHSO₂- |
| 145 | H, H | H, 3-(3-SO₃Li-C₆H₄-CONH)-C₆H₄-NHSO₂- | | H, H | H, 3-(3-SO₃Li-C₆H₄-CONH)-C₆H₄-NHSO₂- |

TABLE 9

| Compound | M | R₁R₄ | R₂R₃ | R₅R₈ | R₆R₇ |
|---|---|---|---|---|---|
| 146 | Cu | H, H | H, 3-(3-SO₃Li-C₆H₄-SO₂NH)-C₆H₄-NHSO₂- | H, H | H, 3-(3-SO₃Li-C₆H₄-SO₂NH)-C₆H₄-NHSO₂- |
| 147 | Cu | H, H | H, 3-(3,5-(SO₃Li)₂-C₆H₃-SO₂NH)-C₆H₄-NHSO₂- | H, H | H, 3-(3,5-(SO₃Li)₂-C₆H₃-SO₂NH)-C₆H₄-NHSO₂- |
| 148 | Cu | H, H | H, 2-LiO₂S-C₆H₄-NHSO₂- | H, H | H, 2-LiO₂S-C₆H₄-NHSO₂- |
| 149 | Cu | H, H | H, 2,6-(CH₃)₂-4-SO₃Li-C₆H₂-NHSO₂- | H, H | H, 2,6-(CH₃)₂-4-SO₃Li-C₆H₂-NHSO₂- |
| 150 | Cu | H, | | H, | |

TABLE 9-continued

| | | | 51 | 52 |
|---|---|---|---|---|
| | | H | —SO₂NH-C₆H₄(3-SO₂NH-C₆H₃(3,5-(SO₃Li)₂)) | —SO₂NH-C₆H₄(3-SO₂NH-C₆H₃(3,5-(SO₃Li)₂)) |
| 151 | Cu | H, H | H, —SO₂NH-C₆H₄(4-SO₂NH-C₆H₃(3,5-(SO₃Li)₂)) | H, —SO₂NH-C₆H₄(4-SO₂NH-C₆H₃(3,5-(SO₃Li)₂)) |
| 152 | Cu | H, H | H, —SO₂NH-C₆H₃(3,5-(SO₂NH-C₆H₃(3,5-(SO₃Li)₂))₂) | H, —SO₂NH-C₆H₃(3,5-(SO₂NH-C₆H₃(3,5-(SO₃Li)₂))₂) |
| 153 | Cu | H, H | H, —SO₂NH-C₆H₃(4-Cl, 3-SO₂NH-C₆H₃(2,5-(SO₃Li)₂)) | H, —SO₂NH-C₆H₃(4-Cl, 3-SO₂NH-C₆H₃(2,5-(SO₃Li)₂)) |
| 154 | Cu | H, H | H, —SO₂NH-C₆H₃(4-Cl, 3-SO₂NH-C₆H₃(3,5-(SO₃Li)₂)) | H, —SO₂NH-C₆H₃(4-Cl, 3-SO₂NH-C₆H₃(3,5-(SO₃Li)₂)) |
| 155 | Cu | H, H | H, —SO₂NH-C₆H₄(3-SO₂NH(CH₂)₃SO₃Li) | H, —SO₂NH-C₆H₄(3-SO₂NH(CH₂)₃SO₃Li) |

TABLE 9-continued

| Compound | R₁R₄ | R₂R₃ | R₅R₈ | R₆R₇ |
|---|---|---|---|---|
| 146 | H, H | H, —SO₂NH-(3-SO₃Li phenyl)-NHSO₂-(3-phenyl-SO₃Li)- | H, H | H, —SO₂NH-(3-SO₃Li phenyl)-NHSO₂-(3-phenyl)- |
| 147 | H, H | H, —SO₂NH-(3-substituted phenyl)-NHSO₂-(3,5-di-SO₃Li phenyl) | H, H | H, —SO₂NH-(3-substituted phenyl)-NHSO₂-(3,5-di-SO₃Li phenyl) |
| 148 | H, H | H, —SO₂NH-(2-SO₂Li phenyl) | H, H | H, —SO₂NH-(2-SO₂Li phenyl) |
| 149 | H, H | H, —SO₂NH-(2,6-dimethyl-4-SO₃Li phenyl) | H, H | H, —SO₂NH-(2,6-dimethyl-4-SO₃Li phenyl) |
| 150 | H, H | H, —SO₂NH-(3-SO₂NH-(3,5-di-SO₃Li phenyl)phenyl) | H, H | H, —SO₂NH-(3-SO₂NH-(3,5-di-SO₃Li phenyl)phenyl) |
| 151 | H, H | H, —SO₂NH-(4-SO₂NH-(3,5-di-SO₃Li phenyl)phenyl) | H, H | H, —SO₂NH-(4-SO₂NH-(3,5-di-SO₃Li phenyl)phenyl) |
| 152 | H, H | H, | H, | H, |

TABLE 9-continued

| # | R₁R₄ / R₂R₃ | R₅R₈ / R₆R₇ |
|---|---|---|
|  | H, H / —SO₂NH-[3,5-bis(SO₃Li)phenyl-NHSO₂-]-benzene-5-[SO₂NH-3,5-bis(SO₃Li)phenyl] | H, H / —SO₂NH-[3,5-bis(SO₃Li)phenyl-NHSO₂-]-benzene-5-[SO₂NH-3,5-bis(SO₃Li)phenyl] |
| 153 | H, H / —SO₂NH-(4-Cl-phenyl)-3-[SO₂NH-(2,5-bis(SO₃Li))phenyl] | H, H / —SO₂NH-(4-Cl-phenyl)-3-[SO₂NH-(2,5-bis(SO₃Li))phenyl] |
| 154 | H, H / —SO₂NH-(4-Cl-phenyl)-3-[SO₂NH-(3,5-bis(SO₃Li))phenyl] | H, H / —SO₂NH-(4-Cl-phenyl)-3-[SO₂NH-(3,5-bis(SO₃Li))phenyl] |
| 155 | H, H / —SO₂NH-(3-SO₂NH(CH₂)₃SO₃Li)phenyl | H, H / —SO₂NH-(3-SO₂NH(CH₂)₃SO₃Li)phenyl |

TABLE 10

| Compound | M | R₁R₄ | R₂R₃ | R₅R₈ | R₆R₇ |
|---|---|---|---|---|---|
| 156 | Cu | H, H | —SO₂NH-C₆H₄-SO₂NH(CH₂)₃SO₃Li | H, H | —SO₂NH-C₆H₄-SO₂NH(CH₂)₃SO₃Li |
| 157 | Cu | H, H | —SO₂NH-(2-SO₂NH(CH₃)₄SO₃Li)phenyl | H, H | —SO₂NH-(2-SO₂NH(CH₃)₄SO₃Li)phenyl |
| 158 | Cu | H, H |  | H, H |  |

TABLE 10-continued

| Compound | | $R_9R_{12}$ | $R_{10}R_{11}$ | | $R_{13}R_{16}$ | $R_{14}R_{15}$ |
|---|---|---|---|---|---|---|
| | | H, | H, | | H, | H, |
| | | H | —SO$_2$NH—(2-SO$_2$CH$_3$, 4-SO$_3$Li-phenyl) | | H | —SO$_2$NH—(2-SO$_2$CH$_3$, 4-SO$_3$Li-phenyl) |
| 159 | Cu | H, H | —SO$_2$NH—(2-SO$_3$Li, 4-SO$_2$CH$_3$-phenyl) | | H, H | —SO$_2$NH—(2-SO$_3$Li, 4-SO$_2$CH$_3$-phenyl) |
| 160 | Cu | H, H | —SO$_2$NH—(2-CN, 4-SO$_3$Li-phenyl) | | H, H | —SO$_2$NH—(2-CN, 4-SO$_3$Li-phenyl) |
| 161 | Cu | H, H | —SO$_2$NH—(2-SO$_3$Li, 4-CN-phenyl) | | H, H | —SO$_2$NH—(2-SO$_3$Li, 4-CN-phenyl) |
| 162 | Zn | H, H | —SO$_2$NH—(2-Cl, 4-SO$_3$Li-phenyl) | | H, H | —SO$_2$NH—(2-Cl, 4-SO$_3$Li-phenyl) |
| 163 | Ni | H, H | —SO$_2$-(3-(NHSO$_2$-(3-SO$_3$Li-phenyl))-phenyl) | | H, H | —SO$_2$-(3-(NHSO$_2$-(3-SO$_3$Li-phenyl))-phenyl) |
| 164 | Cu | H, Cl | —SO$_2$NH—(2-Cl, 5-SO$_3$Li-phenyl) | | H, Cl | —SO$_2$NH—(2-Cl, 5-SO$_3$Li-phenyl) |
| 165 | Cu | H, SO$_2$-CH$_3$ | —SO$_2$NH—(3-SO$_3$Li-phenyl) | | H, SO$_2$-CH$_3$ | —SO$_2$NH—(3-SO$_3$Li-phenyl) |

| Compound | $R_9R_{12}$ | $R_{10}R_{11}$ | $R_{13}R_{16}$ | $R_{14}R_{15}$ |
|---|---|---|---|---|
| 156 | H, H | —SO$_2$NH—(4-SO$_2$NH(CH$_2$)$_3$SO$_3$Li-phenyl) | H, H | —SO$_2$NH—(4-SO$_2$NH(CH$_2$)$_3$SO$_3$Li-phenyl) |
| 157 | H, H | —SO$_2$NH—(2-SO$_2$NH(CH$_3$)$_4$SO$_3$Li-phenyl) | H, H | —SO$_2$NH—(2-SO$_2$NH(CH$_3$)$_4$SO$_3$Li-phenyl) |
| 158 | H, | | H, | |

TABLE 10-continued

| | | | | | |
|---|---|---|---|---|---|
| | H | (SO3Li)) | H | (SO3Li)) | |
| 159 | H, H | H, (SO2CH3)) | H, H | H, (SO2CH3)) | |
| 160 | H, H | H, (SO3Li)) | H, H | H, (SO3Li)) | |
| 161 | H, H | H, (CN)) | H, H | H, (CN)) | |
| 162 | H, H | H, (SO3Li)) | H, H | H, (SO3Li)) | |
| 163 | H, H | H, | H, H | H, | |
| 164 | H, Cl | H, (SO3Li)) | H, Cl | H, (SO3Li)) | |
| 165 | H, SO2-CH3 | H, | H, SO2-CH3 | H, | |

TABLE 11

| Compound | M | R1R4 | R2R3 | R5R8 | R6R7 |
|---|---|---|---|---|---|
| 166 | Cu | H, H | H, | H, H | H, |

TABLE 11-continued

| | | | | | | |
|---|---|---|---|---|---|---|
| 167 | Cu | H, H | H, —SO$_2$NH-[naphthalene with SO$_3$Li, LiO$_3$S substituents] | | H, H | —SO$_2$NH-[naphthalene with SO$_3$Li, LiO$_3$S substituents] |
| 168 | Cu | H, H | H, —SO$_2$NH-[naphthalene with SO$_3$Li, LiO$_3$S substituents] | | H, H | —SO$_2$NH-[naphthalene with SO$_3$Li, LiO$_3$S substituents] |
| 169 | Cu | H, H | H, —SO$_2$NH-[naphthalene with SO$_2$Li, LiO$_3$S substituents] | | H, H | —SO$_2$NH-[naphthalene with SO$_2$Li, LiO$_3$S substituents] |
| 170 | Cu | H, H | H, —SO$_2$NH-[naphthalene with SO$_3$Li, LiO$_3$S, SO$_3$Li substituents] | | H, H | —SO$_2$NH-[naphthalene with SO$_3$Li, LiO$_3$S, SO$_3$Li substituents] |

| Compound | R$_9$R$_{12}$ | R$_{10}$R$_{11}$ | R$_{13}$R$_{16}$ | R$_{14}$R$_{15}$ |
|---|---|---|---|---|
| 166 | H, H | H, —SO$_2$NH-[naphthalene with SO$_3$Li] | H, H | —SO$_2$NH-[naphthalene with SO$_3$Li] |
| 167 | H, H | H, —SO$_2$NH-[naphthalene with SO$_3$Li, LiO$_3$S] | H, H | —SO$_2$NH-[naphthalene with SO$_3$Li, LiO$_3$S] |
| 168 | H, | H, | H, | H, |

TABLE 11-continued

| | | | | | |
|---|---|---|---|---|---|
| | H | —SO₂NH-(naphthalene with SO₃Li and LiO₃S) | | H | —SO₂NH-(naphthalene with SO₃Li and LiO₃S) |
| 169 | H, H | H, —SO₂NH-(naphthalene with LiO₃S and SO₂Li) | | H, H | H, —SO₂NH-(naphthalene with LiO₃S and SO₂Li) |
| 170 | H, H | H, —SO₂NH-(naphthalene with SO₃Li, LiO₃S, SO₃Li) | | H, H | H, —SO₂NH-(naphthalene with SO₃Li, LiO₃S, SO₃Li) |

TABLE 12

| Compound | M | $R_1R_4$ | $R_2R_3$ | $R_5R_8$ | $R_6R_7$ |
|---|---|---|---|---|---|
| 171 | Cu | H, H | H, —SO₂(CH₂)₂O(CH₂)₂SO₃Li | H, H | H, —SO₂(CH₂)₂O(CH₂)₂SO₃Li |
| 172 | Cu | H, H | H, —SO₂NH·(CH₂)₃—N(C₂H₄O-benzoyl-SO₃Li)₂ | H, H | H, —SO₂NH·(CH₂)₃—N(C₂H₄O-benzoyl-SO₃Li)₂ |
| 173 | Cu | H, H | H, —SO₂[(CH₂)₂O]₂(CH₂)₂SO₃Li | H, H | H, —SO₂[(CH₂)₂O]₂(CH₂)₂SO₃Li |
| 174 | Cu | H, H | H, —SO₂[(CH₂)₂O]₃(CH₂)₂SO₃Li | H, H | H, —SO₂[(CH₂)₂O]₃(CH₂)₂SO₃Li |
| 175 | Cu | H, H | H, —SO₂NH·(CH₂)₃—N(C₂H₄SO₃Li)₂ | H, H | H, —SO₂NH·(CH₂)₃—N(C₂H₄SO₃Li)₂ |

| Compound | $R_9R_{12}$ | $R_{10}R_{11}$ | $R_{13}R_{16}$ | $R_{14}R_{15}$ |
|---|---|---|---|---|
| 171 | H, H | H, —SO₂(CH₂)₂O(CH₂)₂SO₃Li | H, H | H, —SO₂(CH₂)₂O(CH₂)₂SO₃Li |

TABLE 12-continued

| | | | | | |
|---|---|---|---|---|---|
| 172 | H, | H, | | H, | H, |
| | H | —SO$_2$NH•(CH$_2$)$_3$—N(C$_2$H$_4$O—C(O)—C$_6$H$_4$—SO$_3$Li)$_2$ | | H | —SO$_2$NH•(CH$_2$)$_3$—N(C$_2$H$_4$O—C(O)—C$_6$H$_4$—SO$_3$Li)$_2$ |
| 173 | H, | H, | | H, | H, |
| | H | —SO$_2$[(CH$_2$)$_2$O]$_2$(CH$_2$)$_2$SO$_3$Li | | H | —SO$_2$[(CH$_2$)$_2$O]$_2$(CH$_2$)$_2$SO$_3$Li |
| 174 | H, | H, | | H, | H, |
| | H | —SO$_2$[(CH$_2$)$_2$O]$_3$(CH$_2$)$_2$SO$_3$Li | | H | —SO$_2$[(CH$_2$)$_2$O]$_3$(CH$_2$)$_2$SO$_3$Li |
| 175 | H, | H, | | H, | H, |
| | H | —SO$_2$NH•(CH$_2$)$_3$—N(C$_2$H$_4$SO$_3$Li)$_2$ | | H | —SO$_2$NH•(CH$_2$)$_3$—N(C$_2$H$_4$SO$_3$Li)$_2$ |

TABLE 13

| Compound | M | R$_1$R$_4$ | R$_2$R$_3$ | R$_5$R$_8$ | R$_6$R$_7$ |
|---|---|---|---|---|---|
| 176 | Zn | H, H | H, —SO$_2$NH•(CH$_2$)$_3$—N(C$_2$H$_4$SO$_3$Li)$_2$ | H, H | H, —SO$_2$NH•(CH$_2$)$_3$—N(C$_2$H$_4$SO$_3$Li)$_2$ |
| 177 | Cu | H, H | H, —SO$_2$NH•(CH$_2$)$_3$—N(C$_2$H$_4$OH)((CH$_2$)$_3$SO$_3$Li) | H, H | H, —SO$_2$NH•(CH$_2$)$_3$—N(C$_2$H$_4$OH)((CH$_2$)$_3$SO$_3$Li) |
| 178 | Cu | H, H | H, —SO$_2$NH(CH$_2$)$_3$—O—C$_6$H$_4$—SO$_3$Li | H, H | H, —SO$_2$NH(CH$_2$)$_3$—O—C$_6$H$_4$—SO$_3$Li |
| 179 | Cu | H, H | H, —SO$_2$NH(CH$_2$)$_3$—N((CH$_2$)$_3$SO$_3$Li)((CH$_2$)$_3$—N(C$_2$H$_4$OH)$_2$) | H, H | H, —SO$_2$NH(CH$_2$)$_3$—N((CH$_2$)$_3$SO$_3$Li)((CH$_2$)$_3$—N(C$_2$H$_4$OH)$_2$) |
| 180 | Cu | H, H | H, —SO$_2$NH.(CH$_2$)$_3$—SO$_3$Li | H, H | H, —SO$_2$NH.(CH$_2$)$_3$—SO$_3$Li |

| Compound | R$_9$R$_{12}$ | R$_{10}$R$_{11}$ | R$_{13}$R$_{16}$ | R$_{14}$R$_{15}$ |
|---|---|---|---|---|
| 176 | H, | H, | H, | H, |

TABLE 13-continued

| | | | | |
|---|---|---|---|---|
| | H H | —SO₂NH·(CH₂)₃—N(C₂H₄SO₃Li)(C₂H₄SO₃Li) | H | —SO₂NH·(CH₂)₃—N(C₂H₄SO₃Li)(C₂H₄SO₃Li) |
| 177 | H, H | —SO₂NH·(CH₂)₃—N(C₂H₄OH)((CH₂)₃SO₃Li) | H, H | —SO₂NH·(CH₂)₃—N(C₂H₄OH)((CH₂)₃SO₃Li) |
| 178 | H, H | —SO₂NH(CH₂)₃—O—C₆H₄—SO₃Li | H, H | —SO₂NH(CH₂)₃—O—C₆H₄—SO₃Li |
| 179 | H, H | —SO₂NH(CH₂)₃—N((CH₂)₃SO₃Li)((CH₂)₃—N(C₂H₄OH)(C₂H₄OH)) | H, H | —SO₂NH(CH₂)₃—N((CH₂)₃SO₃Li)((CH₂)₃—N(C₂H₄OH)(C₂H₄OH)) |
| 180 | H, H | —SO₂NH.(CH₂)₃—SO₃Li | H, H | —SO₂NH.(CH₂)₃—SO₃Li |

TABLE 14

| Compound | M | R₁R₄ | R₂R₃ | R₅R₈ | R₆R₇ |
|---|---|---|---|---|---|
| 181 | Cu | H, H | 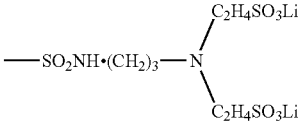 | H, H | 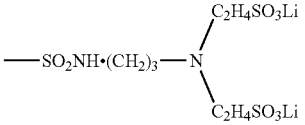 |
| 182 | Cu | H, H | 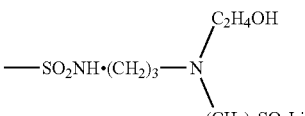 | H, H | 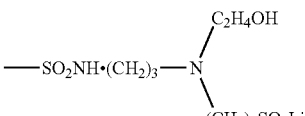 |
| 183 | Ni | H, H | | H, H | |

TABLE 14-continued

| Compound | | | | | | |
|---|---|---|---|---|---|---|
| 184 | Cu | H, H | H, [pyrazole-CN with 2,6-dichloro-4-SO₃Li phenyl, —SO₂NH—] | H | H, [pyrazole-CN with 2,6-dichloro-4-SO₃Li phenyl, —SO₂NH—] | |
| 185 | Zn | H, H | H, [pyrazole-C₄H₉(t) with 3,5-di(SO₃Li) phenyl, —SO₂NH—] | H | H, [pyrazole-C₄H₉(t) with 3,5-di(SO₃Li) phenyl, —SO₂NH—] | |

| Compound | R₉R₁₂ | R₁₀R₁₁ | | R₁₃R₁₆ | R₁₄R₁₅ | |
|---|---|---|---|---|---|---|
| 181 | H, H | H, [pyrazole-CH₃ with 2-SO₃Li, 5-SO₃Li phenyl, —SO₂NH—] | | H | H, [same group] | |
| 182 | H, H | H, [pyrazole-Br with 2,6-dichloro-4-SO₃Li phenyl, —SO₂NH—] | | H | H, [same group] | |

TABLE 14-continued
| 183 | H, H, H | 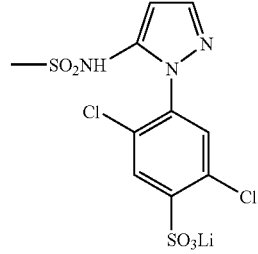 | H, H | 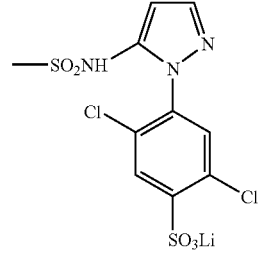 |
| 184 | H, H, H | 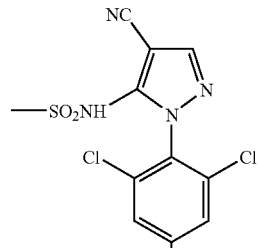 | H, H | 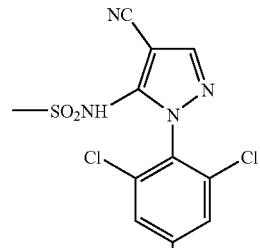 |
| 185 | H, H, H | 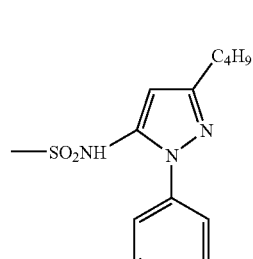 | H, H | 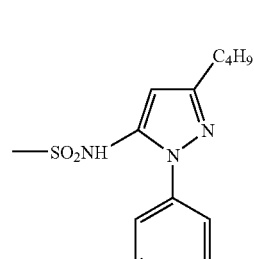 |
TABLE 15
| Compound | M | $R_1R_4$ | $R_2R_3$ | $R_5R_8$ | $R_6R_7$ |
|---|---|---|---|---|---|
| 186 | Cu | H, H | H,  | H, H | H,  |
| 187 | Cu | H, H | | H, H | |

TABLE 15-continued

| Compound | | | | | | |
|---|---|---|---|---|---|---|
| | | H | 3-(SCH₃)-1,2,4-triazole with SO₂NH, phenyl bearing SO₃Li groups | H | | 3-(SCH₃)-1,2,4-triazole with SO₂NH, phenyl bearing SO₃Li groups |
| 188 | Cu | H, H | H, 3-(SC₂H₄SO₃Li)-1,3,4-thiadiazole-SO₂NH | H | H, | 3-(SC₂H₄SO₃Li)-1,3,4-thiadiazole-SO₂NH |
| 189 | Cu | H, H | H, 2-(SC₂H₄SO₃Li)-1,3,4-thiadiazole-SO₂NH | H | H, | 2-(SC₂H₄SO₃Li)-1,3,4-thiadiazole-SO₂NH |
| 190 | Cu | H, H | H, 3-(SC₂H₄SO₃Li)-isothiazole-SO₂NH | H | H, | 3-(SC₂H₄SO₃Li)-isothiazole-SO₂NH |

| Compound | R₉R₁₂ | R₁₀R₁₁ | | R₁₃R₁₆ | R₁₄R₁₅ | |
|---|---|---|---|---|---|---|
| 186 | H, H | H, 3-Ph-pyrazole-SO₂NH with phenyl bearing SO₃Li groups | | H | H, | 3-Ph-pyrazole-SO₂NH with phenyl bearing SO₃Li groups |
| 187 | H, H | H, 3-(SCH₃)-1,2,4-triazole-SO₂NH with phenyl bearing SO₃Li groups | | H | H, | 3-(SCH₃)-1,2,4-triazole-SO₂NH with phenyl bearing SO₃Li groups |
| 188 | H, H | H, 3-(SC₂H₄SO₃Li)-1,3,4-thiadiazole-SO₂NH | | H | H, | 3-(SC₂H₄SO₃Li)-1,3,4-thiadiazole-SO₂NH |

TABLE 15-continued

| 189 | H, H | H | [SO₂NH-(1,3,4-thiadiazol-2,5-diyl)-SC₂H₄SO₃Li] | H, H | [SO₂NH-(1,3,4-thiadiazol-2,5-diyl)-SC₂H₄SO₃Li] |
|---|---|---|---|---|---|
| 190 | H, H | H | [SO₂NH-(isothiazol-3,5-diyl)-SC₂H₄SO₃Li] | H, H | [SO₂NH-(isothiazol-3,5-diyl)-SC₂H₄SO₃Li] |

TABLE 16

| Compound | M | R₁R₄ | R₂R₃ | R₅R₈ | R₆R₇ |
|---|---|---|---|---|---|
| 191 | Cu | H, H | —SO₂NH-(benzisothiazol-3-yl)-6-SO₃Li | H, H | —SO₂NH-(benzisothiazol-3-yl)-6-SO₃Li |
| 192 | Cu | H, H | —SO₂NH-(benzothiazol-2-yl)-6-SO₃Li | H, H | —SO₂NH-(benzothiazol-2-yl)-6-SO₃Li |
| 193 | Cu | H, H | —SO₂NH-(thiazol-2-yl)-4-C₃H₈SO₃Li | H, H | —SO₂NH-(thiazol-2-yl)-4-C₃H₈SO₃Li |
| 194 | Cu | H, H | —SO₂NH-(imidazol-5-yl)-1-(CH₂)₄SO₃Li | H, H | —SO₂NH-(imidazol-5-yl)-1-(CH₂)₄SO₃Li |
| 195 | Cu | H, H | —SO₂NH-(3-CN-4-Ph-pyrrol-2-yl)-1-(CH₂)₄SO₃Li | H, H | —SO₂NH-(3-CN-4-Ph-pyrrol-2-yl)-1-(CH₂)₄SO₃Li |

| Compound | R₉R₁₂ | R₁₀R₁₁ | R₁₃R₁₆ | R₁₄R₁₅ |
|---|---|---|---|---|
| 191 | H, | H, | H, | H, |

TABLE 16-continued

| | | | | |
|---|---|---|---|---|
| | H | —SO₂NH-[3-sulfonato-benzo[c]isothiazol-6-yl (SO₃Li)] | H | —SO₂NH-[3-sulfonato-benzo[c]isothiazol-6-yl (SO₃Li)] |
| 192 | H, H, H | —SO₂NH-[benzothiazol-2-yl-6-SO₃Li] | H, H | —SO₂NH-[benzothiazol-2-yl-6-SO₃Li] |
| 193 | H, H, H | —SO₂NH-[thiazol-2-yl-4-C₃H₈SO₃Li] | H, H | —SO₂NH-[thiazol-2-yl-4-C₃H₈SO₃Li] |
| 194 | H, H, H | —SO₂NH-[imidazol-5-yl, N-(CH₂)₄SO₃Li] | H, H | —SO₂NH-[imidazol-5-yl, N-(CH₂)₄SO₃Li] |
| 195 | H, H, H | —SO₂NH-[3-CN-4-Ph-pyrrol-2-yl, N-(CH₂)₄SO₃Li] | H, H | —SO₂NH-[3-CN-4-Ph-pyrrol-2-yl, N-(CH₂)₄SO₃Li] |

TABLE 17

| Compound | M | R₁R₄ | R₂R₃ | R₅R₈ | R₆R₇ |
|---|---|---|---|---|---|
| 196 | Cu | H, H | —SO₂NH-[pyridin-2,6-diyl]-NHSO₂-[3-SO₃Li-phenyl] | H, H | —SO₂NH-[pyridin-2,6-diyl]-NHSO₂-[3-SO₃Li-phenyl] |
| 197 | Cu | H, H | —SO₂NH-[pyrazin-2,6-diyl]-NHCO-[3-SO₃Li-phenyl] | H, H | —SO₂NH-[pyrazin-2,6-diyl]-NHCO-[3-SO₃Li-phenyl] |
| 198 | Cu | H, H | | H, H | |

TABLE 17-continued
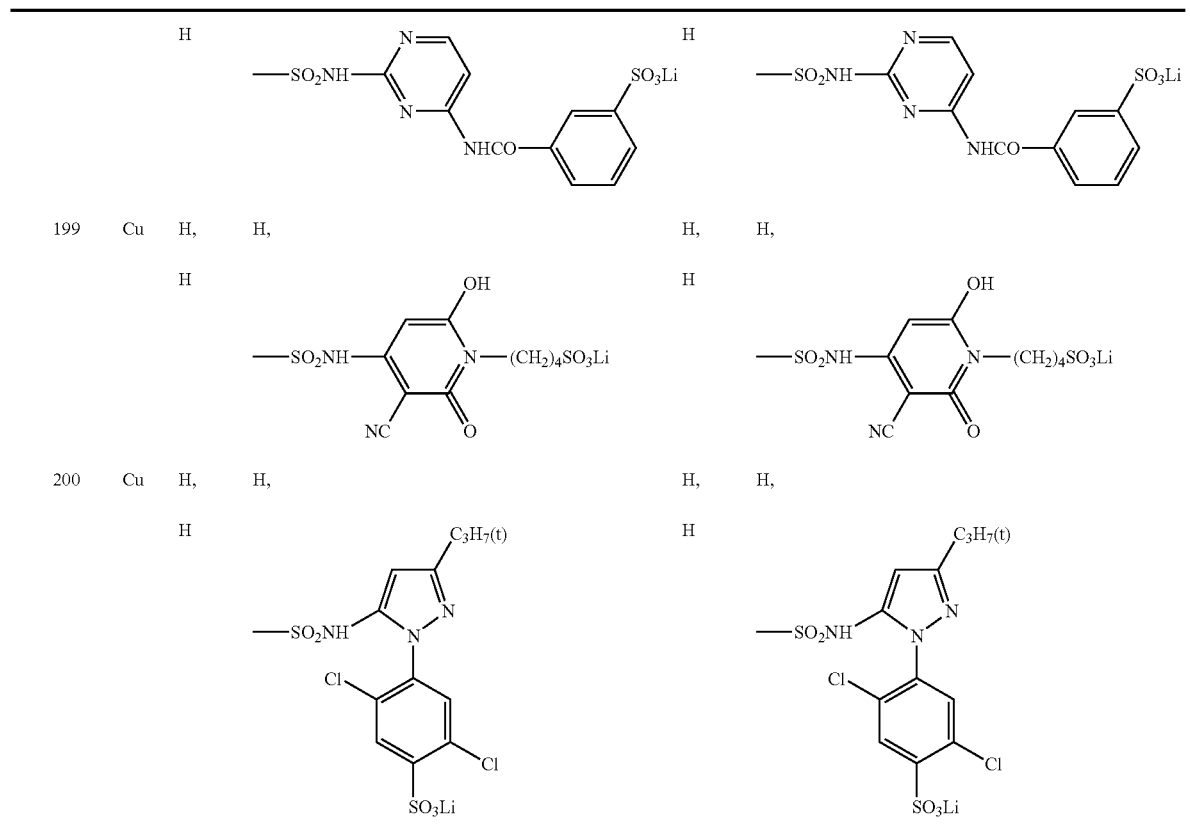
| Compound | $R_9R_{12}$ | $R_{10}R_{11}$ | $R_{13}R_{16}$ | $R_{14}R_{15}$ |
|---|---|---|---|---|
| 196 | H, H | H, —SO$_2$NH-(pyridine)-NHSO$_2$-(phenyl-SO$_3$Li) | H, H | H, —SO$_2$NH-(pyridine)-NHSO$_2$-(phenyl-SO$_3$Li) |
| 197 | H, H | H, —SO$_2$NH-(pyrimidine)-NHCO-(phenyl-SO$_3$Li) | H, H | H, —SO$_2$NH-(pyrimidine)-NHCO-(phenyl-SO$_3$Li) |
| 198 | H, H | H, —SO$_2$NH-(pyrimidine)-NHCO-(phenyl-SO$_3$Li) | H, H | H, —SO$_2$NH-(pyrimidine)-NHCO-(phenyl-SO$_3$Li) |
| 199 | H, | H, | H, | H, |

TABLE 17-continued

| | | | | | |
|---|---|---|---|---|---|
| | H | —SO$_2$NH-[6-OH,3-CN,2-oxo-1-(CH$_2$)$_4$SO$_3$Li pyridin-4-yl] | | H | —SO$_2$NH-[6-OH,3-CN,2-oxo-1-(CH$_2$)$_4$SO$_3$Li pyridin-4-yl] |
| 200 | H, | H, | | H, | H, |
| | H | —SO$_2$NH-[3-C$_3$H$_7$(t),1-(2,5-dichloro-4-SO$_3$Li-phenyl)pyrazol-5-yl] | | H | —SO$_2$NH-[3-C$_3$H$_7$(t),1-(2,5-dichloro-4-SO$_3$Li-phenyl)pyrazol-5-yl] |

TABLE 18

| Compound | M | R$_1$R$_4$ | R$_2$R$_3$ | R$_5$R$_8$ | R$_6$R$_7$ |
|---|---|---|---|---|---|
| 201 | Cu | H, | H, | H, | H, |
| | | H | —SO$_2$NH-[5-OH,1-(2-SO$_3$Li-benzyl)pyrazol-3-yl] | H | —SO$_2$NH-[5-OH,1-(2-SO$_3$Li-benzyl)pyrazol-3-yl] |
| 202 | Cu | H, | H, | H, | H, |
| | | H | —SO$_2$NH-[3-(3-SO$_3$Li-phenyl),1-(2,6-dichloro-4-CO$_2$Li-phenyl)pyrazol-5-yl] | H | —SO$_2$NH-[3-(3-SO$_3$Li-phenyl),1-(2,6-dichloro-4-CO$_2$Li-phenyl)pyrazol-5-yl] |
| 203 | Cu | H, | H, | H, | H, |

TABLE 18-continued

| Compound | | | | | | |
|---|---|---|---|---|---|---|
| | H | | [pyrazole with SC₂H₄SO₃Li, SO₂NH, phenyl-CO₂Li] | H | | [pyrazole with SC₂H₄SO₃Li, SO₂NH, phenyl-CO₂Li] |
| 204 | Cu | H, | H, H | H, | H, | |
| | | H | [benzisothiazole-SO₂NH, CO₂Li] | H | [benzisothiazole-SO₂NH, CO₂Li] | |
| 205 | Cu | H, | H, H | H, | H, | |
| | | H | [benzothiazole-SO₂NH, CO₂Li] | H | [benzothiazole-SO₂NH, CO₂Li] | |

| Compound | $R_9R_{12}$ | $R_{10}R_{11}$ | | $R_{13}R_{16}$ | $R_{14}R_{15}$ | |
|---|---|---|---|---|---|---|
| 201 | H, | H, | | H, | H, | |
| | | H | [SO₂NH-pyrazol-OH with CH₂-phenyl-SO₃Li] | H | [SO₂NH-pyrazol-OH with CH₂-phenyl-SO₃Li] | |
| 202 | H, | H, | | H, | H, | |
| | | H | [SO₂NH-pyrazole with phenyl-SO₃Li and dichlorophenyl-CO₂Li] | H | [SO₂NH-pyrazole with phenyl-SO₃Li and dichlorophenyl-CO₂Li] | |
| 203 | H, | H, | | H, | H, | |

TABLE 18-continued

| | | | | |
|---|---|---|---|---|
| | H | —SO₂NH— [pyrazole with SC₂H₄SO₃Li, phenyl-CO₂Li] | H | —SO₂NH— [pyrazole with SC₂H₄SO₃Li, phenyl-CO₂Li] |
| 204 | H, H | —SO₂NH— [benzoisothiazole-CO₂Li] | H, H | —SO₂NH— [benzoisothiazole-CO₂Li] |
| 205 | H, H | —SO₂NH— [benzothiazole-CO₂Li] | H, H | —SO₂NH— [benzothiazole-CO₂Li] |

TABLE 19

| Compound | M | R₁R₄ | R₂R₃ | R₅R₈ | R₆R₇ |
|---|---|---|---|---|---|
| 206 | Cu | H, Cl | —SO₂NH— [pyrazole with SC₂H₄SO₂Li, phenyl-CO₂Li] | H, Cl | —SO₂NH— [pyrazole with SC₂H₄SO₂Li, phenyl-CO₂Li] |
| 207 | Cu | H, SCH₃ | —SO₂NH— [pyrazole with SC₂H₄SO₂Li, phenyl-CO₂Li] | H, SCH₃ | —SO₂NH— [pyrazole with SC₂H₄SO₂Li, phenyl-CO₂Li] |

TABLE 19-continued

| Compound | | | | | | |
|---|---|---|---|---|---|---|
| 208 | Cu | H, | H, Cl | [structure: —SO₂NH-pyrazole-OH with phenyl-SO₃Li] | H, Cl | [structure: —SO₂NH-pyrazole-OH with phenyl-SO₃Li] |
| 209 | Ni | H, | H, H | [structure: —SO₂NH-pyrazole-OH with phenyl-CO₂Li] | H, H | [structure: —SO₂NH-pyrazole-OH with phenyl-CO₂Li] |
| 210 | Zn | H, | H, H | [structure: —SO₂NH-benzisothiazole-CO₂Li] | H, H | [structure: —SO₂NH-benzisothiazole-CO₂Li] |

| Compound | R₉R₁₂ | R₁₀R₁₁ | | R₁₃R₁₆ | R₁₄R₁₅ |
|---|---|---|---|---|---|
| 206 | H, | H, Cl | [structure: pyrazole with SC₂H₄SO₂Li and —SO₂NH, phenyl-CO₂Li] | H, Cl | [structure: pyrazole with SC₂H₄SO₂Li and —SO₂NH, phenyl-CO₂Li] |

TABLE 19-continued

| 207 | H, | H, | | H, | H, |
|---|---|---|---|---|---|
| | SCH₃ | —SO₂NH-[pyrazole with SC₂H₄SO₂Li at 3-position, N-(4-CO₂Li-phenyl)] | SCH₃ | | —SO₂NH-[pyrazole with SC₂H₄SO₂Li at 3-position, N-(4-CO₂Li-phenyl)] |
| 208 | H, | H, | | H, | H, |
| | Cl | —SO₂NH-[3-position of pyrazole, 5-OH, N-(4-SO₃Li-phenyl)] | | Cl | —SO₂NH-[3-position of pyrazole, 5-OH, N-(4-SO₃Li-phenyl)] |
| 209 | H, | H, | | H, | H, |
| | H | —SO₂NH-[3-position of pyrazole, 5-OH, N-(4-CO₂Li-phenyl)] | | H | —SO₂NH-[3-position of pyrazole, 5-OH, N-(4-CO₂Li-phenyl)] |
| 210 | H, | H, | | H, | H, |
| | H | —SO₂NH-[2,1-benzisothiazol-3-yl, 6-CO₂Li] | | H | —SO₂NH-[2,1-benzisothiazol-3-yl, 6-CO₂Li] |

TABLE 20

| Compound | M | R₁R₄ R₂R₃ | | R₅R₈ R₆R₇ | |
|---|---|---|---|---|---|
| 211 | Cu | H, H | H, [3-methyl-pyrazole-SO₂NH- with phenyl bearing SO₃Li at 2,5-positions] | H, H | [same as left: 3-methyl-pyrazole-SO₂NH- with phenyl bearing SO₃Li at 2,5-positions] |
| 212 | Cu | H, H | [4-bromo-pyrazole-SO₂NH- with 2,6-dichloro-4-sulfonato(Li) phenyl] | H, H | [same structure] |
| 213 | Cu | H, H | [pyrazole-SO₂NH- with 2,5-dichloro-4-sulfonato(Li) phenyl] | H, H | [same structure] |
| 214 | Cu | H, H | [4-cyano-pyrazole-SO₂NH- with 2,6-dichloro-4-sulfonato(Li) phenyl] | H, H | [same structure] |
| 215 | Cu | H, H | | H, H | |

TABLE 20-continued
| Compound | R9R12 | R10R11 | R13R16 | R14R15 |
|---|---|---|---|---|
| | H, H | H, 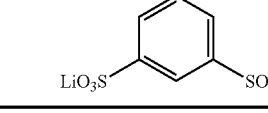 | | H, 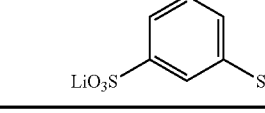 |
| 211 | H, H | H, 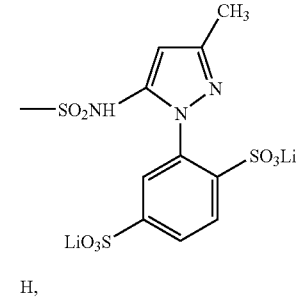 | H, HJ | H, 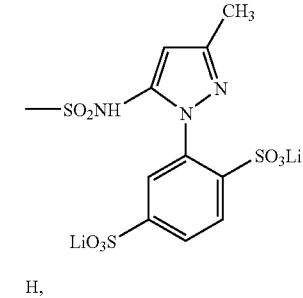 |
| 212 | H, H | H, 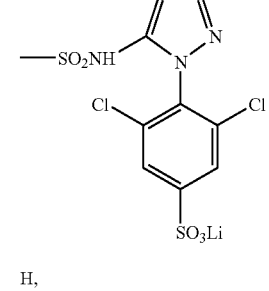 | H, H | H, 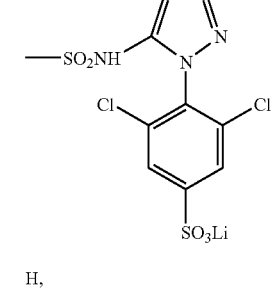 |
| 213 | H, H | H, 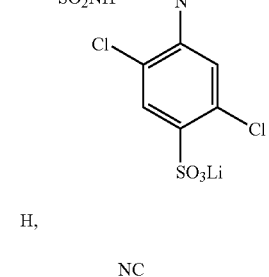 | H, H | H, 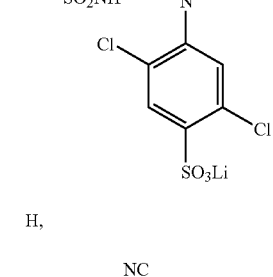 |
| 214 | H, H | H, 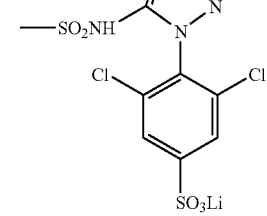 | H, H | H, 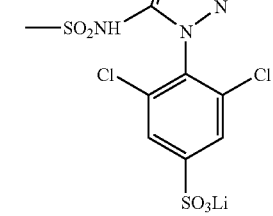 |

TABLE 20-continued

215 H, H, H, H,
H

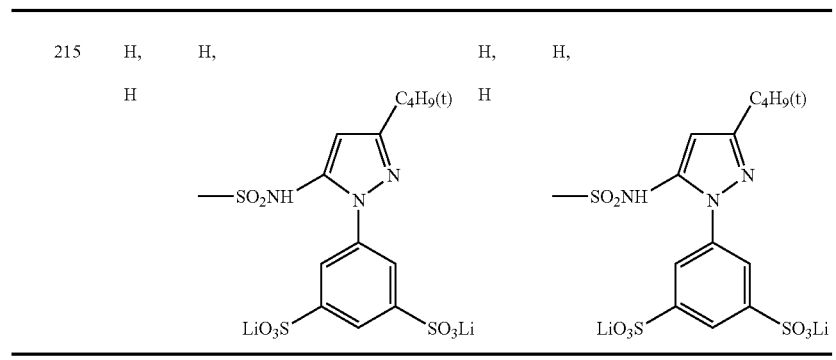

Examples of the use of the phthalocyanine compound of the present invention include a material for forming an image, particularly a color image. Specific examples thereof include an ink jet recording material which is described in detail later, a heat-sensitive transfer-type image recording material, a pressure-sensitive recording material, a recording material using the electro-photographic system, a transfer-type silver halide light-sensitive material, a printing ink and a recording pen. Among these, preferred are an ink jet recording material, a heat-sensitive transfer-type image recording material and a recording material using the electrophotographic system, more preferred is an ink jet recording material. The phthalocyanine compound of the present invention can also be applied to a dyeing solution for dyeing various fibers of color filter used in solid image camera element such as LCD and CCD described in U.S. Pat. No. 4,808,501 and JP-A-6-35182.

The compound of the present invention can be adjusted to have physical properties suitable for use, such as solubility and heat transfer, by the substituent. Furthermore, the compound of the present invention can be used in a uniformly dissolved state, a dispersed and dissolved state such as emulsification dispersion, or a solid dispersion state according to the system where the compound is used.

The ink for ink jetting comprising the ink of the present invention is described below. The ink for ink jetting can be produced by dissolving and/or dispersing the above-described phthalocyanine compound in a lipophilic or aqueous medium. Preferably, an aqueous medium is used. If desired, other additives are contained within the range of not impairing the effect of the present invention. Examples of other additives include known additives such as drying inhibitor (wetting agent), discoloration inhibitor, emulsification stabilizer, permeation accelerator, ultraviolet absorbent, antiseptic, fungicide, pH adjusting agent, surface tension adjusting agent, defoaming agent, viscosity controlling agent, dispersant, dispersion stabilizer, rust inhibitor and chelating agent. These various additives are directly added to the ink solution in the case of a water-soluble ink. When an oil-soluble dye is used in the form of a dispersion, the additives are generally added to the dispersion after the preparation of a dye dispersion, but may be added to the oil or aqueous phase at the preparation.

The drying inhibitor is suitably used for the purpose of preventing occurrence of clogging due to drying of the ink for ink jetting at the ink jetting port of a nozzle used for the ink jet recording system.

The drying inhibitor is preferably a water-soluble organic solvent having a vapor pressure lower than water. Specific examples thereof include polyhydric alcohols represented by ethylene glycol, propylene glycol, diethylene glycol, polyethylene glycol, thiodiglycol, dithiodiglycol, 2-methyl-1,3-propanediol, 1,2,6-hexanetriol, acetylene glycol derivative, glycerin and trimethylol-propane; lower alkyl ethers of polyhydric alcohol, such as ethylene glycol monomethyl(or ethyl) ether, diethylene glycol monomethyl(or ethyl) ether and triethylene glycol monoethyl(or butyl) ether; heterocyclic rings such as 2-pyrrolidone, N-methyl-2-pyrrolidone, 1,3-dimethyl-2-imidazolidinone and N-ethylmorpholine; sulfur-containing compounds such as sulfolane, dimethylsulfoxide and 3-sulfolene; polyfunctional compounds such as diacetone alcohol and diethanolamine; and urea derivatives. Among these, polyhydric alcohols such as glycerin and diethylene glycol are preferred. These drying inhibitors may be used individually or in combination of two or more thereof. The drying inhibitor is preferably contained in the ink in an amount of 10 to 50 wt %.

The permeation accelerator is suitably used for the purpose of obtaining good permeation of the ink for ink jetting into paper. Examples of the permeation accelerator which can be used include alcohols such as ethanol, isopropanol, butanol, di(tri)ethylene glycol monobutyl ether and 1,2-hexanediol, sodium laurylsulfate, sodium oleate and non-ionic surfactants. A sufficiently high effect can be obtained by adding from 5 to 30 wt % of the permeation accelerator to the ink. The permeation accelerator is preferably used within the amount range of causing no blurring of printed letter or no print through.

The ultraviolet absorbent is used for the purpose of improving the storability of image. Examples of the ultraviolet absorbent which can be used include benzotriazole-base compounds described in JP-A-58-185677, JP-A-61-190537, JP-A-2-782, JP-A-5-197075 and JP-A-9-34057, benzophenone-base compounds described in JP-A-46-2784, JP-A-5-194483 and U.S. Pat. No. 3,214,463, cinnamic acid-base compounds described in JP-B-48-30492, JP-B-56-21141 and JP-A-10-88106, triazine-base compounds described in JP-A-4-298503, JP-A-8-53427, JP-A-8-239368, JP-A-10-182621 and Japanese Unexamined Published International Application 8-501291, compounds described in *Research Disclosure* No. 24239, and compounds of absorbing ultraviolet light and emitting fluorescent light, so-called fluorescent brightening agents represented by stilbene-base compound and benzoxazole-base compound.

The discoloration inhibitor is used for the purpose of improving the storability of image. Examples of the discoloration inhibitor which can be used include various organic discoloration inhibitors and metal complex-base discoloration inhibitors. Examples of the organic discoloration inhibitor include hydroquinones, alkoxy-phenols, dialkoxyphenols, phenols, anilines, amines, indanes, chromans, alkoxyanilines and heterocyclic rings. Examples of the metal complex include nickel complex and zinc complex. More specifically, compounds described in patents cited in *Research Disclosure*, Nos. 17643 (Items VII-I to VII-J), 15162, 18716 (page 650, left column) 36544 (page 527), 307105 (page 872) and 15162, and compounds included in formulae of representative compounds and in exemplary compounds described in JP-A-62-215272 (pages 127 to 137) can be used.

Examples of the fungicide include sodium dehydroacetate, sodium benzoate, sodium pyridinethione-1-oxide, ethyl p-hydroxybenzoate, 1,2-benzisothiazolin-3-one and salts thereof. The fungicide is preferably used in the ink in an amount of 0.02 to 1.00 wt %.

As the pH adjusting agent, the above-described neutralizer (e.g., organic base, inorganic alkali) can be used. The pH adjusting agent is used for the purpose of improving the storage stability of the ink for ink jetting and is preferably added to adjust the ink for ink jetting to a pH of 6 to 10, more preferably to a pH of 7 to 10.

The surface tension adjusting agent includes nonionic, cationic and anionic surfactants. Here, the surface tension of the ink for ink jetting of the present invention is preferably from 25 to 70 mN/m, more preferably from 25 to 60 mN/m. Also, the viscosity of the ink for ink jetting of the present invention is preferably 30 mPas or less, more preferably 20 mPa·s or less. Preferred examples of the surfactant include anionic surfactants such as fatty acid salt, alkylsulfuric acid ester salt, alkylbenzenesulfonate, alkylnaphthalenesulfonate, dialkylsulfosuccinate, alkylphosphoric acid ester salt, naphthalenesulfonic acid formalin condensate and polyoxyethylenealkylsulfuric acid ester salt, and nonionic surfactants such as polyoxyethylene alkyl ether, polyoxyethylene alkylallyl ether, polyoxyethylene fatty acid ester, sorbitan fatty acid ester, polyoxyethylene sorbitan fatty acid ester, polyoxyethylene alkylamine, glycerin fatty acid ester and oxyethylene oxypropylene block copolymer. Also, SURFYNOLS (produced by Air Products & Chemicals), which is an acetylene-base polyoxyethylene oxide surfactant, is preferably used. In addition, amine oxide-type amphoteric surfactants such as N,N-dimethyl-N-alkylamine oxide are preferred. Furthermore, surfactants described in JP-A-59-157636 (pages (37) to (38)) and *Research Disclosure*, No. 308119 (1989) can be used.

As the defoaming agent, for example, a chelating agent represented by the fluorine- or silicon-containing compound and EDTA can also be used, if desired.

In the case of dispersing the phthalocyanine compound of the present invention in an aqueous medium, a colored fine particle containing the dye and an oil-soluble polymer is preferably dispersed in an aqueous medium as described in JP-A-11-286637, JP-A-2001-240763, JP-A-2001-262039 and JP-A-2001-247788 or the phthalocyanine compound of the present invention dissolved in a high boiling point organic solvent is preferably dispersed in an aqueous medium as described in JP-A-2001-262018, JP-A-2001-240763, JP-A-2001-335734 and JP-A-2002-80772.

With respect to the specific method for dispersing the phthalocyanine compound of the present invention in an aqueous medium, the oil-soluble polymer, high boiling point organic solvent and additives used, and the amounts thereof, those described in the above patent publications can be preferably used. Also, the azo compound, which is solid, can be dispersed as it is in a fine particle state. At the dispersion, a dispersant or a surfactant can be used. As for the dispersing device, a simple stirrer, an impeller stirring system, an in-line stirring system, a mill system (e.g., colloid mill, ball mill, sand mill, attritor, roll mill, agitator mill), an ultrasonic wave system and a high-pressure emulsification dispersion system (high-pressure homogenizer and as the commercially available device, specific examples thereof include Gaulin Homogenizer, Microfluidizer and DeBEE 2000) can be used. The preparation method of the ink for ink jetting is described in detail, in addition to the above patent publications, in JP-A-5-148436, JP-A-5-295312, JP-A-7-97541, JP-A-7-82515, JP-A-7-118584, JP-A-11-286637 and JP-A-2001-271003 and the contents described in these patent publications can be used also for the preparation of the ink for ink jetting of the present invention.

As the aqueous medium, a mixture comprising water as the main component and a water-miscible organic solvent added, if desired, can be used. Examples of the water-miscible organic solvent include alcohols (e.g., methanol, ethanol, propanol, isopropanol, butanol, isobutanol, sec-butanol, tert-butanol, pentanol, hexanol, cyclohexanol, benzyl alcohol), polyhydric alcohols (e.g., ethylene glycol, diethylene glycol, triethylene glycol, polyethylene glycol, propylene glycol, dipropylene glycol, polypropylene glycol, butylene glycol, hexanediol, pentanediol, glycerin, hexanetriol, thiodiglycol), glycol derivatives (e.g., ethylene glycol monomethyl ether, ethylene glycol monoethyl ether, ethylene glycol monobutyl ether, diethylene glycol, monomethyl ether, diethylene glycol monobutyl ether, propylene glycol monomethyl ether, propylene glycol monobutyl ether, dipropylene glycol monomethyl ether, triethylene glycol monomethyl ether, ethylene glycol diacetate, ethylene glycol monomethyl ether acetate, triethylene glycol monomethyl ether, triethylene glycol, monoethyl ether, ethylene glycol monophenyl ether), amines (e.g., ethanolamine, diethanolamine, triethanolamine, N-methyldiethanolamine, N-ethyldiethanolamine, morpholine, N-ethylmorpholine, ethylenediamine, diethylenetriamine, triethylenetetramine, polyethyleneimine, tetramethyl-propylenediamine) and other polar solvents (e.g., formamide, N,N-dimethylformamide, N,N-dimethylacetoamide, dimethylsulfoxide, sulfolane, 2-pyrrolidone, N-methyl-2-pyrrolidone, N-vinyl-2-pyrrolidone, 2-oxazolidone, 1,3-dimethyl-2-imidazolidinone, acetonitrile, acetone). These water-miscible organic solvents can be used in combination of two or more thereof.

In 100 parts by weight of the ink or ink for ink jetting of the present invention, from 0.2 to 10 parts by weight of the phthalocyanine compound is preferably contained. Furthermore, in the ink for ink jetting of the present invention, other coloring agent may be used in combination with the phthalocyanine compound. In the case of using two or more coloring agents in combination, the total content of the coloring agents is preferably in the above-described range.

The ink for ink jetting of the present invention can be used not only for the formation of a monochromatic image but also for the formation of a full color image. For forming a full color image, a magenta color tone ink, a cyan color tone ink and a yellow color tone ink can be used. Also, for adjusting the color tone, a black color tone ink may be further used. In these inks, other coloring material (dye or pigment) may also be used in addition to the phthalocyanine compound of the present invention so as to improve the image reproducing performance.

The yellow dye which can be used together with the phthalocyanine compound of the present invention may be any yellow dye. Examples thereof include aryl- or heteryl-azo dyes having a phenol, a naphthol, an aniline, a heterocyclic ring (e.g., pyrazolone, pyridone), an open chain-type active methylene compound or the like as the coupling component (hereinafter referred to as "coupler component"); azomethine dyes having an open chain-type active methylene compound or the like as the coupler component; methine dyes such as benzylidene dye and monomethine oxonol dye; and quinone-base dyes such as naphthoquinone dye and anthraquinone dye. Other examples of the dye species include quinophthalone dye, nitro-nitroso dye, acridine dye and acridinone dye.

The magenta dye which can be used may be any magenta dye. Examples thereof include aryl- or heteryl-azo dyes having a phenol, a naphthol or an aniline as the coupler component; azomethine dyes having a pyrazolone or a pyrazolotriazole as the coupler component; methine dyes such as arylidene dye, styryl dye, merocyanine dye, cyanine dye and oxonol dye; carbonium dyes such as diphenylmethane dye, triphenylmethane dye and xanthene dye; quinone dyes such as naphthoquinone, anthraquinone and anthrapyridone; and condensed polycyclic dyes such as dioxazine dye.

The cyan dye which can be used may be any cyan dye. Examples thereof include aryl- or heteryl-azo dyes having a phenol, a naphthol or an aniline as the coupler component; azomethine dyes having a phenol, a naphthol or a heterocyclic ring (e.g., pyrrolotriazole) as the coupler component; polymethine dyes such as cyanine dye, oxonol dye and merocyanine dye; carbonium dyes such as diphenylmethane dye, triphenylmethane dye and xanthene dye; phthalocyanine dyes; anthraquinone dyes; and indigo-thioindigo dyes.

These dyes may be a dye which provides a yellow, magenta or cyan color for the first time when a part of the chromophore is dissociated. In this case, the counter cation may be an inorganic cation such as alkali metal and ammonium, an organic cation such as pyridinium and quaternary ammonium salt, or a polymer cation having such a cation as a partial structure.

Examples of the black coloring material which can be used include dis-azo, tris-azo and tetra-azo dyes and a dispersion of carbon black.

[Ink Jet Recording Method]

According to the ink jet recording method of the present invention, an energy is provided to the ink for ink jetting and thereby an image is formed on a known image-receiving material, namely, plain paper, resin coated paper, ink jet special paper described, for example, in JP-A-8-169172, JP-A-8-27693, JP-A-2-276670, JP-A-7-276789, JP-A-9-323475, JP-A-62-238783, JP-A-10-153989, JP-A-10-217473, JP-A-10-235995, JP-A-10-337947, JP-A-10-217597 and JP-A-10-337947, film, electrophotographic common paper, cloth, glass, metal, ceramic or the like.

In forming an image, a polymer latex compound may be used in combination for the purpose of giving glossiness or water resistance or improving the weather resistance. The timing of imparting the latex compound to the image-receiving material may be before or after imparting the coloring agent or simultaneously with it. Accordingly, the site to which added may be in the image-receiving paper or ink or a liquid material composed of the polymer latex alone may be prepared and used. More specifically, the methods described in JP-A-2002-166638, JP-A-2002-121440, JP-A-2002-154201, JP-A-2002-144696, JP-A-2002-80759, JP-A-2002-187342 and JP-A-2002-172774 can be preferably used.

The recording paper and recording film used in the ink jet printing using the ink of the present invention are described below. The support which can be used for the recording paper or film is produced, for example, from a chemical pulp such as LBKP and NBKP, a mechanical pulp such as GP, PGW, RMP, TMP, CTMP, CMP and CGP, a waste paper pulp such as DIP, or the like by mixing, if desired, additives such as conventionally known pigment, binder, sizing agent, fixing agent, cation agent and paper strength increasing agent and then sheeting the mixture using various devices such as Fourdrinier paper machine and cylinder paper machine. Other than this support, synthetic paper or plastic film may be used. The thickness of the support is preferably from 10 to 250 µm and the basis weight is preferably from 10 to 250 g/m². An ink-accepting layer (i.e., ink-receiving layer) and a backcoat layer may be provided on the support as it is or may be provided after providing a size press or anchor coat layer using starch, polyvinyl alcohol and the like. The support may also be subjected to a flattening treatment (e.g., smoothing treatment) by a calendering device such as machine calender, TG calender and soft calender. In the present invention, the support is preferably paper or plastic film of which both surfaces are laminated with polyolefin (for example, polyethylene, polystyrene, polyethylene terephthalate, polybutene or a copolymer thereof). In the polyolefin, a white pigment (for example, titanium oxide or zinc oxide) or a tinting dye (for example, cobalt blue, ultramarine or neodymium oxide) is preferably added.

The ink-accepting layer (i.e., ink-receiving layer) provided on the support contains a pigment and an aqueous binder. The pigment is preferably a white pigment. The white pigment includes a white inorganic pigment such as calcium carbonate, kaolin, talc, clay, diatomaceous earth, synthetic amorphous silica, aluminum silicate, magnesium silicate, calcium silicate, aluminum hydroxide, alumina, lithopone, zeolite, barium sulfate, calcium sulfate, titanium dioxide, zinc sulfide and zinc carbonate, and an organic pigment such as styrene-base pigment, acryl-base pigment, urea resin and melamine resin. The white pigment contained in the ink-accepting layer is preferably a porous inorganic pigment, more preferably a synthetic amorphous silica having a large pore area. The synthetic amorphous silica may be either a silicic acid anhydride obtained by a dry production method or a silicic acid hydrate obtained by a wet production method but is preferably a silicic acid hydrate.

Examples of the aqueous binder contained in the ink-accepting layer include water-soluble polymers such as polyvinyl alcohol, silanol-modified polyvinyl alcohol, starch, cationized starch, casein, gelatin, carboxymethyl cellulose, hydroxyethyl cellulose, polyvinylpyrrolidone, polyalkylene oxide and polyalkylene oxide derivative, and water-dispersible polymers such as styrene butadiene latex and acryl emulsion. These aqueous binders can be used individually or in combination of two or more thereof. Among these, polyvinyl alcohol and silanol-modified polyvinyl alcohol are preferred in view of attaching property (i.e., adhesive property) to the pigment and peeling resistance of the ink-accepting layer.

The ink-accepting layer may contain a mordant, a waterproofing agent, a light fastness enhancer, a surfactant and other additives in addition to the pigment and the aqueous binder.

The binder added to the ink-accepting layer is preferably immobilized and for this purpose, a polymer mordant is preferably used.

The polymer mordant is described in JP-A-48-28325, JP-A-54-74430, JP-A-54-124726, JP-A-55-22766, JP-A-55-142339, JP-A-60-23850, JP-A-60-23851, JP-A-60-23852, JP-A-60-23853, JP-A-60-57836, JP-A-60-60643, JP-A-60-118834, JP-A-60-122940, JP-A-60-122941, JP-A-60-122942, JP-A-60-235134, JP-A-1-161236 and U.S. Pat. Nos. 2,484,430, 2,548,564, 3,148,061, 3,309,690, 4,115,124, 4,124,386, 4,193,800, 4,273,853, 4,282,305 and 4,450,224. An image-receiving material containing the polymer mordant described in JP-A-1-161236 (pages 212 to 215) is particularly preferred. When the polymer mordant described in this patent publication is used, an image having excellent image quality can be obtained and at the same time, light fastness of the image is improved.

The water-proofing agent is effective for water-proofing the image. The water-proofing agent is preferably a cationic resin. Examples of the cationic resin include polyamidopolyamine epichlorohydrin, polyethyleneimine, polyaminesulfone, poly-dimethyldiallylammonium chloride, cation polyacrylamide and colloidal silica. Among these cationic resins, polyamidopolyamine epichlorohydrin is preferred. The content of the cationic resin is preferably from 1 to 15 wt %, more preferably from 3 to 10 wt %, based on the entire solid content of the ink-accepting layer.

Examples of the light fastness enhancer include zinc sulfate, zinc oxide, hindered amine-base antioxidants and benzophenone-base or benzotriazole-base ultraviolet absorbents. Among these, zinc sulfate is preferred.

The surfactant functions as a coating aid, a peeling property improver, a sliding property improver or an antistatic agent. The surfactant is described in JP-A-62-173463 and JP-A-62-183457. In place of the surfactant, an organic fluoro compound may be used. The organic fluoro compound is preferably hydrophobic. Examples of the organic fluoro compound include a fluorine-containing surfactant, an oily fluorine-base compound (for example, fluorine oil) and a solid fluorine compound resin (for example, ethylene tetrafluoride resin). The organic fluoro compound is described in JP-B-57-9053 (columns 8 to 17), JP-A-61-20994 and JP-A-62-135826. Other additives added to the ink-accepting layer include a pigment dispersant, a thickener, a defoaming agent, a dye, a fluorescent brightening agent, an antiseptic, a pH adjusting agent, a matting agent, a hardening agent and the like. The ink-accepting layer may be either one layer or two layers.

In the recording paper or film, a backcoat layer may also be provided. Examples of the component which can be added to this layer include a white pigment, an aqueous binder and other components. Examples of the white pigment contained in the backcoat layer include white inorganic pigments such as precipitated calcium carbonate, heavy calcium carbonate, kaolin, talc, calcium sulfate, barium sulfate, titanium dioxide, zinc oxide, zinc sulfide, zinc carbonate, satin white, aluminum silicate, diatomaceous earth, calcium silicate, magnesium silicate, synthetic amorphous silica, colloidal silica, colloidal alumina, pseudo-boehmite, aluminum hydroxide, alumina, lithopone, zeolite, hydrolyzed halloysite, magnesium carbonate and magnesium hydroxide, and organic pigments such as styrene-base plastic pigment, acryl-base plastic pigment, polyethylene, microcapsule, urea resin and melamine resin.

Examples of the aqueous binder contained in the backcoat layer include water-soluble polymers such as styrene/maleate copolymer, styrene/acrylate copolymer, polyvinyl alcohol, silanol-modified polyvinyl alcohol, starch, cationized starch, casein, gelatin, carboxymethyl cellulose, hydroxyethyl cellulose and polyvinylpyrrolidone, and water-dispersible polymers such as styrene butadiene latex and acryl emulsion. Other components contained in the backcoat layer include a defoaming agent, a foam inhibitor, a dye, a fluorescent brightening agent, an antiseptic, a water-proofing agent and the like.

A polymer latex may be added to a constituent layer (including the backcoat layer) of the ink jet recording paper or film. The polymer latex is used for the purpose of improving film properties, for example, stabilizing the dimension and preventing the curling, adhesion or film cracking. The polymer latex is described in JP-A-62-245258, JP-A-62-1316648 and JP-A-62-110066. When a polymer latex having a low glass transition temperature (40° C. or less) is added to a layer containing the mordant, the layer can be prevented from cracking or curling. Also, by adding a polymer latex having a high glass transition temperature to the backcoat layer, curling can be prevented.

The ink of the present invention is not limited on the ink jet recording system and is used in a known system, for example, an electric charge controlling system of ejecting out the ink by using the electrostatic induction force, a drop-on-demand system (pressure pulse system) of using an oscillation pressure of a piezo device, an acoustic ink jet system of converting electric signals into acoustic beams, irradiating the beams on the ink and ejecting out the ink using the radiation pressure, a thermal ink jet system of heating the ink to form bubbles and utilizing the generated pressure. The ink jet recording system includes a system of ejecting a large number of small volumes of so-called photo-ink having a low concentration, a system designed to improve the image quality by using a plurality of inks each having substantially the same hue but a different concentration, and a system of using colorless transparent ink.

EXAMPLES

Synthesis Example

The synthesis method of the dye mixture of the present invention is described in detail below by referring to Examples, however, the present invention is not limited to these Examples. In Examples, the temperature is in the centigrade scale.

A representative dye mixture of the present invention can be derived, for example, from the following synthesis route. In the following Examples, λmax means an absorption maximum wavelength and εmax means a molar absorption coefficient at the absorption maximum wavelength.

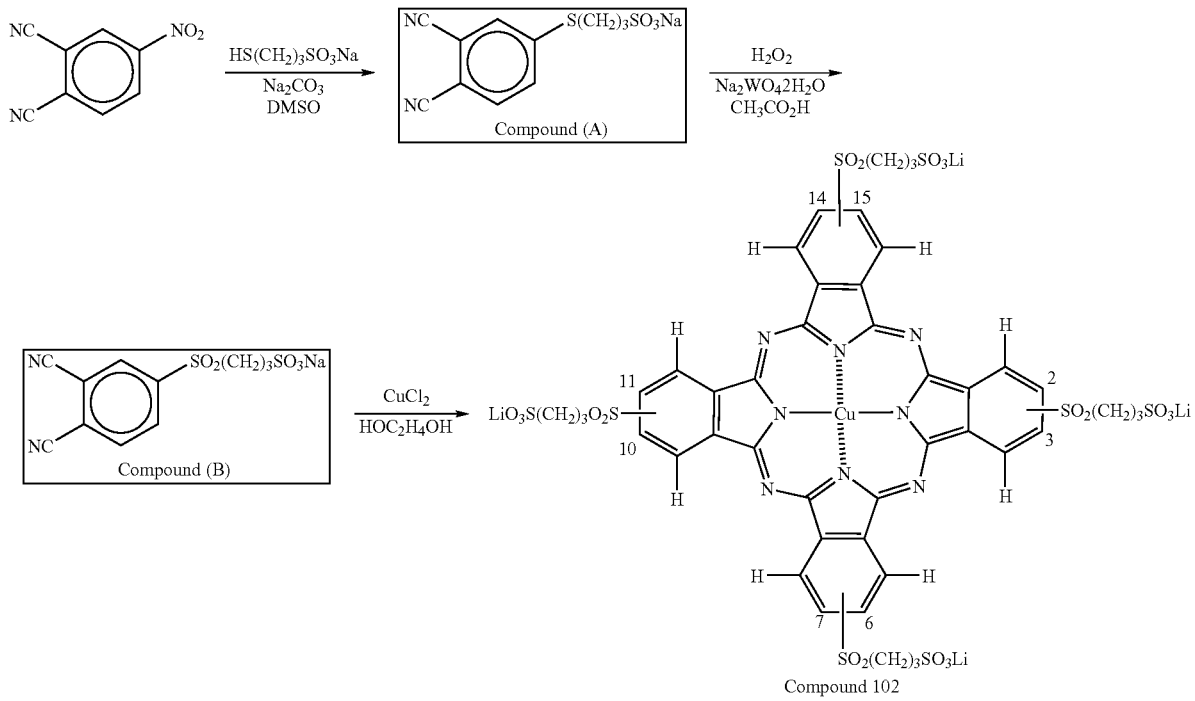

Compound 102

Synthesis Example 1

Synthesis of Compound A 26.0 g of 4-nitrophthalonitrile (produced by Tokyo Kasei) was dissolved in 200 mL of DMSO (dimethylsulfoxide) in a nitrogen stream and to the obtained solution under stirring at an inner temperature of 20° C., 30.3 g of sodium 3-mercapto-propane-sulfonate (produced by Aldrich) was added. To the resulting solution under stirring at an inner temperature of 20° C., 24.4 g of anhydrous sodium carbonate was gradually added. Subsequently, the reaction solution was heated to 30° C. while stirring and then stirred at the same temperature for 1 hour. After cooling to 20° C., the reaction solution was filtered by Nutsche, the filtrate was poured in 15,000 mL of ethyl acetate, thereby crystallizing, and then stirred at room temperature for 20 minutes, and the precipitated crude crystals were filtered by Nutsche, washed with ethyl acetate and dried. The obtained crude crystals were recrystallized from methanol/ethyl acetate to obtain 42.5 g of Compound A. $^1$H-NMR (DMSO-d6), δ value TMS standard: 1.9–2.0 (2H, t); 2.5–2.6 (2H, m); 3.2–3.3 (2H, t); 7.75–7.85 (1H, d); 7.93–8.03 (1H, d); 8.05–8.13 (1H, s).

Synthesis Example 2

Synthesis of Compound B 42.4 g of Compound 1 was dissolved in 300 mL of acetic acid and to the obtained solution under stirring at an inner temperature of 20° C., 2.5 g of $Na_2WO_4 \cdot 2H_2O$ was added. Thereafter, the solution was cooled to an inner temperature of 10° C. in ice bath. Thereto, 35 mL of aqueous hydrogen peroxide (30%) was gradually added dropwise while caring about heat generation. After stirring at an inner temperature of 15 to 20° C. for 30 minutes, the reaction solution was heated to an inner temperature of 60° C. and then stirred at the same temperature for 1 hour. After cooling to 20° C., the reaction solution was poured in 1,500 mL of ethyl acetate and then stirred at the same temperature for 30 minutes, and the precipitated crude crystals were filtered by Nutsche, washed with 200 mL of ethyl acetate and dried. The obtained crude crystals were washed under heat using methanol/ethyl acetate and thereby purified to obtain 41.0 g of Compound B. $^1$H—NMR (DMSO-d6), δ value TMS standard: 1.8–1.9 (2H, t); 2.4–2.5 (2H, m); 3.6–3.7 (2H, t); 8.3–8.4 (1H, d); 8.4–8.5 (1H, d); 8.6–8.7 (1H, s).

Synthesis Example 3

Synthesis of Compound 102 of the Present Invention

In a three-neck flask with a condenser tube, 40.36 g of compound B was dissolved in 80 mL of ethylene glycol at 80° C. in a nitrogen stream. While stirring, 4.0 g of cupric chloride (anhydride) was added and after elevating the inner temperature to 100° C., the solution was stirred at the same temperature for 2 hours, then cooled to an inner temperature of 60° C. Thereafter, 200 mL of methanol was gradually injected and then refluxed for 30 minutes. The inner temperature was lowered to room temperature and the precipitate was collected by filtration and washed with 150 mL of methanol. The obtained crude crystals were dissolved in 150 mL of an aqueous 0.1N LiOH solution, insoluble matters were separated by filtration and after elevating the inner temperature to 60° C., 50 mL of dimethylacetamide (DMAc) was injected thereto. While keeping the inner temperature at 80° C., 300 mL of ethanol was gradually added and then refluxed for 30 minutes. The inner temperature was lowered to room temperature and the precipitate was filtered and washed with heated methanol. This operation (addition of ethanol to an aqueous lithium hydroxide solution of the compound, and reprecipitation) was repeated twice. The purification was performed by gel permeation chromatography (SEPHADEX™ LH-20, produced by Pharmacia, developing solvent: water) to obtain 24.2 g of Compound 102. The compound was identified by the following method. Using mass spectrometry {LC/MS (Model TSQ-7000, LC: Model HP-1090); LC column (TSK-gelODS80Ts, 2×150 mm, detection: 580(±)20 nm & MCD); eluent and flow rate (water/methanol, 0.1% acetic acid/triethylamine buffer, 0.2 mL/min); LC/MS ionization; ESI-negative}, the analysis was performed from the peak of LC chromatogram and the MS spectrum. As a result, the obtained compound was confirmed as the objective phthalocyanine compound of the present invention. The counter cation M of the ionic hydrophilic group ($-SO_3M$) was determined by ion chromatography and atomic absorption method and found to be M=Li/Na=9/1. λmax=628.8 nm; εmax=64,100 (in $H_2O$).

The present invention is described below by referring to Examples, however, the present invention is not limited by these Examples.

Example 1

<Solubility>

32.8 mg,($2.0×10^{-5}$ mol) of Phthalocyanine Compound (171) of the present invention was weighed and deionized water was added thereto to make 100 ml. The resulting solution was stirred at 25° C. for 10 minutes to prepare a sample solution. In the same manner, a sample solution was prepared by using methanol as the water-miscible organic solvent in place of deionized water. Furthermore, samples solutions with a deionized aqueous solution or a methanol solution were prepared by using an equimolar amount of a phthalocyanine compound different only in the counter cation (counter cation: sodium ion, potassium ion or ammonium ion) from the compound of the present invention.

In the Table below, for example, 171-Na salt shown in the column of Compound No. means that the compound is a phthalocyanine compound having the same structure as Compound 171 but only the counter cation is changed to sodium. These phthalocyanine compounds having a predetermined counter cation were synthesized by using a raw material, intermediate or reaction agent having a predetermined counter salt in the case of compounds where the counter cation was lithium, sodium or potassium, and by exchanging the counter salt of the compound having a potassium salt in the case of compounds where the counter cation was ammonium. The kind and ratio of the counter cation were analyzed by ion chromatography and it was confirmed that in each compound, 90% or more of the counter cation was the predetermined counter cation.

The dissolution degree of each sample solution was determined by the following three methods: (1) the presence or absence of undissolved matters was judged with an eye, (2) after filtering through a microfilter having an average pore size of 0.25 μm, the presence or absence of undissolved matters on the filter was confirmed, and (3) the solution was filtered and measured on the absorption spectrum and when the absorbance obtained was only 90% or less of the absorbance calculated from the molar absorption coefficient, it was judged that insoluble matters were present in the sample solution. Sample solutions judged to have complete dissolution in all tests were rated ○, and sample solutions judged to have undissolved matters in any one test were rated X. The results are shown in Table.

<Spectral Absorption Property>

A 2 wt % aqueous solution of the phthalocyanine compound of the present invention was further 1,000-fold diluted with distilled water and the obtained solution was analyzed by a spectrophotometer under the following measurement conditions. The absorbance ratio b/a determined from the spectral absorption curve of the phthalocyanine compound used in Example is shown in Table below.

(Measuring Conditions)

Device used: Shimadzu Auto-Recording Spectro-photometer UV-260, cell: quartz cell, light path length: 10 mm, measuring temperature: 20° C., diluting solution: distilled water (pH: 7.0).

TABLE 21

| Compound No. | Counter Cation | Solvent | | b/a Value | |
| | | Deionized Water | Methanol | | |
|---|---|---|---|---|---|
| 171 | Li | ○ | ○ | 0.62 | Invention |
| 171-Na salt | Na | ○ | X | 0.64 | Comparison |
| 171-K salt | K | ○ | X | 0.63 | Comparison |
| 171-$NH_4$ salt | $NH_4$ | ○ | X | 0.54 | Comparison |

In phthalocyanine compounds having a spectral absorption curve satisfying the requirement specified in the present invention, the solubility in water is sufficiently high whichever counter cation the compound has. However, in methanol, only a phthalocyanine compound having lithium ion as the counter cation is dissolved. It is seen from this that in phthalocyanine compounds having the same structure, the solubility in a water-miscible organic solvent can be greatly improved only by changing the counter cation. It is also seen that even when the counter cation is changed, the spectral absorption property specified in the present invention is not greatly changed Example 2

Deionized water was added to the following components to make 1 liter and the resulting solution was stirred for 1 hour under heating at 30 to 40° C. Thereafter, the solution was adjusted to a pH of 9 with 10 mol/L of KOH and then filtered under pressure through a microfilter having an average pore size of 0.25 μm to prepare an ink solution for cyan color.

| Composition of Ink Solution A: | |
|---|---|
| Dye of the Present Invention (102) | 6.80 g |
| Diethylene glycol | 10.65 g |
| Glycerin | 14.70 g |
| Diethylene glycol monobutyl ether | 12.70 g |
| Triethanolamine | 0.65 g |
| Olefin E1010 | 0.9 g |

Ink Solutions B and C were prepared in the same manner as Ink Solution A except for changing the phthalocyanine compound as shown in Table below. As the ink solution for comparison, Comparative Ink Solutions 1 to 3 were prepared using phthalocyanine compounds where only the counter cation was changed as shown in the Table. Also, Comparative Ink Solution 4 was prepared by changing the phthalocyanine compound to a phthalocyanine compound (sodium salt) having a spectral absorption curve not satisfying the requirement specified in the present invention. In the Table, for example, 171-Na salt shown in the column of Compound No. means that the compound is a phthalocyanine compound having the same structure as Compound 171 and only the counter cation is changed to sodium.

When the dye was changed, a dye was used such that the amount added thereof became equimolar to Ink Solution A.

(Recording and Evaluation of Image)

Each ink for ink jetting of Examples (Ink Solutions A to C) and Comparative Examples (Comparative Ink Solutions 1 to 4) was subjected to the following evaluations. The results obtained are shown in Table 22. In the Table, "color tone", "paper dependency", "water resistance" and "light fastness" were evaluated after an image was recorded using each ink for ink jetting on a photo gloss paper (PM Photographic Paper "KOTAKU" (KA420PSK, EPSON), produced by EPSON) in an ink jet printer (PM-700C, manufactured by EPSON).

<Color Tone>

The image formed on the photo gloss paper was subjected to colorimetry of the reflection spectrum at intervals of 10 nm in the region from 390 to 730 nm and a* and b* were calculated based on the CIE (International Commission on Illumination) L*a*b* color space system.

By comparing with the standard cyan color sample (a color when solid batches of proof provided from 21 companies as members of the Japan Printing Machinery Manufacturers Association were subjected to colorimetry and the printing was performed using Japan Color Ink SF-90 and Japan Paper to give a smallest color difference (ΔE) from the average value) of JAPAN Color of JNC (Japan Printing Machinery Manufacturers Association), the preferred cyan color tone was defined as follows:

L*: in the range of 53.6±0.2,

○: a* (in the range of −35.9±6) and b* (in the range of −50.4±6)

Δ: only one of a* and b* (in the preferred region defined in ○ above)

X: neither a* nor b* (both out of the preferred region defined in ○ above)

The colorimetry values of the standard cyan color sample of JAPAN color used as the reference are shown below:

| L*: | 53.6 ± 0.2 |
|---|---|
| a*: | −37.4 ± 0.2 |
| b*: | −50.2 ± 0.2 |
| ΔE: | 0.4 (0.1 to 0.7) |

(1) Printer:

MANLORAND R-704, ink: JAPAN Color SF-90, paper: TOKUHISHI ART.

(2) Colorimetry:

Colorimeter: X-rite 938, 0/45, D50, 2 deg., black backing.

<Paper Dependency>

The image formed on the above-described photo gloss paper and the image separately formed on PPC plain paper were compared on the color tone. The evaluation was performed by the two-stage rating, that is, A (good) is when the difference between two images is small, and B (bad) is when the difference between two images is large.

<Water Resistance>

The photo gloss paper having formed thereon an image was dried at room temperature for 1 hour, dipped in deionized water for 10 seconds and then naturally dried at room temperature. The blurring was observed and evaluated by the three-stage rating, that is, A is no blurring, B is slight blurring and C is serious blurring.

<Light Fastness>

On the photo gloss paper having formed thereon an image, xenon light (85,000 lx) was irradiated for 7 days using a weather meter (Atlas Weather-o-meter C. I65, manufactured by Atlas (Illinois, U.S.A.)). The image density before and after the xenon irradiation was measured by a reflection densitometer (X-Rite 310TR) and evaluated as the dye residual percentage. The reflection density was measured at three points of 1, 1.5 and 2.0. The dye residual percentage was evaluated by the three-stage rating, that is, A is 70% or more at any density, B is less than 70% at one or two points, and C is less than 70% at all densities.

<Dark Heat Storability>

The photo gloss paper having formed thereon an image was stored for 7 days under the conditions of 80° C. and 15% RH. The image density before and after the storage was measured by a reflection densitometer (X-Rite 310TR) and evaluated as the dye residual percentage. The dye residual percentage was evaluated at three points having a reflection density of 1, 1.5 and 2.0. A is a dye residual percentage of 90% or more at any density, B is less than 90% at two points, and C is less than 90% at all densities.

<Ozone Gas Resistance>

In a box set to an ozone gas concentration of 0.5±0.1 ppm, room temperature and dark place using a Siemens-type ozonizer to which an a.c. voltage of 5 kV was applied while passing a dry air through the double glass tube, the photo gloss paper having formed thereon an image was left standing for 7 days. The image density before and after standing in an ozone gas atmosphere was measured by a reflection densitometer (X-Rite 310TR) and evaluated as the dye residual percentage. The reflection density was measured at three points of 1, 1.5 and 2.0. The ozone gas concentration in the box was set using an ozone gas monitor (Model OZG-EM-01) manufactured by APPLICS. The evaluation was performed by the three-stage rating, namely, A is a dye residual percentage of 70% or more at any density, B is less than 70% at one or two points, and C is less than 70% at all densities.

<Spectral Absorption Property>

The absorbance ratio b/a determined from the spectral absorption curve of phthalocyanine compound in the same manner as in the method of Example 1 is shown.

<Bronze Phenomenon>

The photo gloss paper having formed thereon an image was dried for 24 hours and then the presence or absence of generation of bronze phenomenon was observed with an eye and evaluated. A sample where the bronze phenomenon was not confirmed at all is rated ○, and a sample where the generation of bronze phenomenon was confirmed is rated X. Here, when a bronze phenomenon is generated, the printing density becomes lower than the case having no generation of a bronze phenomenon. Therefore, the generation of bronze phenomenon can also be confirmed by the decrease of printing density.

TABLE 22

| Ink Solution | Compound No. | Counter Cation | Color Tone | Paper Dependency | Water Resistance | Light Fastness | Dark Heat Storability | Ozone Resistance | b/a Value | Bronze Phenomenon |
|---|---|---|---|---|---|---|---|---|---|---|
| A | 171 | Li | ○ | A | A | A | A | A | 0.62 | ○ |
| B | 102 | Li | ○ | A | A | A | A | A | 0.74 | ○ |
| C | 172 | Li | ○ | A | A | A | A | A | 0.67 | ○ |
| Comparative Example 1 | 171-Na salt | Na | ○ | A | A | A | A | A | 0.64 | X |
| Comparative Example 2 | 171-K salt | K | ○ | A | A | A | A | A | 0.63 | X |
| Comparative Example 3 | 171-NH$_4$ salt | NH$_4$ | ○ | A | A | A | A | A | 0.54 | X |
| Comparative Example 4 | Comparative Compound 1 | Na | Δ | B | B | B | A | C | 1.00 | ○ |

Comparative Compound 1 — (SO$_3$Na)$_4$

A mixture of substitution sites of 1-position to 16-position

It is seen from the Table above that when a phthalocyanine compound having a specific spectral absorption curve and a specific structure is used, an ink for ink jetting having excellent (color) hue and small paper dependency and being excellent in the water resistance, light fastness and ozone resistance can be obtained and also that when the counter ion for the ionic hydrophilic group is not lithium ion, a bronze phenomenon is generated.

Furthermore, it is seen that in the case of a phthalocyanine compound having a spectral absorption curve out of the specified range of the present invention and not strongly forming the aggregated state, the (color) hue and fastness are very bad, though a bronze phenomenon is not generated even if the counter cation is sodium ion.

Example 3

Using the same cartridge as produced in Example 2, an image was printed on Ink Jet Paper Photo Gloss Paper EX produced by Fuji Photo Film Co., Ltd. by means of the same printer as used in Example 2, and evaluated in the same manner as in Example 2. Then, the same results as in Example 2 were obtained.

Example 4

The same ink as produced in Example 2 was filled in a cartridge of Ink Jet Printer BJ-F850 (manufactured by CANON) and using this printer, an image was printed on a photo gloss paper GP-301 produced by the same company and evaluated in the same manner as in Example 2. Then, the same results as in Example 2 were obtained.

Example 5

A test was performed by using the same operation as in Example 2 except that the test method of Example 2 was changed to the following environmental test method. That is, an oxidative gas resistance test method simulating the outdoor environment exposed to oxidative gases such as exhaust gas of automobile and irradiation with solar light was performed according to an oxidation resistance test method using a fluorescent light irradiation chamber at a relative humidity of 80% and a hydrogen peroxide concentration of 120 ppm described in H. Iwano et al., *Journal of Imaging Science and Technology*, Vol. 38, 140–142 (1944). The test results were the same as those in Example 2.

While the invention has been described in detail and with reference to specific embodiments thereof, it will be apparent to one skilled in the art that various changes and modifications can be made therein without departing from the spirit and scope thereof.

This application is based on Japanese patent application No. 2002-12864 filed on Jan. 22, 2002, the entire contents thereof being hereby incorporated by reference.

INDUSTRIAL APPLICABILITY

Phthalocyanine-base dyes widely used in general at present, represented by Direct Blue 87 and Direct Blue 199, are excellent in the light fastness as compared with generally known magenta dyes, yellow dyes and triphenylmethane-base cyanine dyes.

However, the phthalocyanine-base dyes provide a greenish (color) hue under acidic conditions and are improper for a cyan ink. In the case of using these dyes for a cyanine ink, these are most suitably used under conditions from neutral to alkaline. However, even if the ink is in the region from neutral to alkaline, when the material on which an image or the like is recorded is an acidic paper, the (color) hue of the printed matter may greatly change.

Furthermore, discoloration to a greenish (color) hue or decoloration occurs due to oxidative gases such as nitrogen oxide gas and ozone, which are often taken as a problem also from an environmental issue, and this simultaneously causes reduction in the printing density.

On the other hand, triphenylmethane-base dyes provide a good (color) hue but are very inferior in the light fastness, resistance against ozone gas and the like.

In view of the above problems, the following effects have been found out by the present invention.

According to the present invention, 1) an ink comprising a phthalocyanine compound, having absorption properties with excellent color reproducibility and showing sufficiently high fastness to light, heat, humidity and active gases in the environment, 2) an ink composition for printing such as ink jetting, using the above-described ink and capable of forming an image free of generation of a bronze phenomenon, and 3) a method capable of improving the fastness of the image recorded material against light and active gases in the environment, particularly ozone gas, can be provided.

The invention claimed is:

1. An ink comprising a water-soluble phthalocyanine compound, wherein in the spectral absorption curve of an aqueous solution of said phthalocyanine compound, the absorbance ratio b/a of the maximum absorbance b in the absorption band of 660 to 680 nm and the maximum absorbance a in the absorption band of 600 to 640 nm is less than 0.8 and the counter ion for the ionic hydrophilic group of said phthalocyanine compound is lithium ion.

2. An ink for ink jetting, comprising the ink claimed in claim 1.

3. An ink jet recording method comprising forming an image on an image-receiving material using the ink for ink jetting claimed in claim 2, the image receiving material comprising a support having thereon an ink image-receiving layer containing a white inorganic pigment particle.

4. A method for improving ozone gas discoloration of an image recorded material, comprising forming an image using the ink claimed in claim 1.

5. A water-soluble phthalocyanine compound represented by the following formula (IV):

Formula (IV):

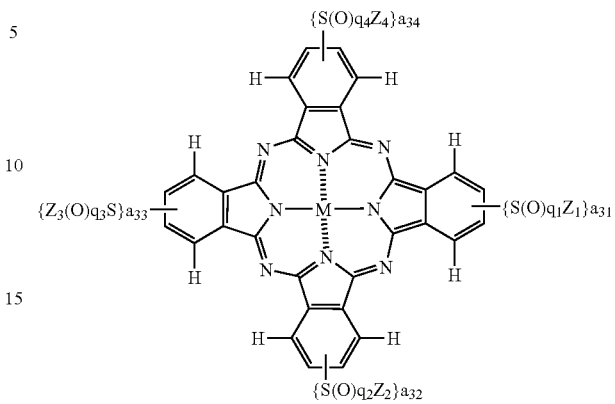

wherein $Z_1$, $Z_2$, $Z_3$ and $Z_4$ each independently represents a substituted or unsubstituted alkyl group, a substituted or unsubstituted cycloalkyl group, a substituted or unsubstituted alkenyl group, a substituted or unsubstituted aralkyl group, a substituted or unsubstituted aryl group or a substituted or unsubstituted heterocyclic group, $q_1$, $q_2$, $q_3$ and $q_4$ each independently represents an integer of 1 or 2, $a_{31}$, $a_{32}$, $a_{33}$ and $a_{34}$ each independently represents an integer of 1 or 2, M has the same meaning as M in formula (I), and at least one of $Z_1$, $Z_2$, $Z_3$ and 4 has an ionic hydrophilic group as a substituent, provided that the counter ion for the ionic hydrophilic group is lithium.

6. An ink comprising a water-soluble phthalocyanine compound, wherein said phthalocyanine compound is represented by the following formula (I):

Formula (I):

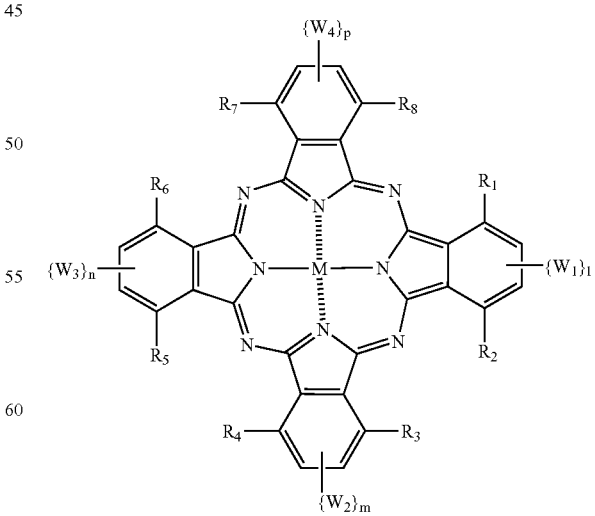

wherein $R_1$, $R_2$, $R_3$, $R_4$, $R_5$, $R_6$, $R_7$ and $R_8$ each independently represents a hydrogen atom, a halogen atom, an alkyl group, a cycloalkyl group, an alkenyl group, an aralkyl group, an aryl group, a heterocyclic group, a cyano group, a hydroxyl group, a nitro group, an amino group, an alkylamino group, an alkoxy group, an aryloxy group, an amido group, an arylamino group, a ureido group, a sulfamoylamino group, an alkylthio group, an arylthio group, an alkoxycarbonylamino group, a sulfonamido group, a carbamoyl group, a sulfamoyl group, a sulfonyl group, an alkoxycarbonyl group, a heterocyclic oxy group, an azo group, an acyloxy group, a carbamoyloxy group, a silyloxy group, an aryloxycarbonyl group, an aryloxycarbonylamino group, an imido group, a heterocyclic thio group, a sulfinyl group, a phosphoryl group or an acyl group and each may further have a substituent;

$W_1$, $W_2$, $W_3$ and $W_4$ each independently represents the group represented by $R_1$, $R_2$, $R_3$, $R_4$, $R_5$, $R_6$, $R_7$ and $R_8$, a sulfonylsulfamoyl group or an acylsulfamoyl group and each may further have a substituent, provided that at least one of $W_1$, $W_2$, $W_3$ and $W_4$ is an ionic hydrophilic group by itself or has an ionic hydrophilic group as a substituent, provided that the counter ion for the ionic hydrophilic group is lithium ion; l, m, n and p each represents an integer of 1 or 2; and M represents a hydrogen atom, a metal element, a metal oxide, a metal hydroxide or a metal halide.

7. The ink as claimed in claim 6, wherein said formula (I) is represented by the following formula (II):

Formula (II):

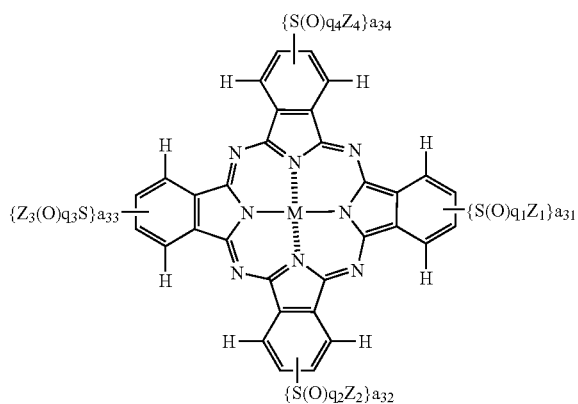

wherein $Z_1$, $Z_2$, $Z_3$ and $Z_4$ each independently represents a substituted or unsubstituted alkyl group, a substituted or unsubstituted cycloalkyl group, a substituted or unsubstituted alkenyl group, a substituted or unsubstituted aralkyl group, a substituted or unsubstituted aryl group or a substituted or unsubstituted heterocyclic group, $q_1$, $q_2$, $q_3$ and $q_4$ each independently represents an integer of 1 or 2, $a_{31}$, $a_{32}$, $a_{33}$ and $a_{34}$ each independently represents an integer of 1 or 2, M has the same meaning as M in formula (I), and at least one of $Z_1$, $Z_2$, $Z_3$ and $Z_4$ has an ionic hydrophilic group as a substituent, provided that the counter ion for the ionic hydrophilic group is lithium ion.

8. The ink as claimed in claim 7, wherein in formula (II), $q_1=q_2=q_3=q_4=2$.

9. The ink as claimed in claim 6, wherein said formula (I) is represented by the following formula (III):

Formula (III):

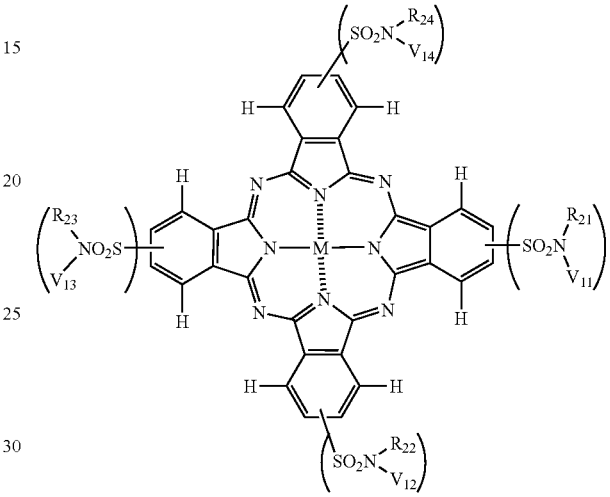

wherein $R_{21}$, $R_{22}$, $R_{23}$ and $R_{24}$ each independently represents a hydrogen atom, a substituted or unsubstituted alkyl group, a substituted or unsubstituted cycloalkyl group, a substituted or unsubstituted alkenyl group, a substituted or unsubstituted aralkyl group, a substituted or unsubstituted aryl group or a substituted or unsubstituted heterocyclic group, $V_{11}$, $V_{12}$, $V_{13}$ and $V_{14}$ each independently represents a substituted or unsubstituted alkyl group, a substituted or unsubstituted cycloalkyl group, a substituted or unsubstituted alkenyl group, a substituted or unsubstituted aralkyl group, a substituted or unsubstituted aryl group, or a substituted or unsubstituted heterocyclic group, M has the same meaning as M in formula (I), and at least one of $R_{21}$, $R_{22}$, $R_{23}$, $R_{24}$, $V_{11}$, $V_{12}$, $V_{13}$ and $V_{14}$ has an ionic hydrophilic group as a substituent, provided that the counter ion for the ionic hydrophilic group is lithium ion.

10. The ink as claimed in claim 6, wherein at least one electron-withdrawing group substitutes at the β-position of the phthalocyanine nucleus.

* * * * *